United States Patent [19]
Lynch et al.

[11] Patent Number: 6,050,138
[45] Date of Patent: Apr. 18, 2000

[54] SYSTEM AND METHOD FOR PERFORMING BULGE TESTING OF FILMS, COATINGS AND/OR LAYERS

[75] Inventors: Kevin R. Lynch, Sommerville; Richard Mlack; Paulo Jorge Furtado Correia, both of Cambridge; Stuart B. Brown, Needham; Christopher L. Muhlstein, Brookline, all of Mass.

[73] Assignee: Exponent, Inc., Menlo Park, Calif.

[21] Appl. No.: 08/955,928

[22] Filed: Oct. 22, 1997

[51] Int. Cl.[7] .................................................. G01N 3/10
[52] U.S. Cl. .............................................. 73/150 A; 73/827
[58] Field of Search ........................... 73/812, 807, 826, 73/827, 838, 841, 150 R, 150 A

[56] References Cited

U.S. PATENT DOCUMENTS

| | | | |
|---|---|---|---|
| 4,402,218 | 9/1983 | Engle | 73/146 |
| 4,674,332 | 6/1987 | Pace et al. | |
| 4,735,092 | 4/1988 | Kenny | 73/840 |
| 4,899,581 | 2/1990 | Allen et al. | 73/150 A |
| 5,255,562 | 10/1993 | Yamamoto et al. | |
| 5,417,865 | 5/1995 | Scheucher et al. | 210/739 |
| 5,517,860 | 5/1996 | Lin et al. | 73/789 |
| 5,546,811 | 8/1996 | Rogers et al. | |

OTHER PUBLICATIONS

"Poisson's Ration Evaulation of Thin Film for Sensor Application": Technical Digest of the 12th Sensor Symposium, 1994. pp. 19–22; Tabata et al.

"Mechanical Property Measurements of Thin Films Using Load–Deflection of Composite Rectangular Membranes" *Sensors and Actuators*, 20; (1989) pp. 135–141 Elsevier Sequoia.

"Mechanical Behavior of Thin Films" by Richard P. Vinci and Joost J. Vlassak, Annu. Rev. Mater. Sci. 1996.

"Measuring the Mechanical Properties of Thin Metal Films by Means of Bulge Testing of Micromachined Windows" by W.M. Paviot, J.J. Vlassak, and W.D. Nix, Mat. Sci. Symp. Proc. vol. 356, 1995.

"Mechanical Properties of Thin Films on Substrates" by S.P. Baker and W.D. Nix, SPIE vol. 1323 Optical Thin Films III: New Developments, 1990.

"Mechanical Properties of Thin Films" by William D. Nix, Metallurgical Transactions A, vol. 20A, Nov., 1989.

"Chapter 3, The Bulge Test: A Technique for Measuring the In–Plane Mechanical Properties of Thin Films" by Vlassak (1994), found in New Experimental Techniques and Analysis Methods for the Study of Mech. Prop. of Materials in Small Volume.

"The In–Situ Measurement of Mechanical Properties of Multi–Layer Coatings" by Pinyen Lin, Massachusetts Institute of Technology, 1990.

*Primary Examiner*—Max Noori
*Attorney, Agent, or Firm*—Liniak, Berenato, Longacre & White

[57] ABSTRACT

A system and corresponding method for bulge testing films (e.g. thin films, coatings, layers, etc.) is provided, as well as membrane structures for use in bulge testing and improved methods of manufacturing same so that resulting membrane structures have substantially identical known geometric and responsive characteristics. Arrayed membrane structures, and corresponding methods, are provided in certain embodiments which enable bulge testing of a film(s) over a relatively large surface area via a plurality of different free-standing membrane portions. Improved measurements of film bulging or deflection are obtained by measuring deflection of a center point of a film, relative to non-deflected peripheral points on the film being tested. Furthermore, membrane structures are adhered to mounting structure in an improved manner, and opaque coatings may be applied over top of film(s) to be bulge tested so that a corresponding optical transducer can more easily detect film deflection/bulging. In certain embodiments, a laser triangulation transducer is utilized to measure film deflection/bulging.

20 Claims, 71 Drawing Sheets

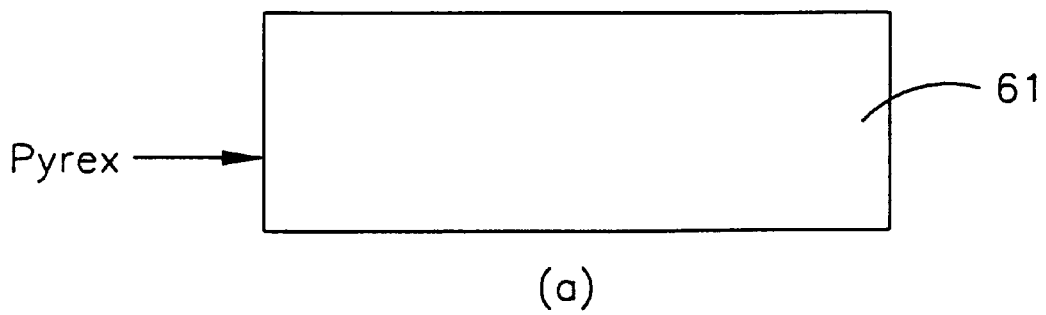
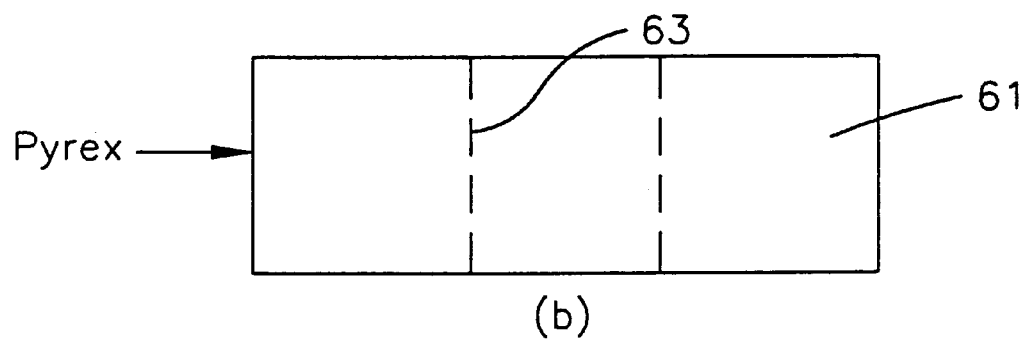
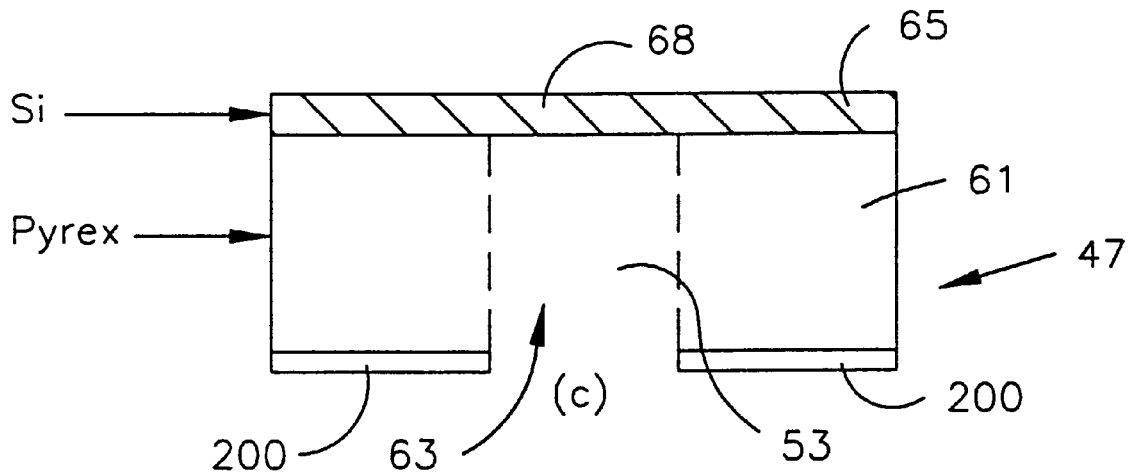
FIG. 6

View of Top Surface with Two Bonded Wafers

Connector Pane

INRAMP4.V

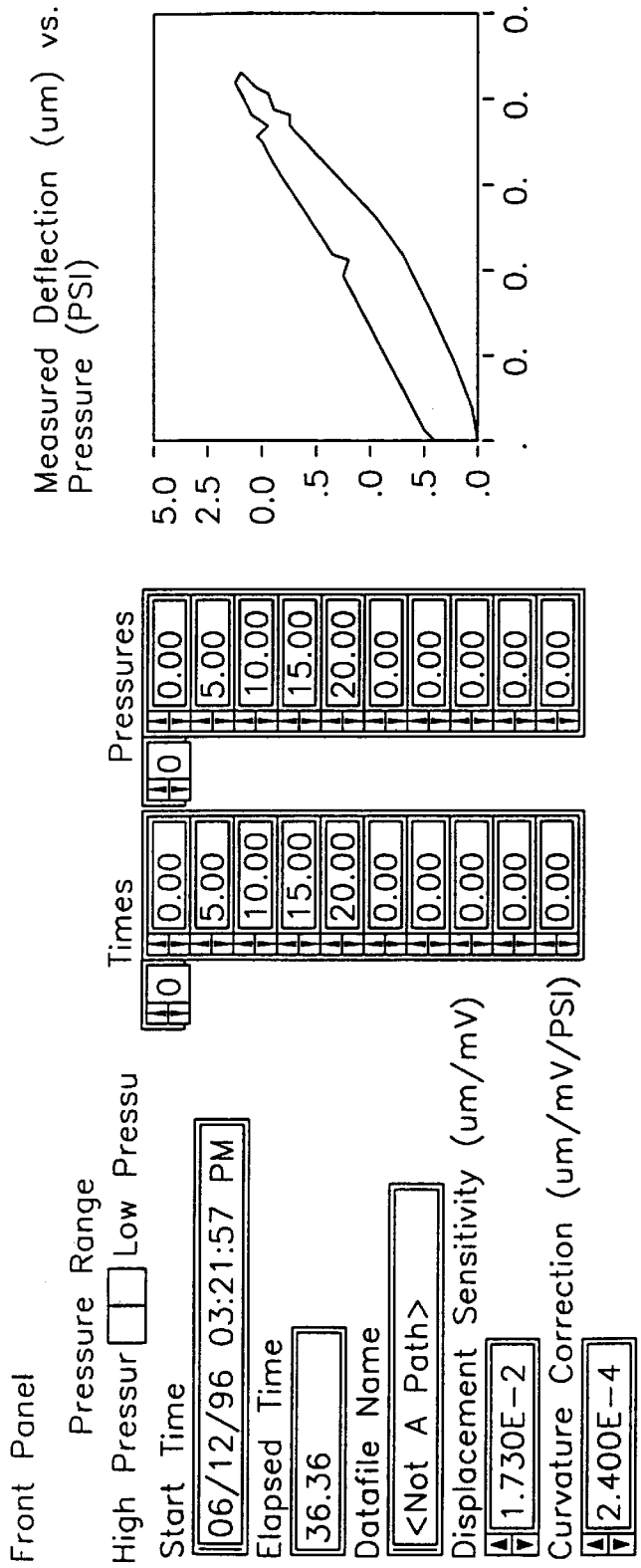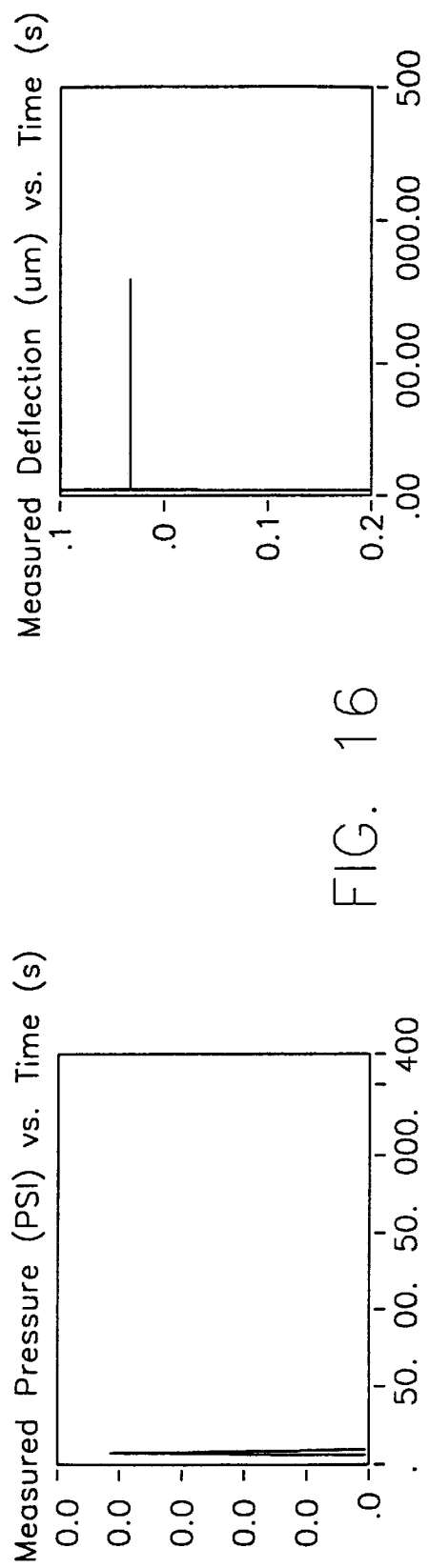
FIG. 16

Controls and Indicators

[DBL] Pressures
　[DBL]

[DBL] Displacement Sensitivity (um/mV)

[DBL] Times
　[DBL]

[DBL] Curvature Correction (um/mV/PSI)

[TF] Pressure Range

[▦] Measured Deflection (um) vs. Time (s)

[▦] Measured Deflection (um) vs. Pressure (PSI)

[▦] Measured Pressure (PSI) vs. Time (s)

[abc] Start Time

[DBL] Elapsed time

[abc] Datafile Name

FIG. 17

Block Diagram
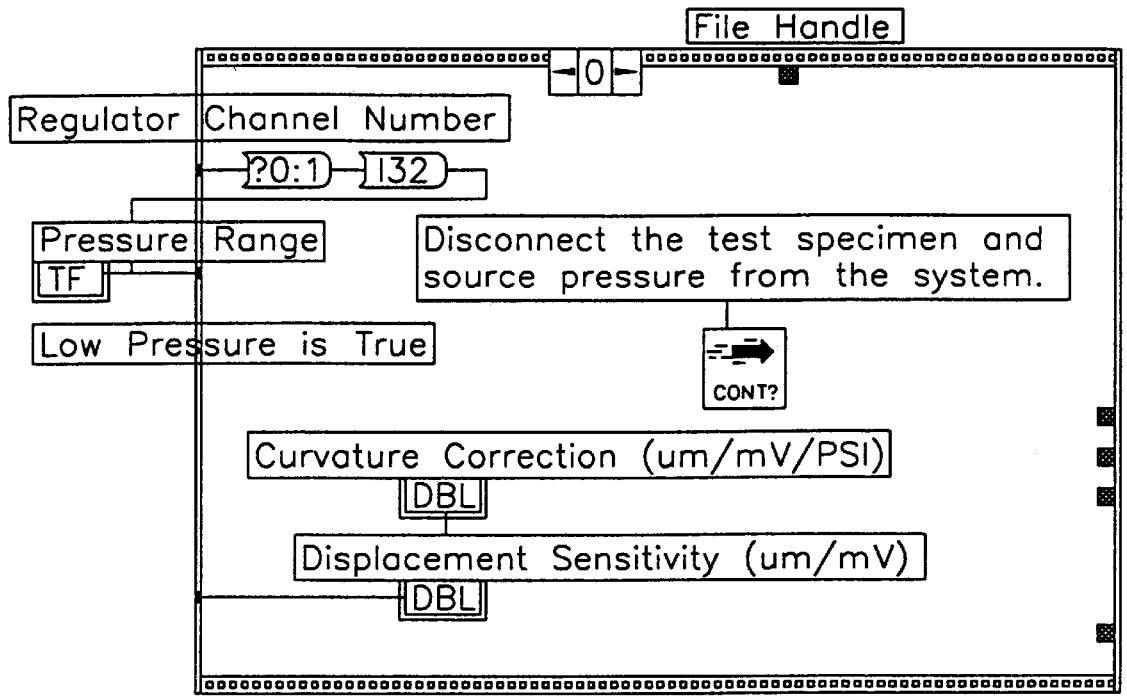
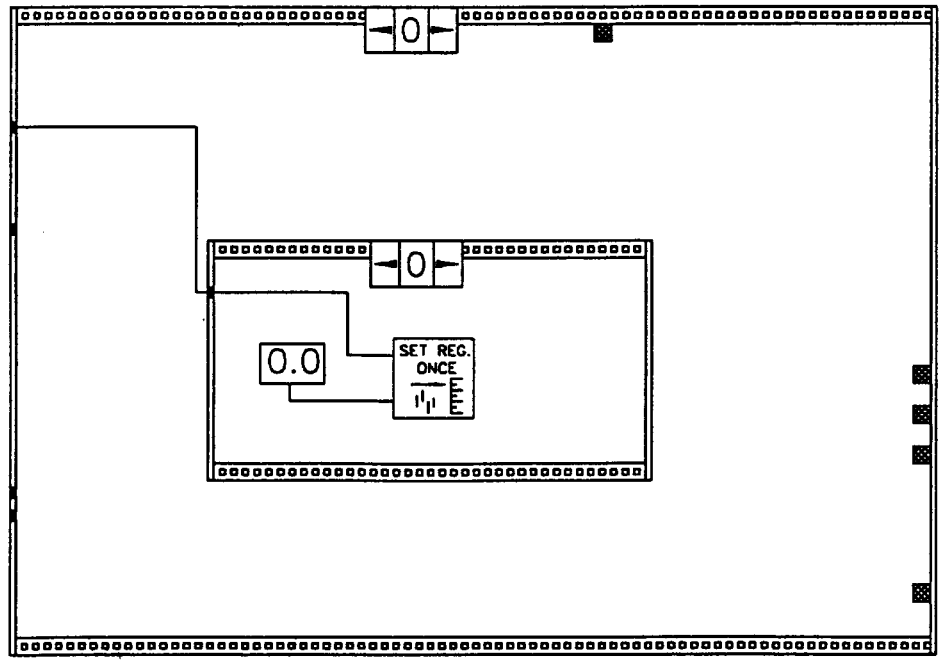
FIGURE 18

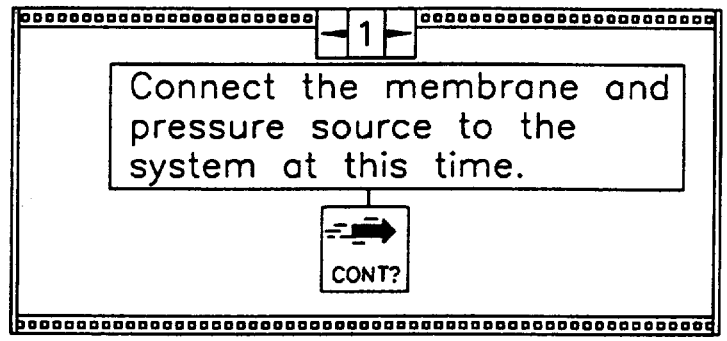
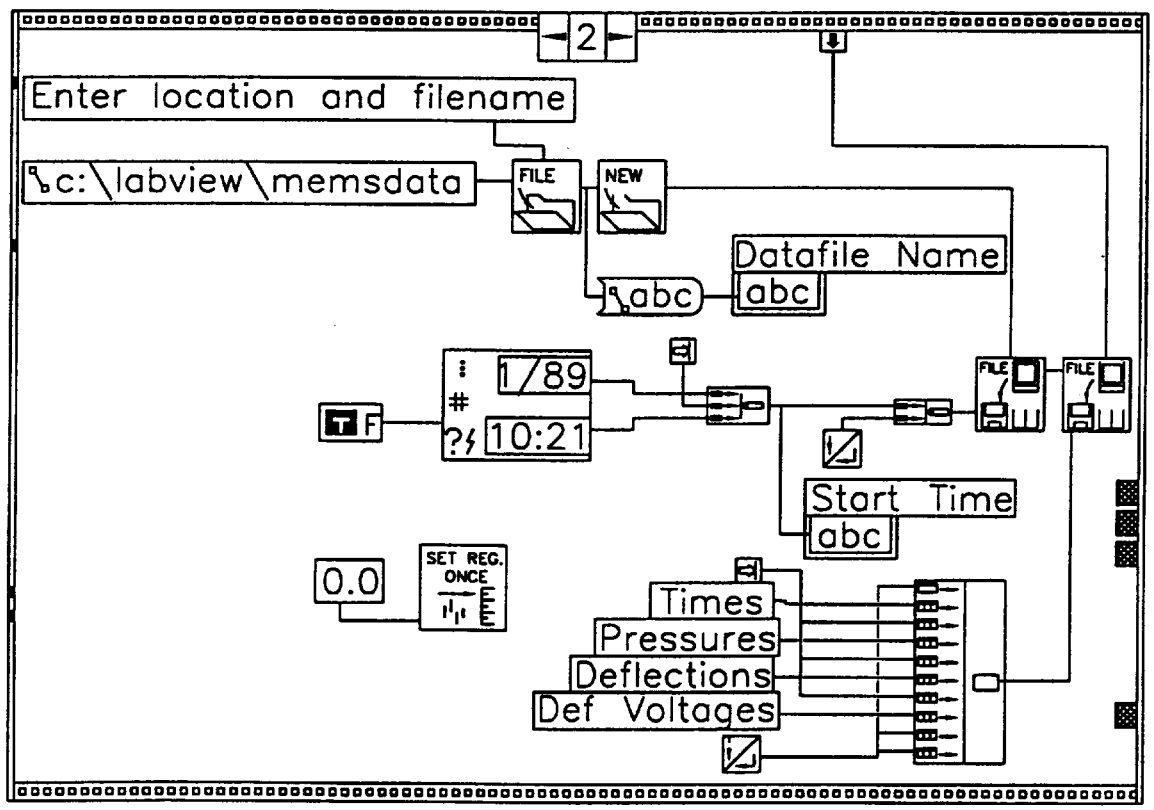
FIGURE 19

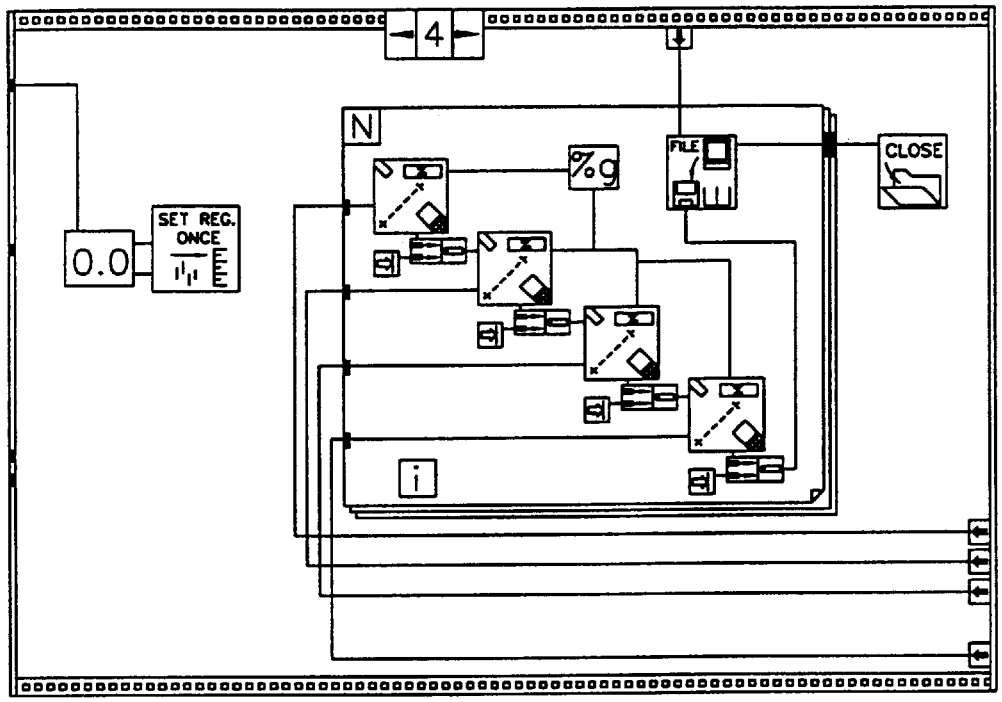
Position in Hierarchy
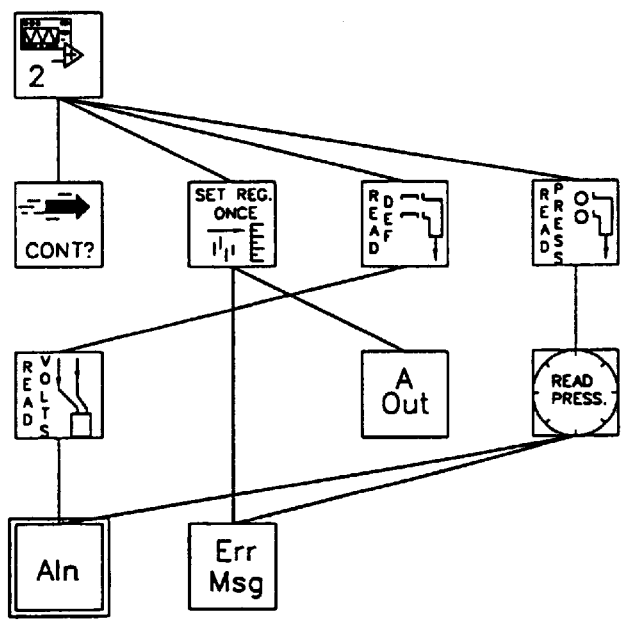
FIGURE 21

List of SubVIs

Read Pressure .vi
O:\PROJECTS\CHRIS\CASES\BN61218\MEMSCODE\
MEMBRANE\SUPPORT.LLB\
Pressure.vi

Read Deflection .vi
O:\PROJECTS\CHRIS\CASES\BN61218\MEMSCODE\
MEMBRANE\SUPPORT.LLB\
Deflection.vi

Set Regulator Once .vi
O:\PROJECTS\CHRIS\CASES\BN61218\MEMSCODE\
MEMBRANE\SUPPORT.LLB\
REgulator Once.vi

Continue .vi
O:\PROJECTS\CHRIS\CASES\BN61218\MEMSCODE\
MEMBRANE\SUPPORT.LLB\C
.vi History "LINRAMP4.VI History"
Current Revision: 48

FIGURE 22

Connector Pane

Controls and Indicators
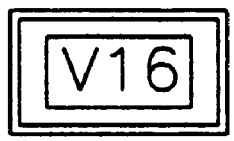 Output Units (PSI)
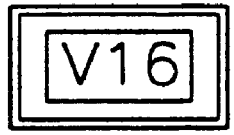 Range Selector
 Averaging Cycles
 Pressure Measured
FIGURE 25

Block Diagram
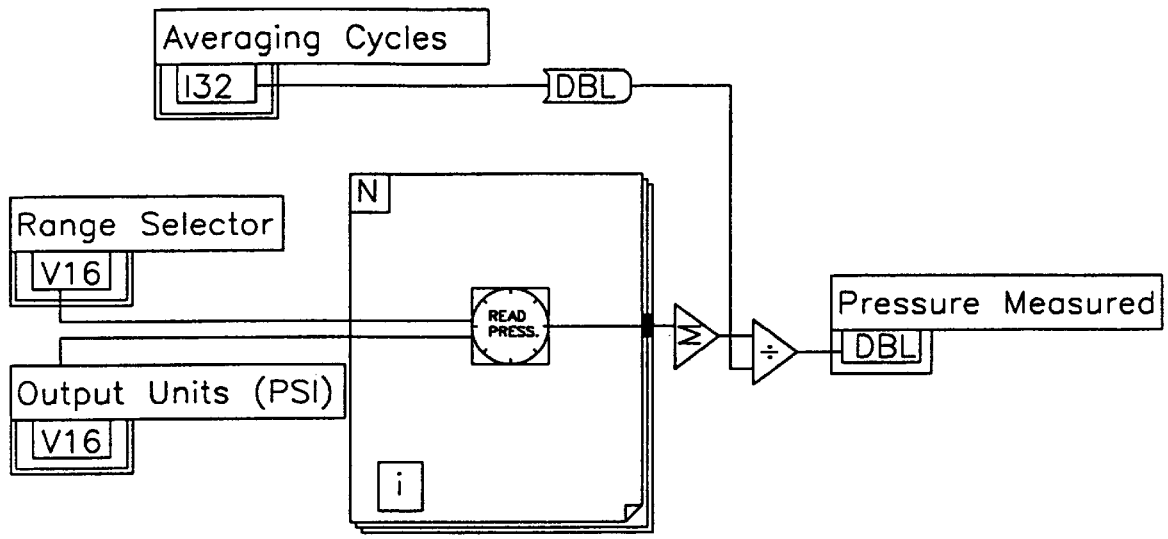
Position in Hierarchy
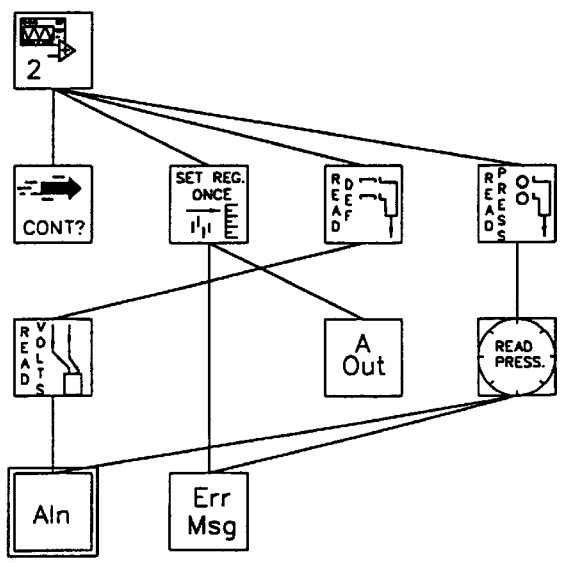
FIGURE 26

List of SubVIs

Read Pressure Once .vi
O:\PROJECTS\CHRIS\CASES\BN61218\MEMSCODE\
MEMBRANE\SUPPORT.LLB\
Pressure Once .vi History "Read Pressure .vi History"
Current Revision: 9

Connector Pane

Read Deflection .vi

Controls and Indicators
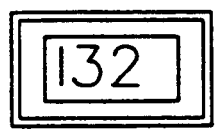 Averaging Cycles
 Error Message
 Deflection Voltage (V)
FIGURE 30

Block Diagram
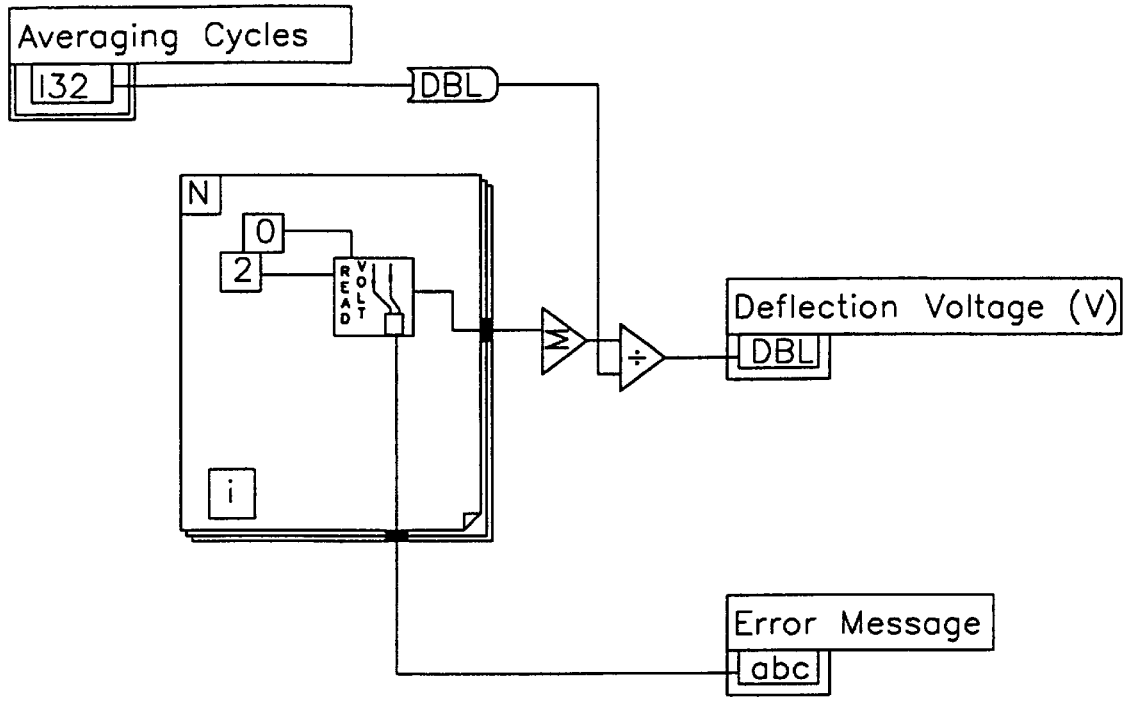
Position in Hierarchy
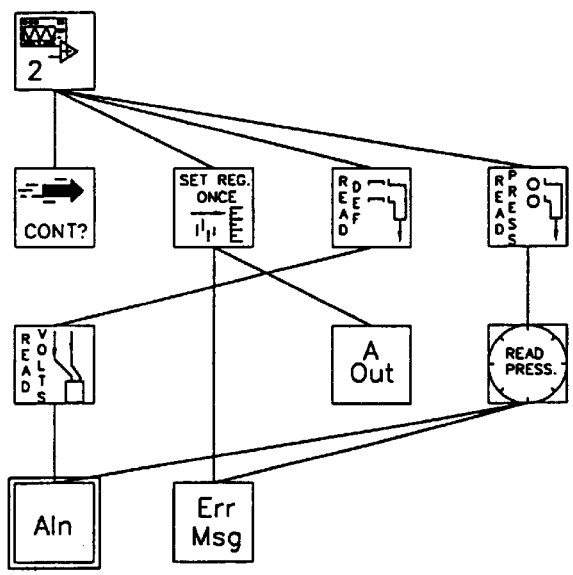
FIGURE 31

List of SubVIs

Read Voltage Once .vi
O:\PROJECTS\CHRIS\CASES\BN61218\MEMSCODE\
MEMBRANE\SUPPORT.LLB
voltage Once .vi History
   "Read Deflection .vi History"
   Current Revision: 13

Connector Pane

Controls and Indicators
 Pressure to Set (0)
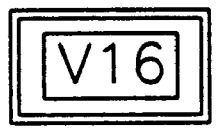 Pressure Units (1:PSI)
 Channel Number (0)
 Board Number (0)
 Error Message
FIGURE 35

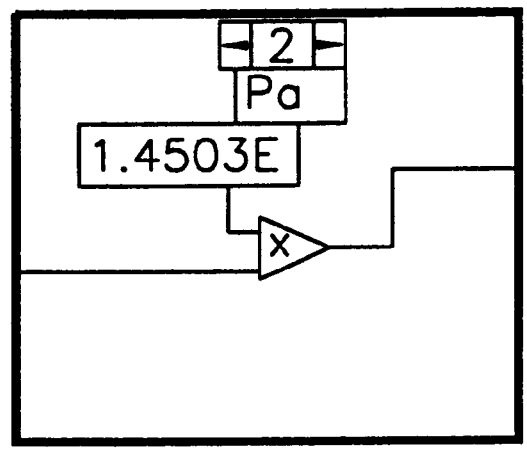
Position in Hierarchy
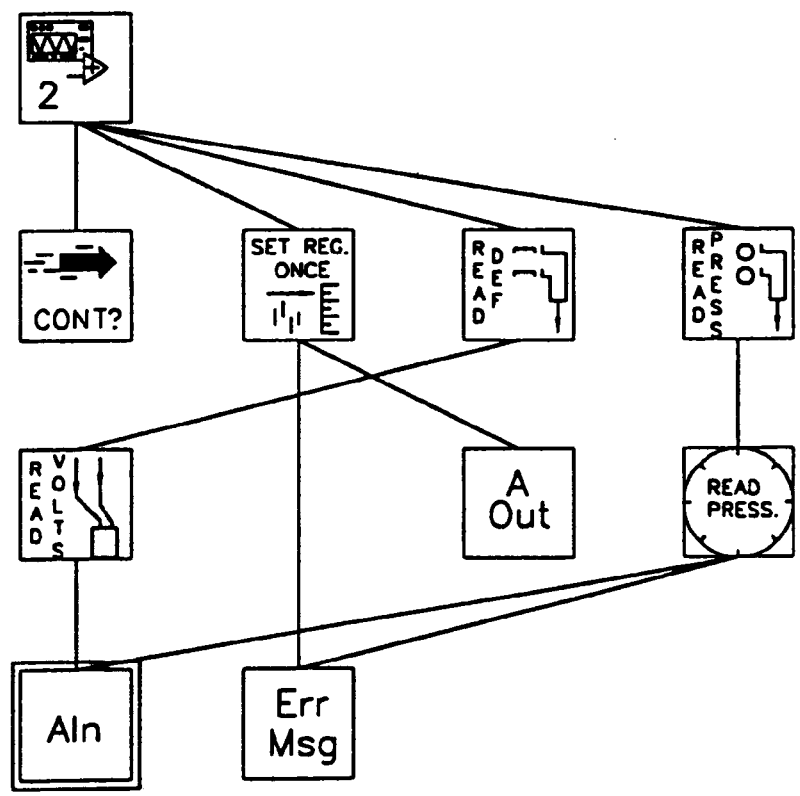
FIGURE 37

List of SubVIs
 AOut.VI
D:\LBVIEW3\vi.lib\CB\DAS16.LLB\AOut.VI
 ErrMsg.VI
D:\LBVIEW3\vi.lib\CB\DAS16.LLB\ErrMsg.VI
History
"Set Regulator Once .vi History"
Current Revision: 10
FIGURE 38

Connector Pane

Action Prompt 
Continue .vi

This VI implements a pop up dialog like box which permits prompts the user to commit to some before permitting program to continue.

Controls and Indicators

Action Prompt

Block Diagram

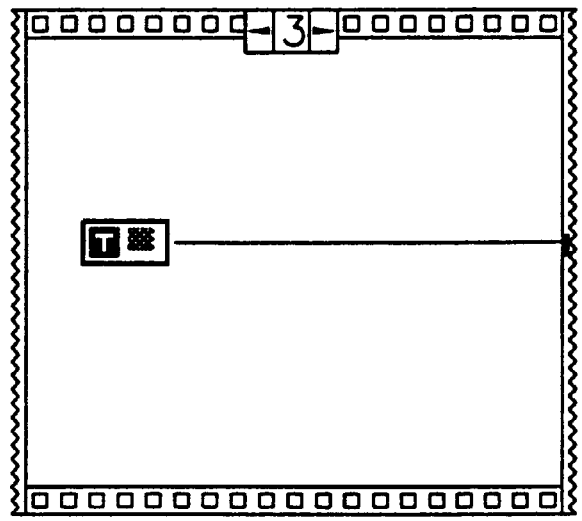
Position in Hierarchy
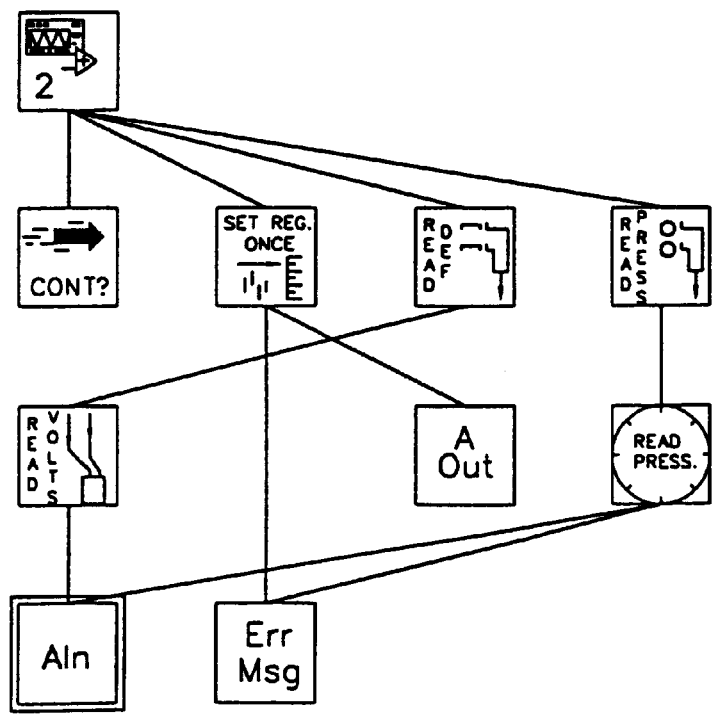
FIGURE 43

List of Sub VIs

History

"Continue .vi History"
Current Revision: 16

FIGURE 44

Connector Pane

Read Pressure Once .vi

This VI reads the Pressure from the numbered gauge, using the Computer Boards interface card Board Number. It also accepts a parameter specifying the units of the output value. This default
Other possible settings are:

(0) PSI; (1) Pa; (2) MPa

Controls and Indicators
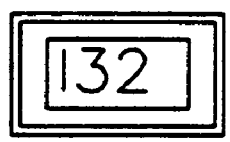 Gauge Number (0)
 Output Units (PSI)
 Board Number (0)
 Pressured Measured
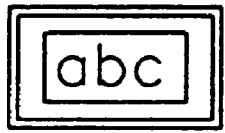 Error Message
 Voltage Measured
FIGURE 47

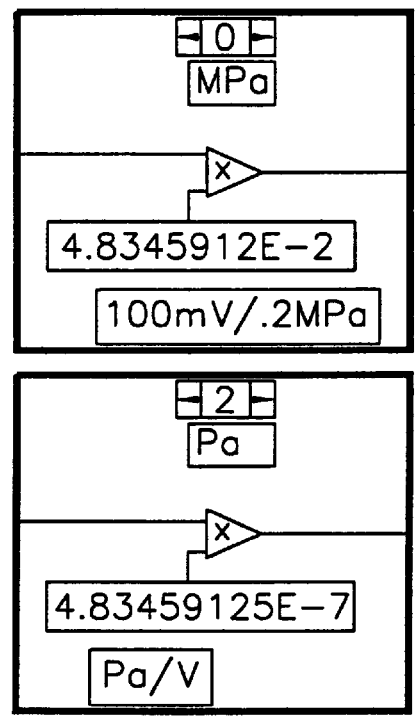
Position in Hierarchy
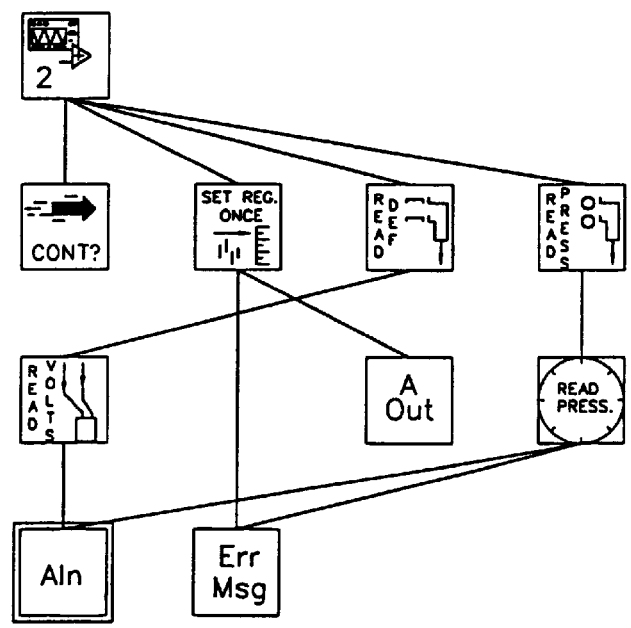
FIGURE 49

List of SubVIs
AIn.VI
D:\LBVIEW3\vi.lib\CB\DAS16.LLB\AIn.VI
ErrMsg.VI
D:\LBVIEW3\vi.lib\CB\DAS16.LLB\ErrMsg.VI
History
"Read Voltage ONce.vi History"
Current Revision: 21
FIGURE 50

Connector Pane

Board Number (0) ──────┐ ┌────── Output Bit Value
Gauge Number (0) ──┐   │ │   ┌── Voltage (V)

└── Error Message

Read Voltage Once .vi

This VI reads the value measured by the reflectance displacement sensor and returns the value in mm.

Front Panel

| BoardNum(0) | Voltage (V) |
| --- | --- |
| 0 | 0.00 |
| Gauge Number (0) | Output Bit Value |
| 2 | 0 |

Error Message
No error has occurred

FIGURE 52

Controls and Indicators
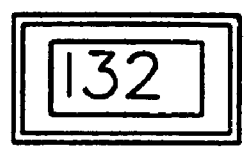 Gauge Number (0)
 Board Number (0)
 Error Message
 Voltage (V)
 Output Bit Value
FIGURE 53

Block Diagram
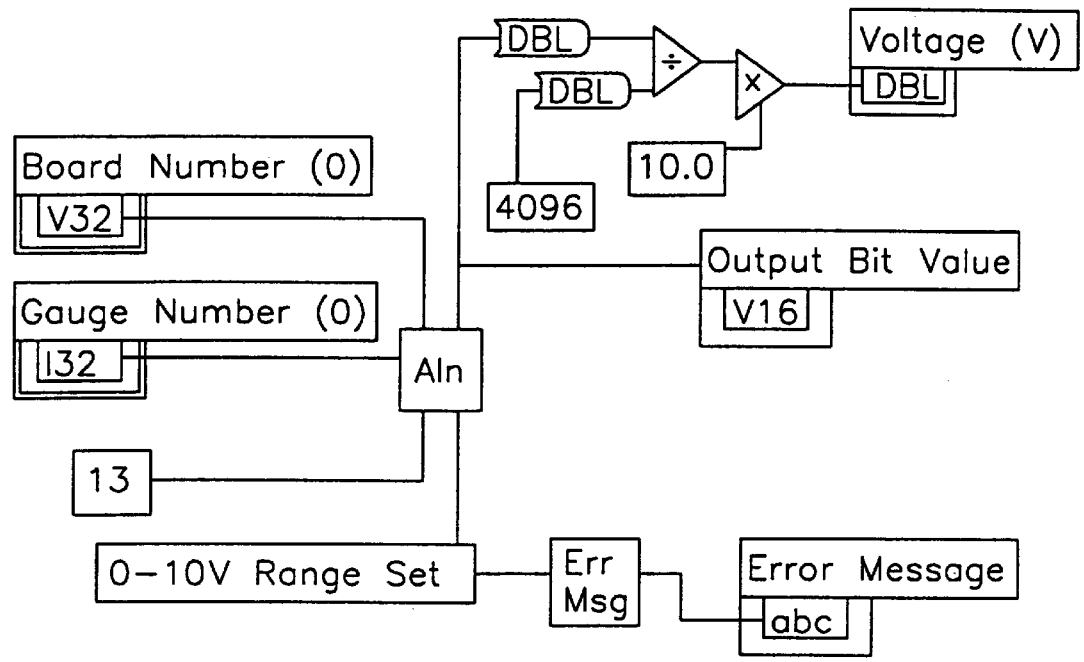
Position in Hierarchy
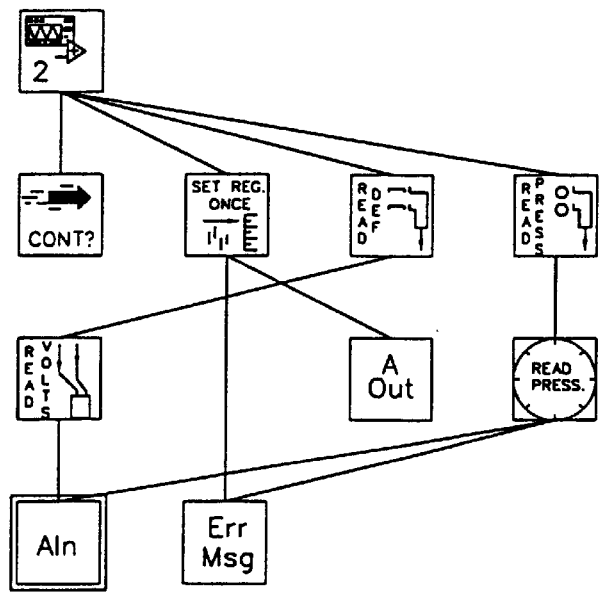
FIGURE 54

List of SubVIs
Aln.VI
D:\LBVIEW3\vi.lib\CB\DAS16.LLB\Aln.VI
ErrMsg.VI
D:\LBVIEW3\vi.lib\CB\DAS16.LLB\ErrMsg.VI
History
"Read Voltage ONce.vi History"
Current Revision: 20
FIGURE 55

Connector Pane

AOut.VI

Sets the value of a D/A output.

Front Panel

Controls and Indicators
 BoardNum(0)
Board number (0..9).
 Channel
A/D channel number.
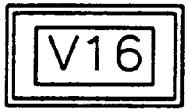 Data Value
Value to set D/A to.
 Range
A/D range code. Use "Not Programmable" for boards not featuring programmable ra
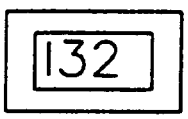 ErrCode
Error code.
FIGURE 58

Block Diagram
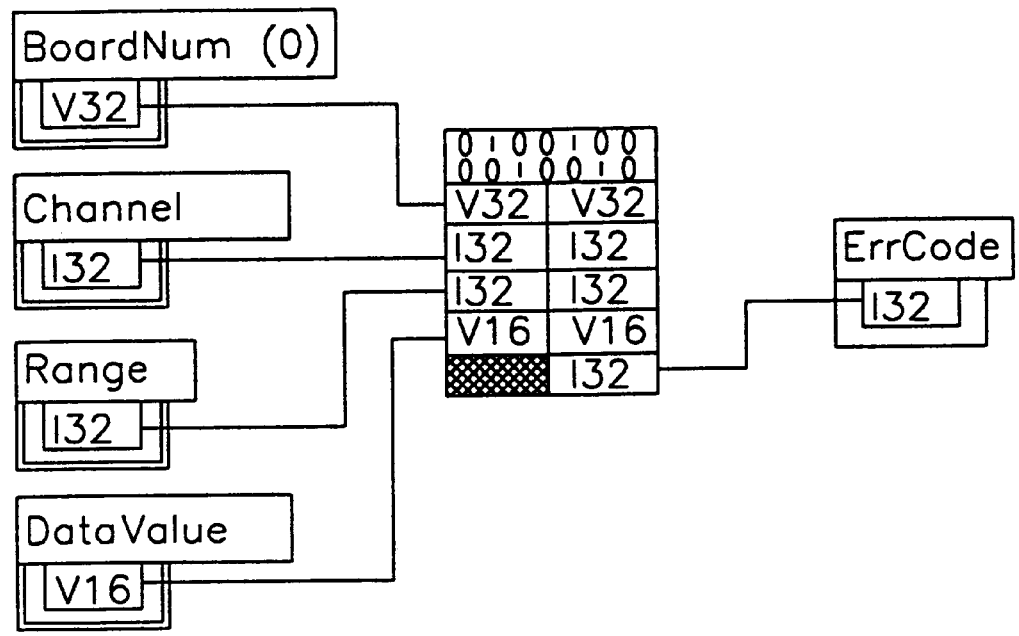
Position in Hierarchy
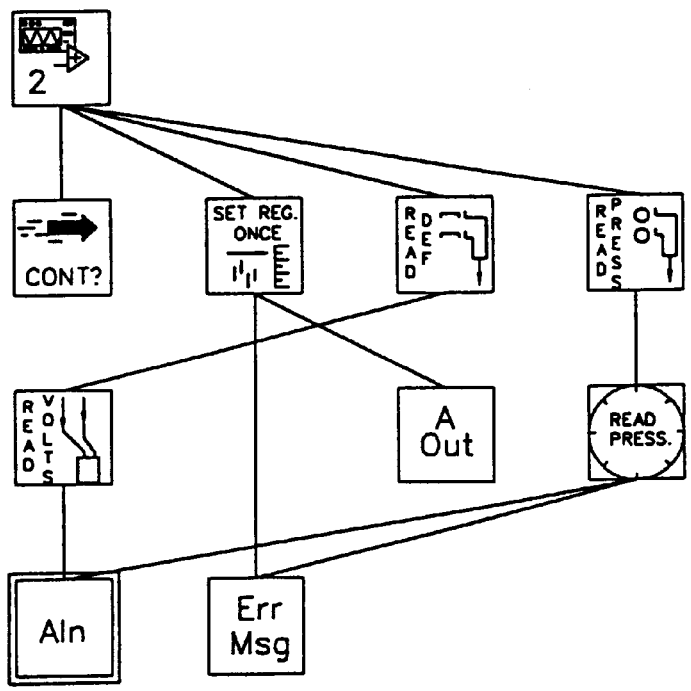
FIGURE 59

History

"AOut.VI History"
    Current Revision: 0

FIGURE 60

Connector Pane

ErrMsg.VI

Returns the error message associated with an error code (cbGetErrMsg).

Controls and Indicators
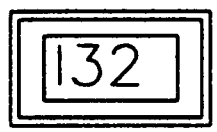 ErrCode
Error code input.
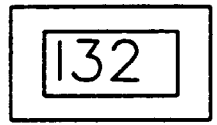 ErrCode
Error code.
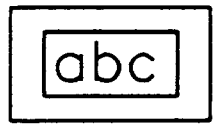 ErrMsg
Error text.
FIGURE 63

Block Diagram
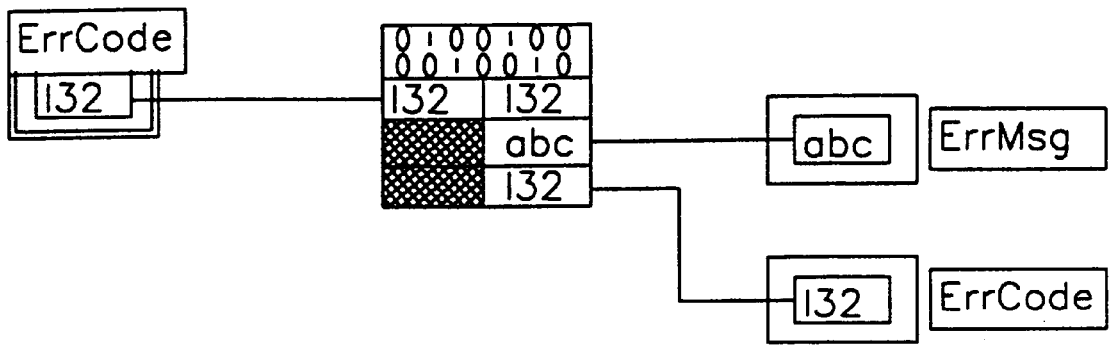
Position in Hierarchy
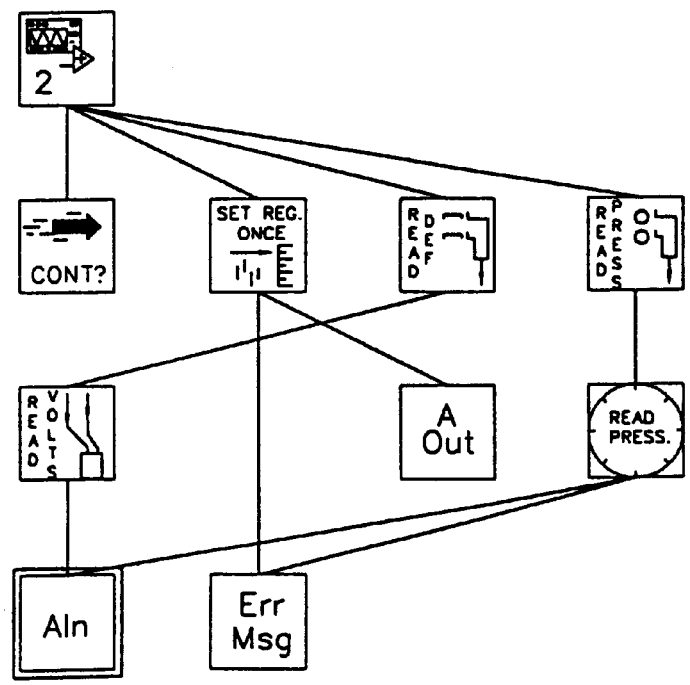
FIGURE 64

History

"ErrMsg.VI History"
Current Revision: 0

FIGURE 65

Connector Pane

Reads an A/A input channel.

Front Panel

Controls and Indicators
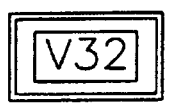 BoardNum(0)
Board number (0..9).
 Channel (0)
A/D channel number.
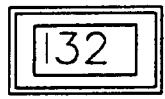 Range
A/D range code. Use "Not Programmable" for boards not featuring programmable ra
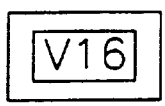 Data Value
Digital output value.
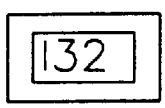 ErrCode
Error doe from the ComputerBoards Inc. Universal Library. Zero if no error occured. U ErrMsg VI to convert ErrCode into a readable string.
FIGURE 68

Block Diagram
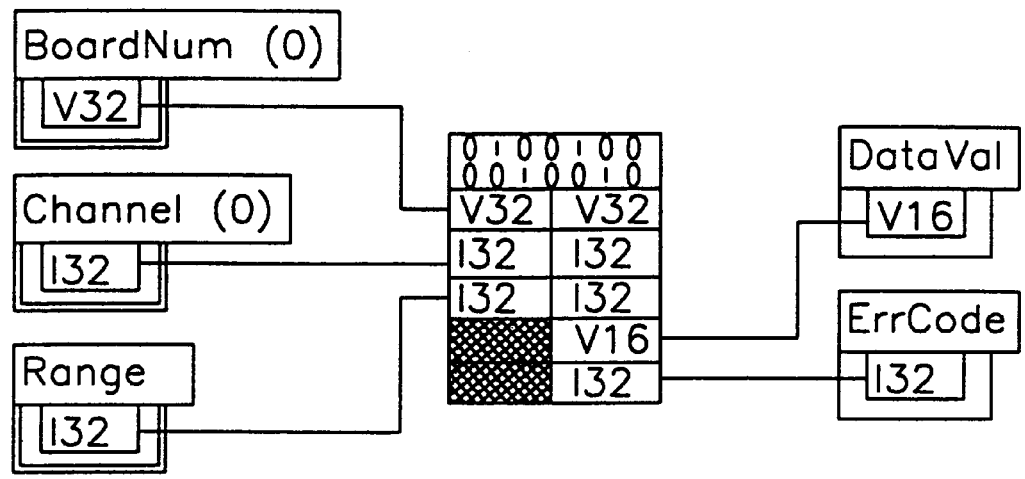
Position in Hierarchy
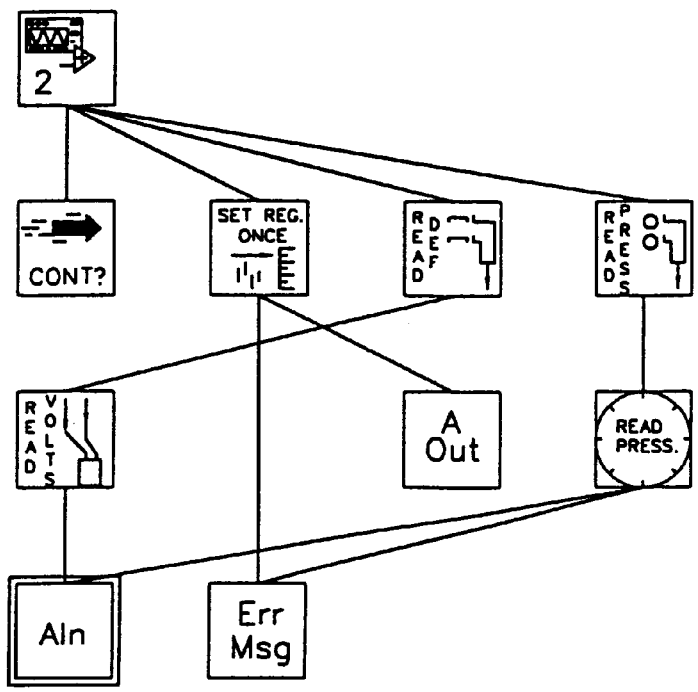
FIGURE 69

History

"Aln.VI History"
Current Revision: 1

FIGURE 70

SYSTEM AND METHOD FOR PERFORMING BULGE TESTING OF FILMS, COATINGS AND/OR LAYERS

This application relates to an inexpensive, accurate, and efficient system and method for performing bulge testing of films, coatings, and/or layers. More particularly, this invention relates to improved systems and methods for performing bulge testing of such films, coatings, and/or layers, including improved methods of manufacture, improved membranes for use in such testing, improved methods for manufacturing membranes, improved testing components, improved testing procedures, and improved materials for use with same. Systems and methods herein enable the determination of elastic properties, inelastic properties, time-dependent properties, residual stresses, and the like by measuring the bulging of a membrane and/or film when one side thereof experiences an increase or decrease in pressure. In certain alternative embodiments, bulging caused by inherent pre-stress (without application of pressure or evacuation) in the film is measured to determine the aforesaid properties.

CLAIM TO COPYRIGHT IN REFERENCE TO APPENDIX

An appendix portion of the disclosure of this patent application contains material which is subject to copyright protection (see FIGS. 15–70). 37 C.F.R. §1.96(a)(1). The copyright owner has no objection to the reproduction by anyone of the patent document as it appears in the Patent and Trademark Office files or records, but otherwise reserves all copyrights whatsoever. Instructions for software for carrying out some of the methods and systems, has been filed with the United States Patent and Trademark Office herewith as FIGS. 15–70.

BACKGROUND OF THE INVENTION

It is known that properties of a film, coating, or layer of a given material differ from those of the same material in bulk form. For example, thin films have different yield stresses, creep behavior, and elastic properties than do bulk forms of the same material. The only way to determine the qualities or properties of thin films is to measure the films themselves.

As technology advances, many elements including storage media (e.g. disks), integrated circuits, cutting tools, sensor arrays, wear surfaces, LCD matrix arrays, and the like include films, coatings, and/or layers deposited on a substrate. The term "film" as used herein is to encompass films, coatings, and layers of varying thicknesses. Typically, each film (e.g. thin film) has different residual stress characteristics and different thermal and/or mechanical properties, which may affect the performance, reliability, or durability of devices including such films. The ability to determine mechanical properties and residual stress characteristics of thin films is thus desired. Bulge testing is one way in which to do this.

In prior art bulge testing systems, as shown in FIG. 1, circular or rectangular film 1 having a thickness "t" is clamped over cavity or orifice 3 in mounting structure 5, and pressure is applied to the bottom side of film 1 from within the orifice. The out-of-plane deflection or bulging of film 1 is measured as a function of the applied pressure enabling determination of a pressure-deflection curve and the residual stress in the film. Prior art FIG. 2 shows the vertical equilibrium of film 1 when pressure is applied via cavity 3.

The stress state of film 1 is two dimensional so that properties in the plane of film 1 are measured through the use of known equations which include as parameter(s) the geometry of the film, the properties of the material composing the film, the differential pressure applied across the film, the center deflection of the film, and in-plane residual stress. For example, see "Mechanical Properties of Thin Films" by Nix, found in the 1988 Institute of Metals Lecture, Volume 20A, November 1989; "Measuring the Mechanical Properties of Thin Metal Films by Means of Bulge Testing of Micromachined Windows" by Paviot, et. al., Mat. Res. Soc. Symp. Proc. Vol. 356, 1995 Materials Research Society; "Mechanical Behavior of Thin Films" by Vinci and Vlassak, Annu. Rev. Mater. Sci. 1996-26:431–62; "The In-Situ Measurement of Mechanical Properties of Multi-Layer Coating" by Lin, 1990 MIT Dept. of Mat. Sci. & Eng., Archives; "Load Deflection Analysis for Determining Mechanical Properties of Thin Films With Tensile and Compressive Residual Stresses" by Bulsara, 1995 MIT Dept. Mat'l. Sci. & Eng.; and "New Experimental Techniques and Analysis Methods for the Study of the Mech. Prop. of Materials in Small Volumes", Chapt. 3, by Vlassak (1994), the disclosures of which are all hereby incorporated herein by reference.

Bulge testing of circular or square freestanding windows of different geometries of film 1 mounted to structure 5 allows one to determine the biaxial modulus of the film as well as the residual stress in the film. Knowledge of these characteristics is important in determining durability and other mechanical and structural characteristics of the film.

With regard to square films or membranes, for example, the elastic deflection as a result of a uniform pressure "p" applied in the cavity is known to be approximately described by the following equation (see Paviot, et. al. referenced above):

$$p = c_1(v)\frac{Et}{(1-v)a^4}w_0^3 + c_2\frac{\sigma_{res}t}{a^2}w_o$$

where $c_1(v)$ is about $1/(0.792+0.085\,v)^3$ and $c_2$ equals about 3.393. In this expression, $w_0$ is the deflection of the center of the film or membrane, "t" is the film or membrane thickness, and "a" is the width of the membrane. Utilizing the above-identified equation enables one to determine the biaxial modulus $Y=E/(1-v)$ and the residual stress in the film.

As disclosed in Vinci and Vlassak (cited above), the pressure-deflection relationship for a thin circular film or membrane with a residual stress in a bulge test is approximated by the equation:

$$P = (1-0.241v)\left(\frac{8}{3}\right)\left(\frac{E}{1-v}\right)\left(\frac{t}{a^4}\right)w_0^3 + 4\left(\frac{\sigma_0 t}{a^2}\right)w_0$$

in the elastic regime, where $w_0$ is the deflection of the center of the film or membrane, "P" is the applied pressure, "t" is the film or membrane thickness, and "a" is the film or membrane radius. Using this equation enables one to determine the biaxial modulus $E/(1-v)$ and the residual stress in the film.

It is noted that other equations, which are disclosed and explained in the above-identified publications, may be used to determine residual stress and/or elastic modulus of films subjected to bulge testing.

It is also known to test composite membranes including two or more layers. For example, see pages 90+ in Chapter 3 of Vlassak, "New Experimental Techniques and Analysis Methods for the Study of the Mechanical Properties of Materials in Small Volumes" (1994), where bulge testing of a composite membrane including two or more layers is discussed. As discussed by Vlassak, silicon oxide or silicon nitride films can be used as substrates or membranes onto which metal films are deposited. This technique can be applied to a variety of films without major changes to the sample preparation method.

Still referring to Chapter 3 of Vlassak, pages 90+, it is known that the residual stress in, and elastic properties of, the silicon nitride or silicon oxide membrane by itself can be determined by bulge testing the membrane without a film overlayer. Thereafter, when a metal overlayer film is deposited onto the silicon oxide or silicon nitride membrane, its biaxial modulus can be calculated from the biaxial modulus of the composite film. If Poisson's ratio of the metal film is known, Young's modulus of the metal film can be calculated from the biaxial or plane-strain modulus. The residual stress in the metal film is calculated via the average residual stress in the composite, as the weighted average of the stresses in the membrane and the metal film overlayer.

As discussed in section 3.4 of Vlassak, Chapter 3, it is known to fabricate freestanding silicon nitride films on silicon substrates by way of micromachining. Such silicon nitride membranes are then used as substrates or membranes for other films (e.g. metal films) and the resulting composite film is bulge tested. Referring to prior art FIGS. 3(a)–3(f), known steps are shown in a sample preparation process. As illustrated in FIGS. 3(a) and 3(b), silicon nitride films 7 with residual tensile stress are deposited by LPCVD on both sides of wafer 9. Using mask 11 illustrated in FIG. 3(c), a window is etched in silicon nitride film 7 on the backside of the wafer by way of lithography and reactive ion/plasma etching. The etched window is illustrated in FIG. 3(d). Thereafter, as shown in FIG. 3(e), silicon 9 exposed by the previously etched window is etched using, for example, an etchant including potassium hydroxide. FIG. 3(e) illustrates the final silicon membrane wafer structure with a freestanding flexible silicon nitride membrane over the cavity on its top surface. The freestanding flexible membrane portion of layer 7 in FIGS. 3(e)–3(f) is defined within the silicon shoulder area, where film 7 is susceptible to bulging. Finally, as illustrated in FIG. 3(f), a thin metal film 13 to be bulge tested is evaporated onto the top surface of the membrane structure.

After the FIG. 3(f) structure is made, as disclosed by Vlassak, it is bulge tested using the prior art FIG. 4 apparatus, which includes mounting structure 15 upon which composite sample member 17 to be bulge tested is mounted, pump 19, pressure gauge 21, computer and data acquisition terminal 23, and an inspection system for detecting deflection of film 17. The inspection system including laser 25, beamsplitter 27, collimator 29, lens 31, reflective mirror 33, density filter 35, reference mirror 37, and screen 39 with an interference pattern. As described by Vlassak, sample 17 to be tested is glued onto mounting structure 15 and pressure is applied to the lower side of sample 17 by pumping water into cavity 41 via pump 19. The inspection system then measures the deflection of sample 17 caused by the water pressure in the cavity. The result is a pressure versus deflection plot for the sample. From this plot, the elastic modulus and residual stress of overlying film 13 can be determined.

U.S. Pat. No. 4,735,092 to Kenny, discloses a rupture testing apparatus for classifying or grading metal foils. Gas under pressure is admitted to a platen and the unsupported part of the sample bulges outwardly until the sample ruptures. A plot is made of samples for temperature, burst pressure, and bulge height at burst, with the results being used to grade or classify the foil. Unfortunately, the '092 patent suffers from a number of problems, including the inability to efficiently and properly determine stress and/or modulus characteristics of the film being bulge tested. For example, the dial micrometer transducer includes a probe or arm which extends downward to contact the film being bulge tested. Contacting type transducers are generally undesirable, especially in view of the fragile nature of many samples that must be tested. Further deficiencies in the '092 system are discussed below.

While the above-referenced prior art bulge testing techniques and disclosures achieve satisfactory results in non-commercial environments where cost and efficiency are not critical considerations, they unfortunately have their limitations. A few of these limitations are discussed below.

The characteristics and properties of films, coating, and layers used in electronic arrays, wear surfaces, circuits, cutting tools, and the like are becoming more and more important. Different systems and techniques are utilized to deposit and/or pattern thin films on substrates. For example, a uniform thin film indium tin oxide (ITO) layer a few hundred Å thick may be deposited across an entire substrate, and thereafter sometimes patterned via conventional methods into a plurality of electrode segments. Due to the techniques and systems used to deposit and/or pattern such thin films, it is not surprising that areas of the thin film(s) on the substrate, or certain patterned electrodes in the array, may have different residual stress and modulus characteristics than others. For example, film near an edge of the substrate may have different stress characteristics than near the center of the substrate, due to the techniques and systems utilized in the deposition, fabrication, and/or patterning. For example, a continuous film may have different residual stress and/or elastic modulus characteristics in different areas on the substrate. Differences such as these in large area substrate or array-type applications cannot be detected by the prior art bulge testing systems discussed above.

Bulge testing has been minimally successful at best, for reasons such as high substrate/membrane costs, the inability to commercially manufacture scores of reproducible substrates/membranes within limited predetermined dimensional and compositional tolerances (i.e. very difficult and expensive to make substrates of constant dimensions which all have the same characteristics), inaccurate substrates/membranes, inability to test large area films, and the like.

There also exists a need in the art for reproducible circular, rather than square, membranes to allow analytical equations to be used to calculate thin film mechanical properties from pressure-deflection data rather than having to use numerical methods. Also, a need exists for membrane material having reproducible mechanical properties in contrast to currently produced silicon nitride or silicon oxide whose mechanical properties vary as a function of deposition/growth parameters, and equipment used to manufacture same.

It is apparent from the above that there exists a need in the art for a bulge testing system that can be utilized to test large area thin films (or portions thereof) on substrates, and thin film segments as they are deposited in array form on a substrate. There is also a need in the art for a way in which to fabricate supporting substrates/membranes so that on a continuous basis all such supporting membranes are fairly identical, with their geometries, mechanical responses, and/or material properties being substantially the same. Therefore, in a commercial bulge testing environment, it would be desirable if there were no need to separately bulge test each membrane structure and determine its characteristics prior to applying thereto a thin film to be tested. The ability to mass produce many such uniform supporting membranes would result in increased efficiency and significant cost savings in commercial testing environments. There also exists a need in the art for an improved membrane structure for supporting thin films to be bulge tested. Other needs include the need for precision mounting of membranes, automated measurement, improved deflection detection techniques, and improved software for manipulating the table or platform upon which the membrane structure is mounted.

It is a purpose of this invention to fulfill the above-described needs in the art, as well as other needs which will become apparent to the skilled artisan from the following detailed description of this invention.

SUMMARY OF THE INVENTION

Generally speaking, this invention fulfills the above-described needs in the art by providing a method of manufacturing a plurality of membrane structures for use in bulge testing so that a majority of the manufactured membrane structures include freestanding portions having substantially the same thickness, substantially the same in-plane geometry (e.g. diameter), and substantially the same response, the method comprising the steps:

selecting at least one material to be utilized in the manufacture of the membrane structures;

forming portions of the at least one material into a plurality of membrane structures, each of the membrane structures including at least one cavity and at least one freestanding thin film portion located over the cavity and defining a surface of the cavity; and using manufacturing techniques to manufacture each of the membrane structures so that at least about 85% (preferably at least about 95%) of the resulting membrane structures have identical freestanding thin film portion geometries including (1) in-plane diameters, and/or (2) thicknesses, within about ±5% (preferably within about ±3%, and most preferably within about ±1%), thereby enabling commercial bulge testing to be more efficiently undertaken. The freestanding membrane portions are preferably circular in shape (as viewed from above), but also may be other shapes such as rectangular, oval, etc.

This invention further fulfills the above-described needs in the art by providing a structure for use in bulge testing of films, the structure comprising:

a membrane structure including a plurality of cavities defined therein; and a plurality of freestanding portions capable of bulging, each of the freestanding portions corresponding to at least one of the cavities, so that each of the freestanding portions defines part of a corresponding one of the cavities, and wherein each of the freestanding portions is adapted to receive thereon a film (e.g. thin metal film, thin ceramic film, thin paint coating, thin polymer film/resist, etc.) to be bulge tested.

According to certain preferred embodiments, the film to be bulge tested is preferably a thin film and may include one of a thin metal film, a thin ceramic film, a polymer thin film, a coating, and a layer, and wherein the film to be bulge tested is from about 100 Å to 500,000 Å thick (preferably from about 100 Å to 50,000 Å thick, and most preferably from about 500 Å to 5,000 Å thick).

This invention further fulfills the above-described needs in the art by providing an apparatus for bulge testing films, the apparatus comprising:

a mounting structure including an upper surface and a cavity defined therein;

means for positioning a film to be bulge tested on the upper surface over top of the cavity;

an optical transducer for measuring deflection or bulging of the film proximate the cavity in a non-contacting manner, wherein the transducer is one of a white light interferometer and a laser triangulation transducer; and means for determining stress and modulus properties of the film based upon measurements taken by the transducer.

In certain preferred embodiments, an opaque film is provided on top of the film to be bulge tested or under the freestanding membrane portion, in order to enable the transducer to more accurately and efficiently detect deflection or bulging of the film to be bulge tested and the underlying freestanding membrane portion.

This invention further fulfills the above-described needs in the art by providing a method of bulge testing a thin film, the method comprising the steps of:

providing a bulge testing apparatus including a major surface and a cavity defined therein;

providing a thin film on the major surface over top of the cavity;

locating a center point on the thin film, the center point overlying approximately the center of the cavity;

locating first and second points spaced from the center point, so that a line connecting the first and second points, and the center point, substantially bisects or otherwise crosses a portion of the thin film overlying the cavity; and optically measuring bulging or deflection of the thin film by measuring deflection of the center point relative to the first and second points which are positioned at undeflected locations.

This invention further fulfills the above-described needs in the art by providing a method of bulge testing a film at a plurality of different locations, the method comprising the steps of:

providing a bulge testing apparatus including a major surface and a cavity defined therein;

providing a film on the major surface over top of the cavities;

evacuating the cavity so as to cause the film to deflect inwardly; and measuring the deflection of the film caused by the evacuating, and based upon the measuring determining modulus and stress properties of the film.

This invention further fulfills the above-described needs in the art by providing a method of bulge testing a film, the method comprising the steps of:

providing a bulge testing apparatus including a major surface and a cavity defined therein;

providing a film on the major surface over top of the cavities;

allowing the film to bulge, either inwardly or outwardly, as a result of inherent pre-stress present in the film, without pressurizing or evacuating the cavity; and measuring bulging or deflection of the film caused by the pre-stress, so that it is unnecessary to either pressurize or evacuate the cavity in order to bulge test the film.

In certain preferred embodiments, a lookup table is stored in the system which enables the system to determine, via the lookup table, the residual stress of a film being tested in view of the film's measured deflection, thickness, material, and the pressure applied in the cavity. The look-up table may utilize finite element analysis (FEA) to perform these functions.

Still further, this invention fulfills the above-described needs in the art by providing numerous specific methods for manufacturing membrane structures, which are discussed below.

This invention will now be described with reference to certain embodiments thereof as illustrated in the following drawings.

IN THE DRAWINGS

Prior art FIG. 1 is a side elevational view illustrating a thin film attached to a mounting structure being deflected upwardly under the influence of pressure during a bulge test.

Prior art FIG. 2 is a schematic illustrating the vertical equilibrium of the film being tested in FIG. 1.

Prior art FIGS. 3(a)–3(f) are side cross-sectional views illustrating the manufacture of a membrane structure adapted to receive a thin film to be bulge tested.

Prior art FIG. 4 is a schematic illustration of a known bulge testing apparatus and system.

FIGS. 6(a)–6(c) are side partial cross-sectional views illustrating how a membrane structure is manufactured according to an anodic bonding embodiment of this invention.

FIGS. 7(a)–7(f) are side partial cross-sectional views illustrating how a membrane structure is manufactured according to another embodiment of this invention, which utilizes a single crystal silicon wafer and double diffusion of a vertically structured etch-stop into the substrate or wafer, and a chemical etch.

FIGS. 8(a)–8(e) are side partial cross-sectional views illustrating a method of manufacture of a membrane structure according to yet another embodiment of this invention, utilizing a SIMOX wafer (or SOI—silicon on insulator, wafer), and deep vertical etch.

FIGS. 9(a)–9(d) are side partial cross-sectional views illustrating the manufacture of a membrane structure according to still another embodiment of this invention, utilizing both a SIMOX (or SOI) wafer and anodic bonding.

FIGS. 10(a)–10(e) are side partial cross-sectional views illustrating a method of manufacturing a membrane structure according to another embodiment of this invention, utilizing both anodic bonding and a single crystal silicon etched wafer.

Figure 11:
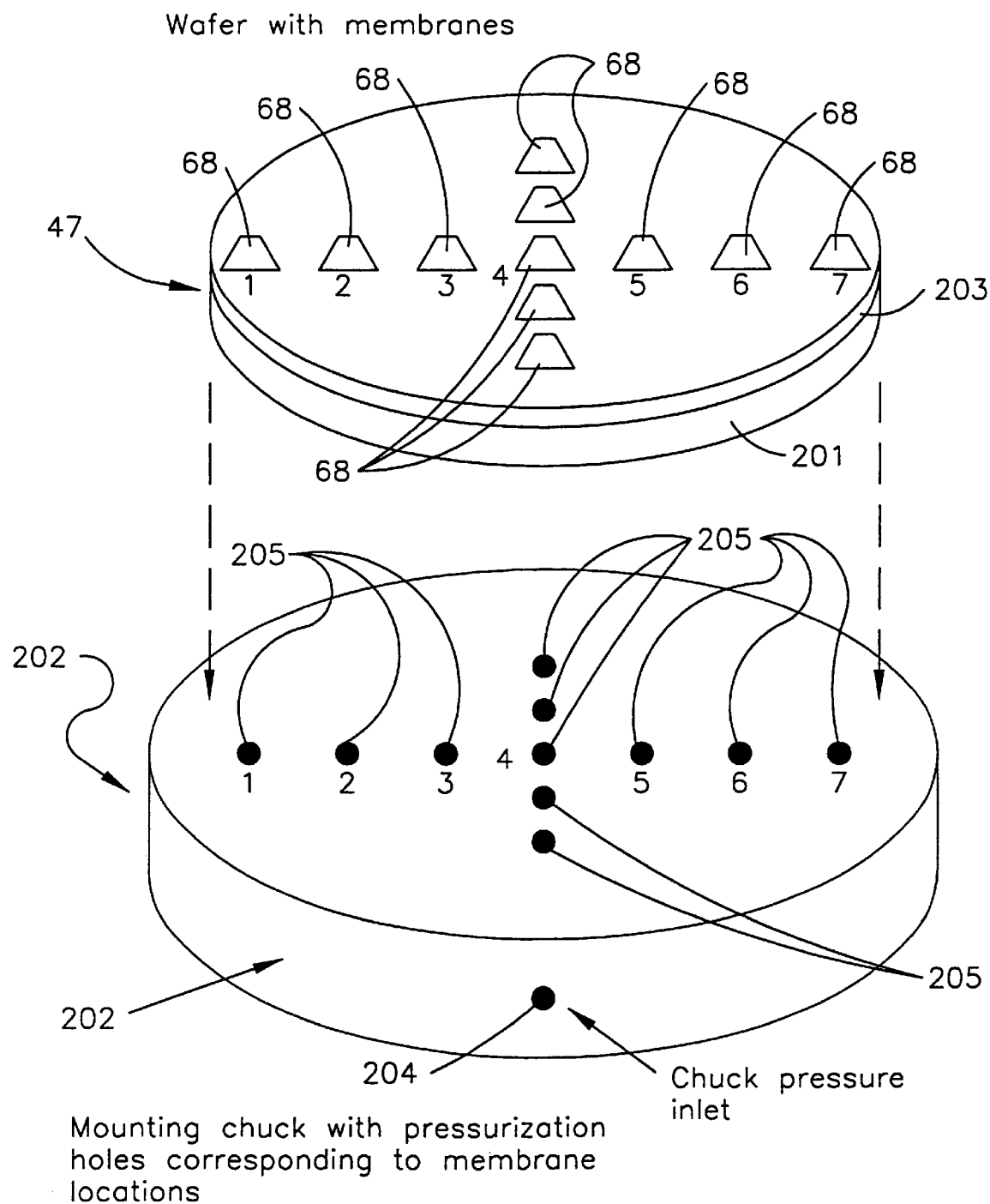

FIG. 11 is an exploded perspective view illustrating a large area membrane structure and corresponding mounting chuck according to an embodiment of this invention, this membrane structure including an array of separate and independent flexible freestanding membrane portions which allow the physical/mechanical properties of a film(s) to be tested across substantially the entire surface/array of the membrane structure, or a portion thereof.

Figure 12:
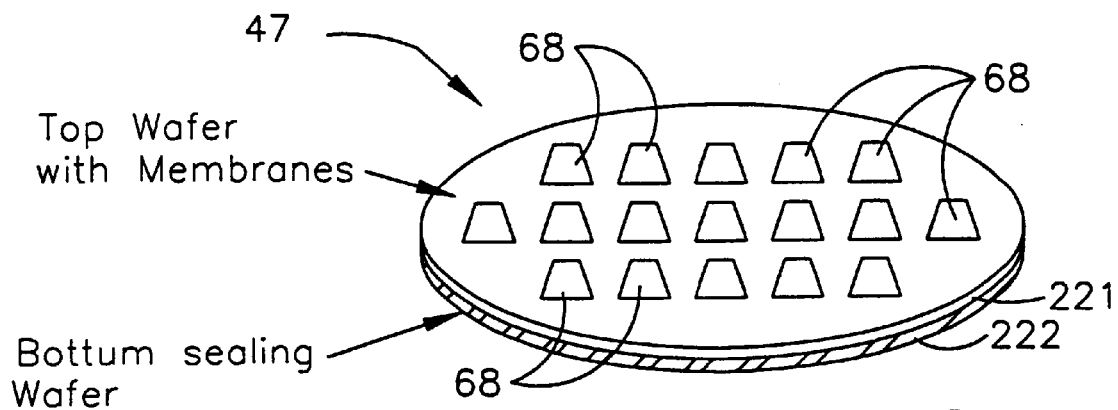

FIG. 12 is a perspective view illustrating a membrane structure according to an embodiment of this invention which is similar to the FIG. 11 embodiment, except that a different number and arrangement of freestanding flexible membrane portions are provided, and the method of mounting and pressurizing the membranes is different.

Figure 13:
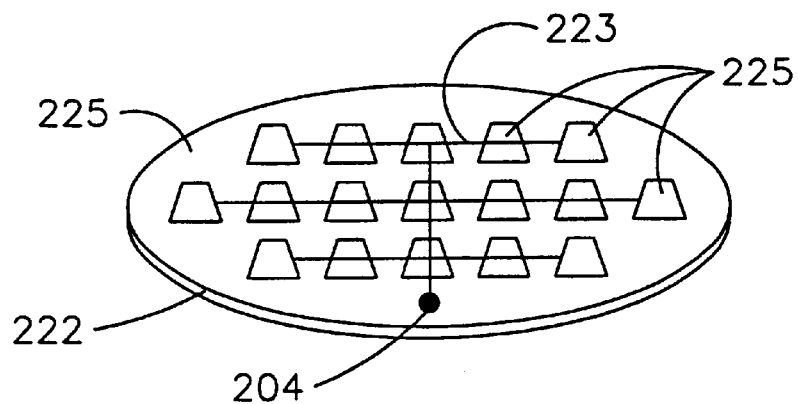
Figure 14:
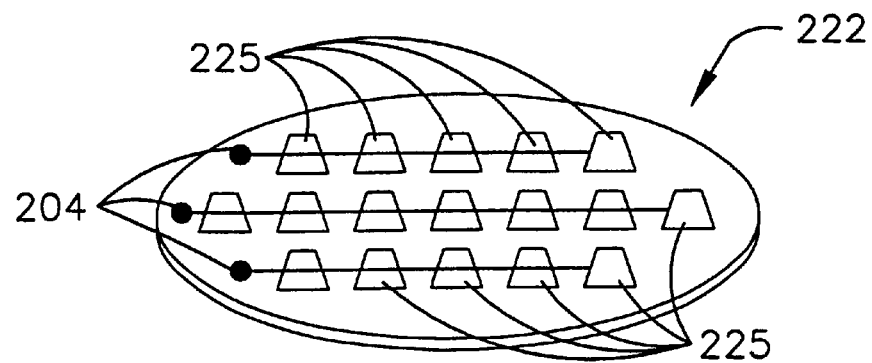

FIGS. 13 and 14 are perspective views illustrating different channel arrangements for use with the bottom wafer of the FIG. 12 membrane array structure.

Figure 15:
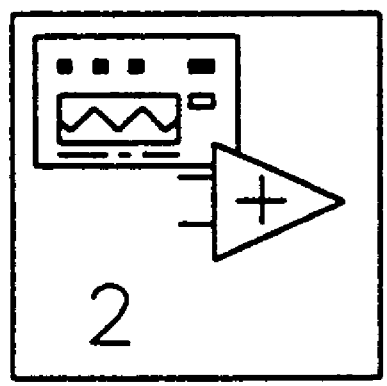
Figure 20:
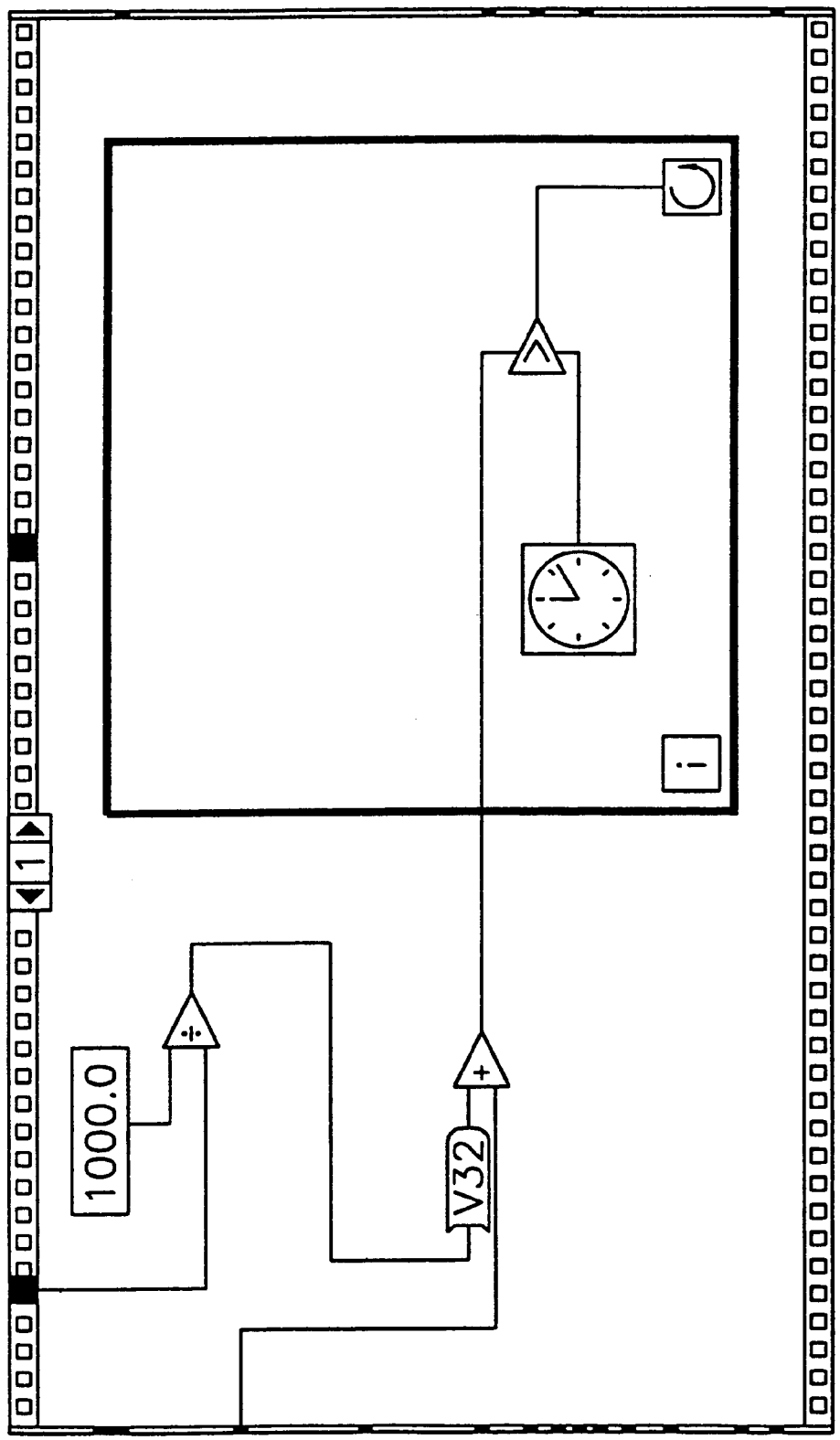
Figure 20A:
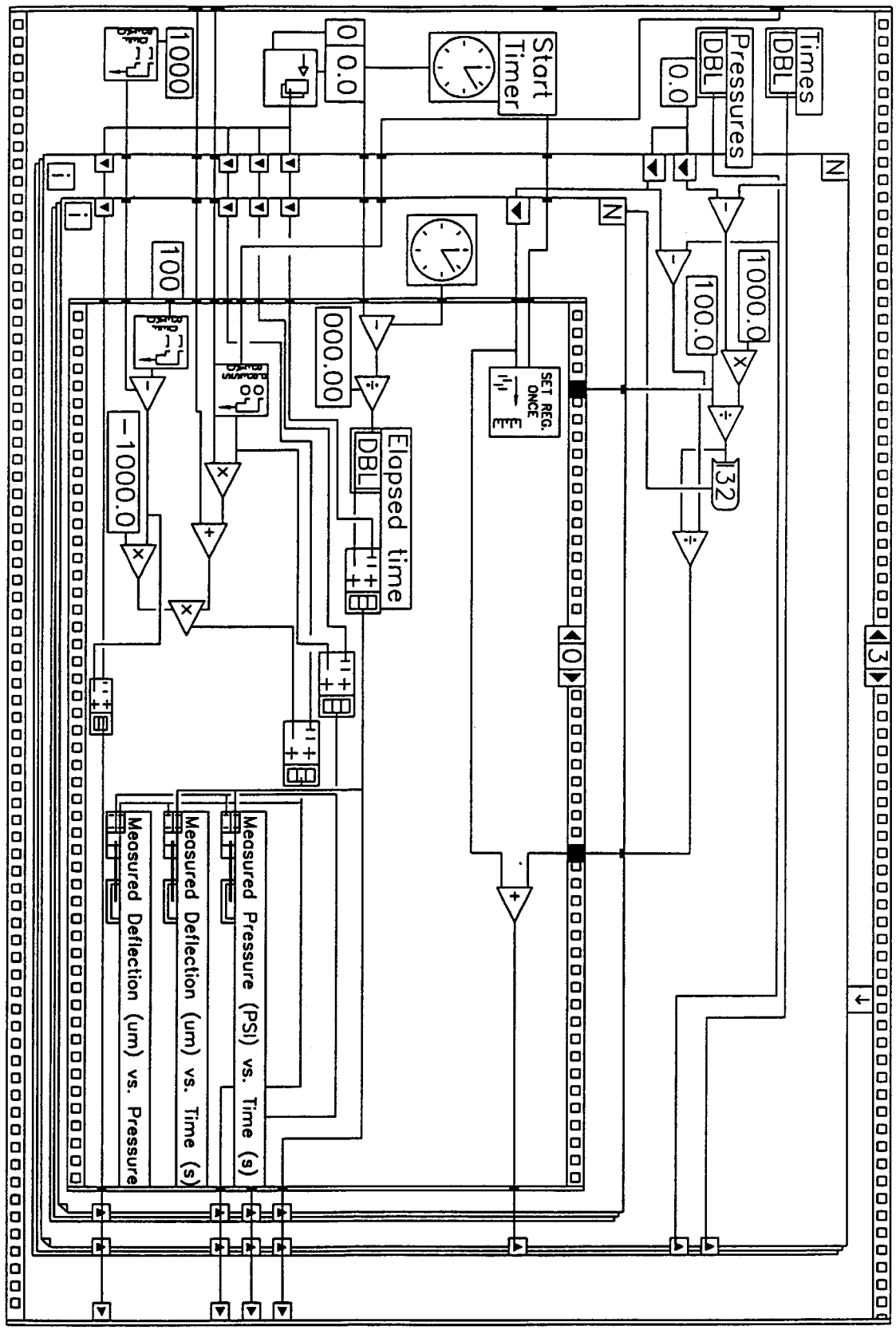
Figure 20B:
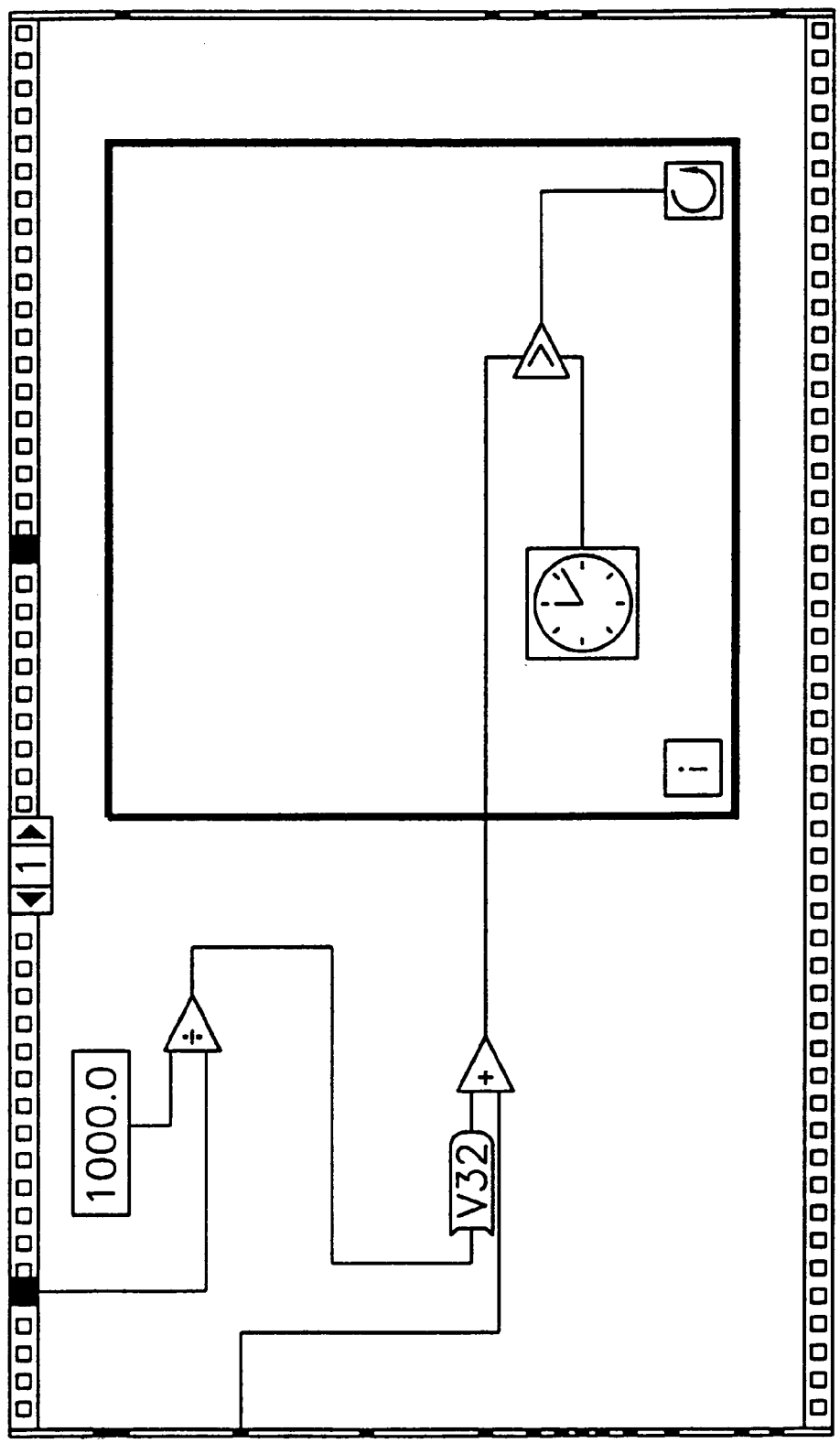
Figure 23:
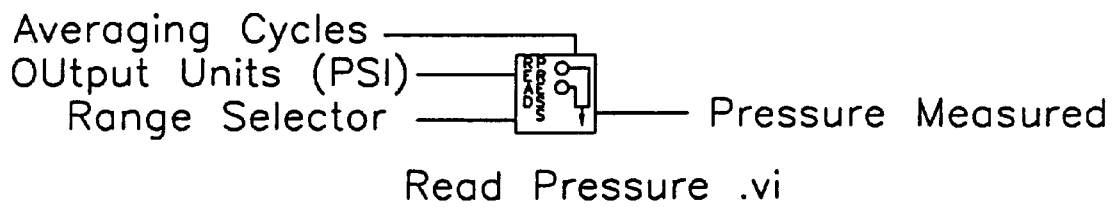
Figure 24:
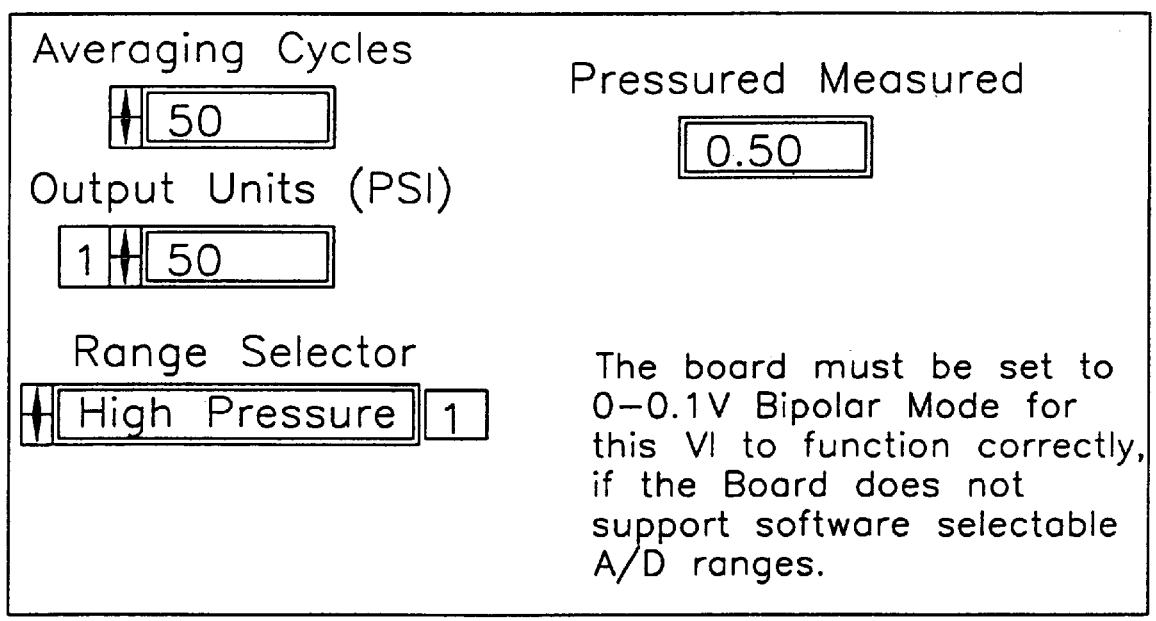
Figure 27:
Figure 28:
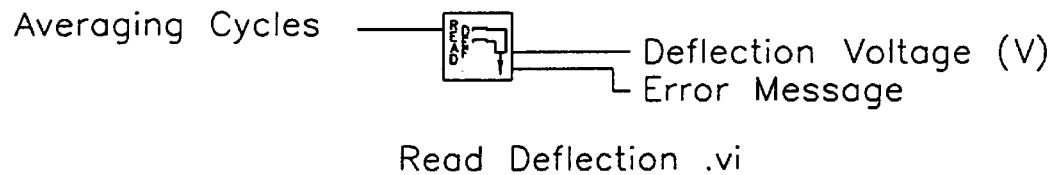
Figure 29:
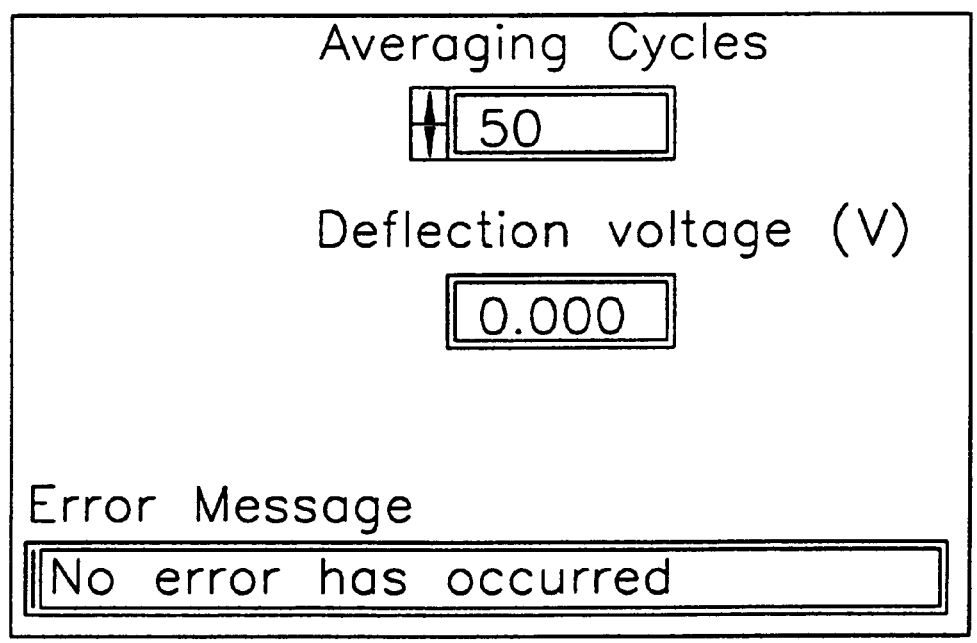
Figure 32:
Figure 33:
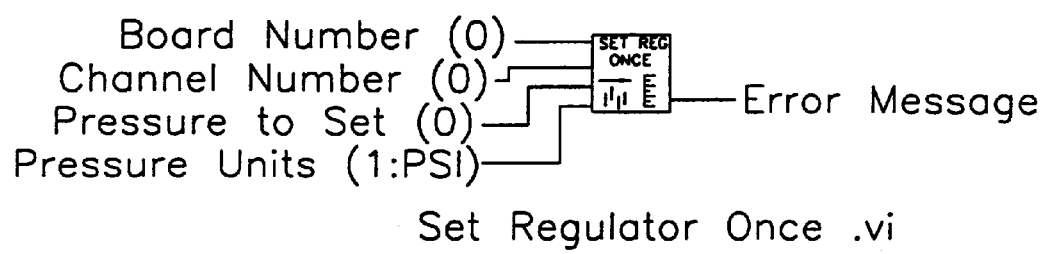
Figure 34:
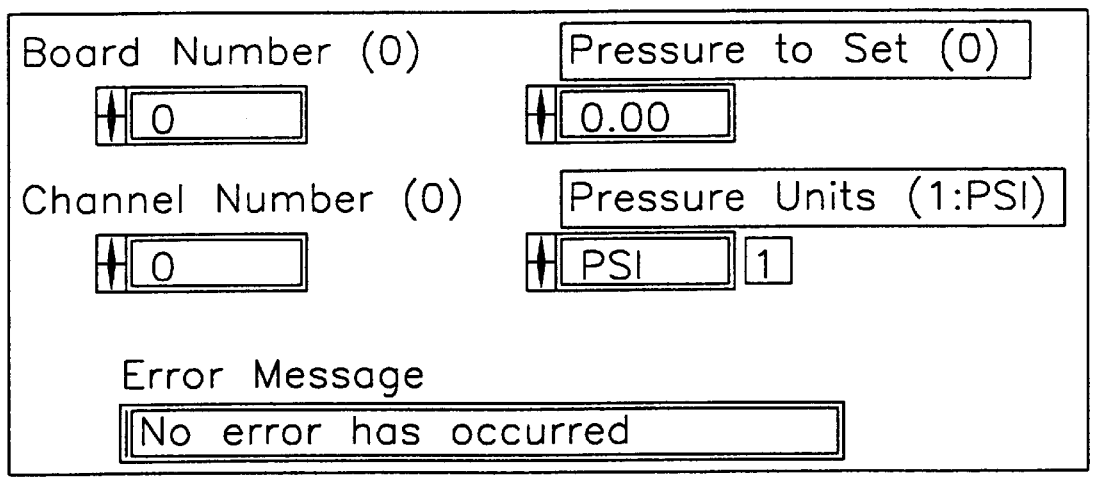
Figure 36:
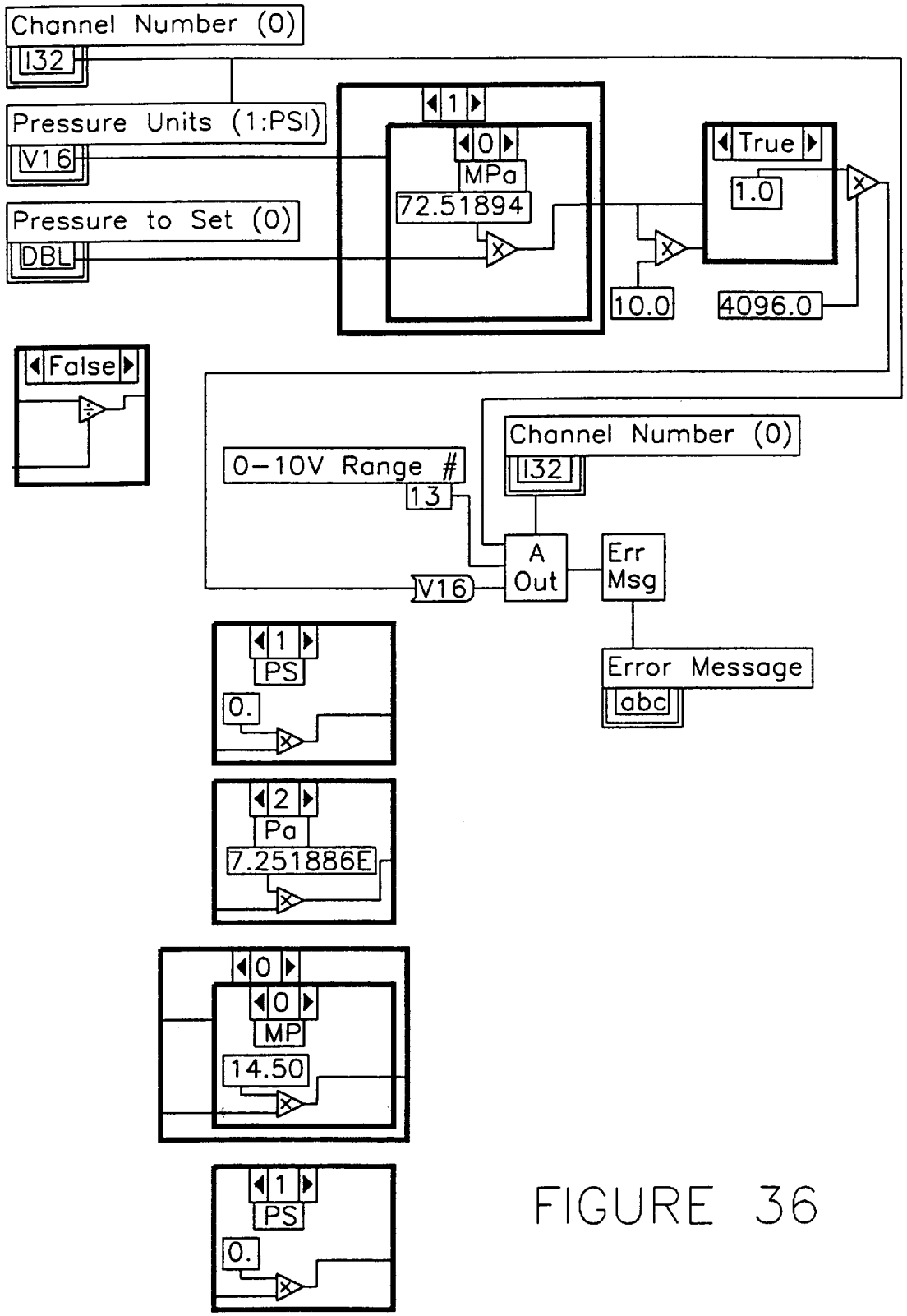
Figure 39:
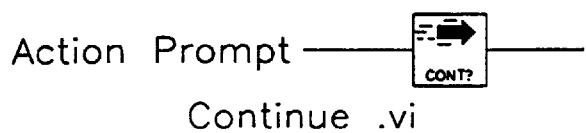
Figure 40:
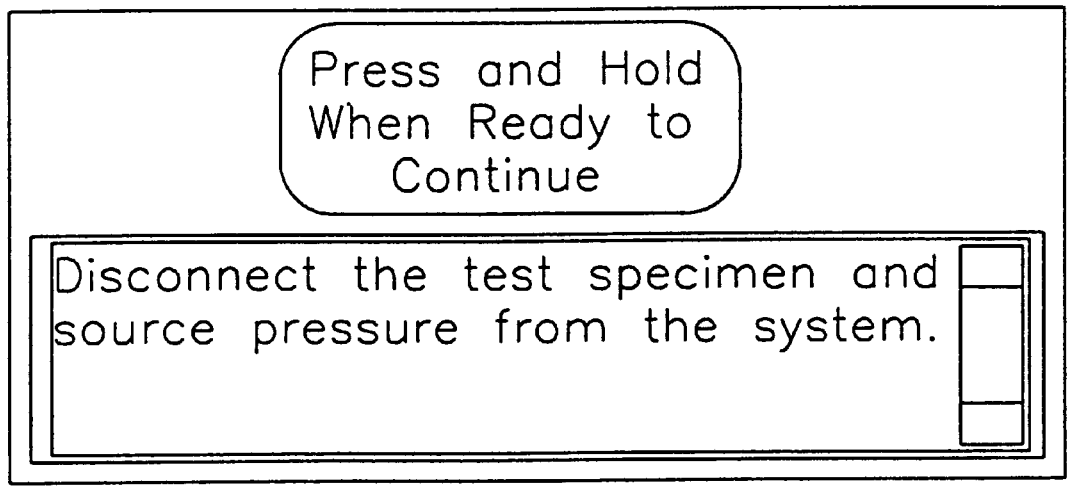
Figure 41:
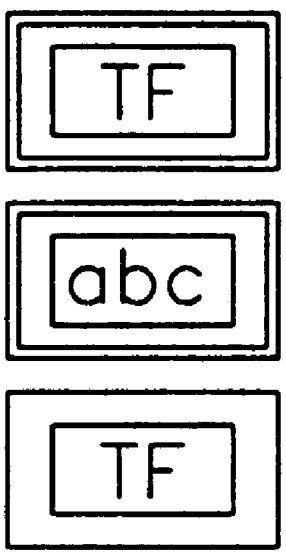
Figure 42:
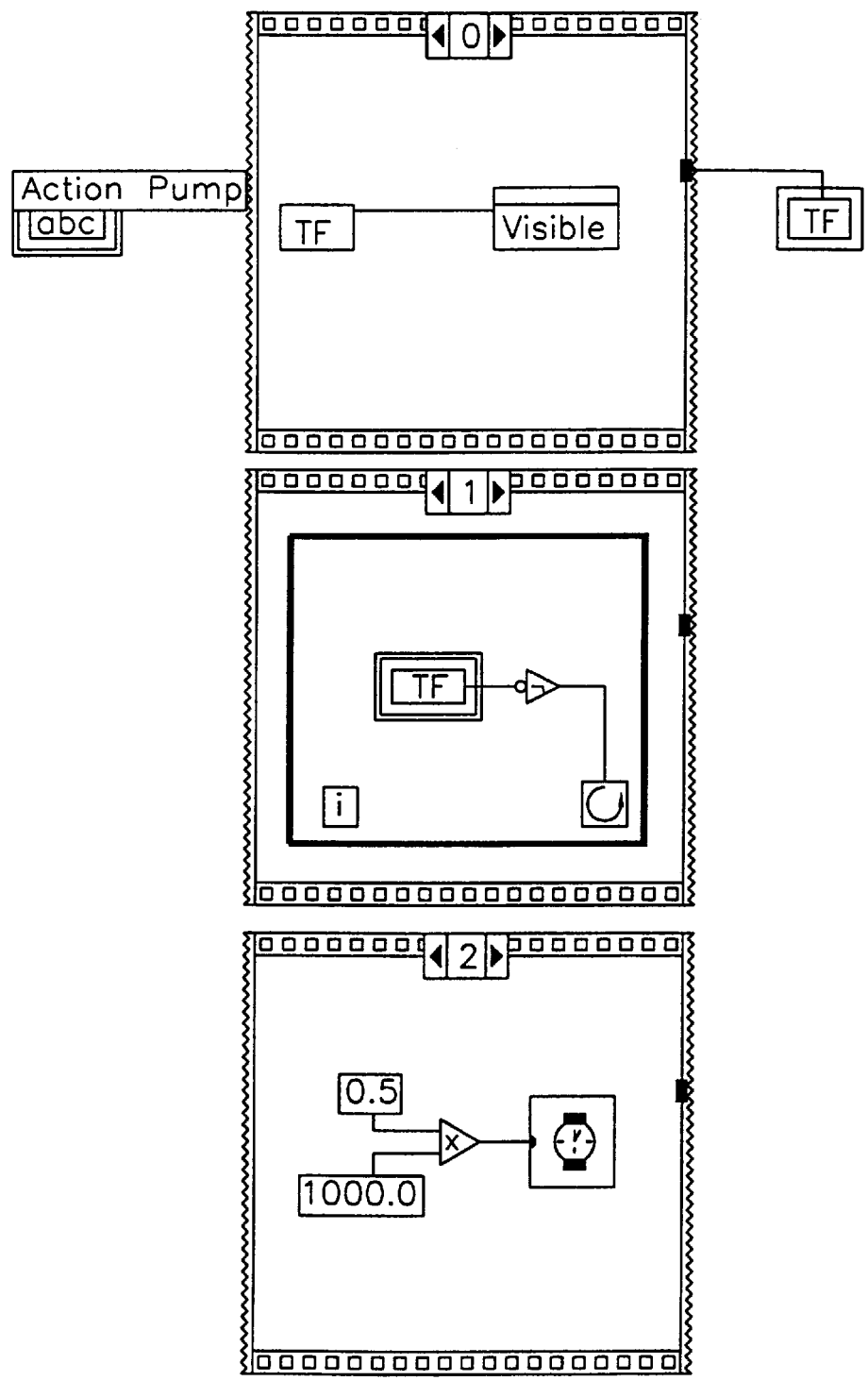
Figure 45:
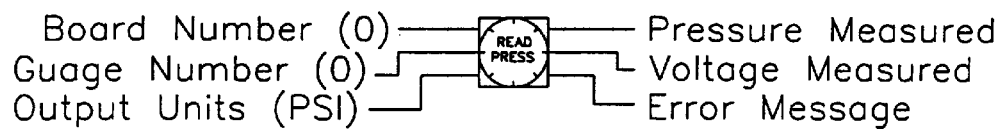
Figure 46:
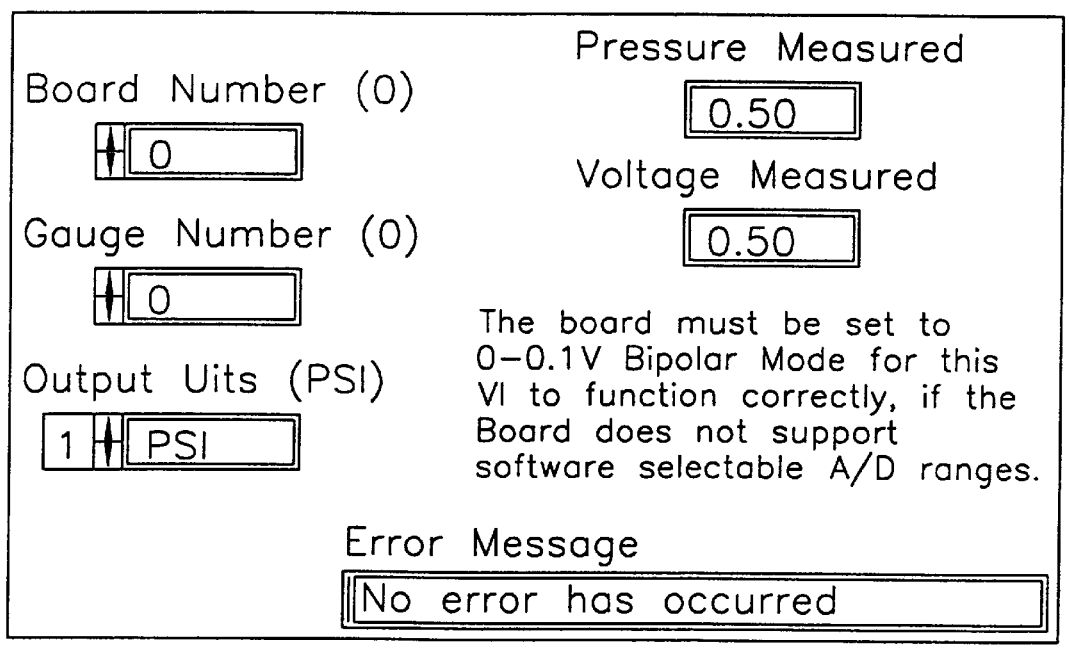
Figure 48:
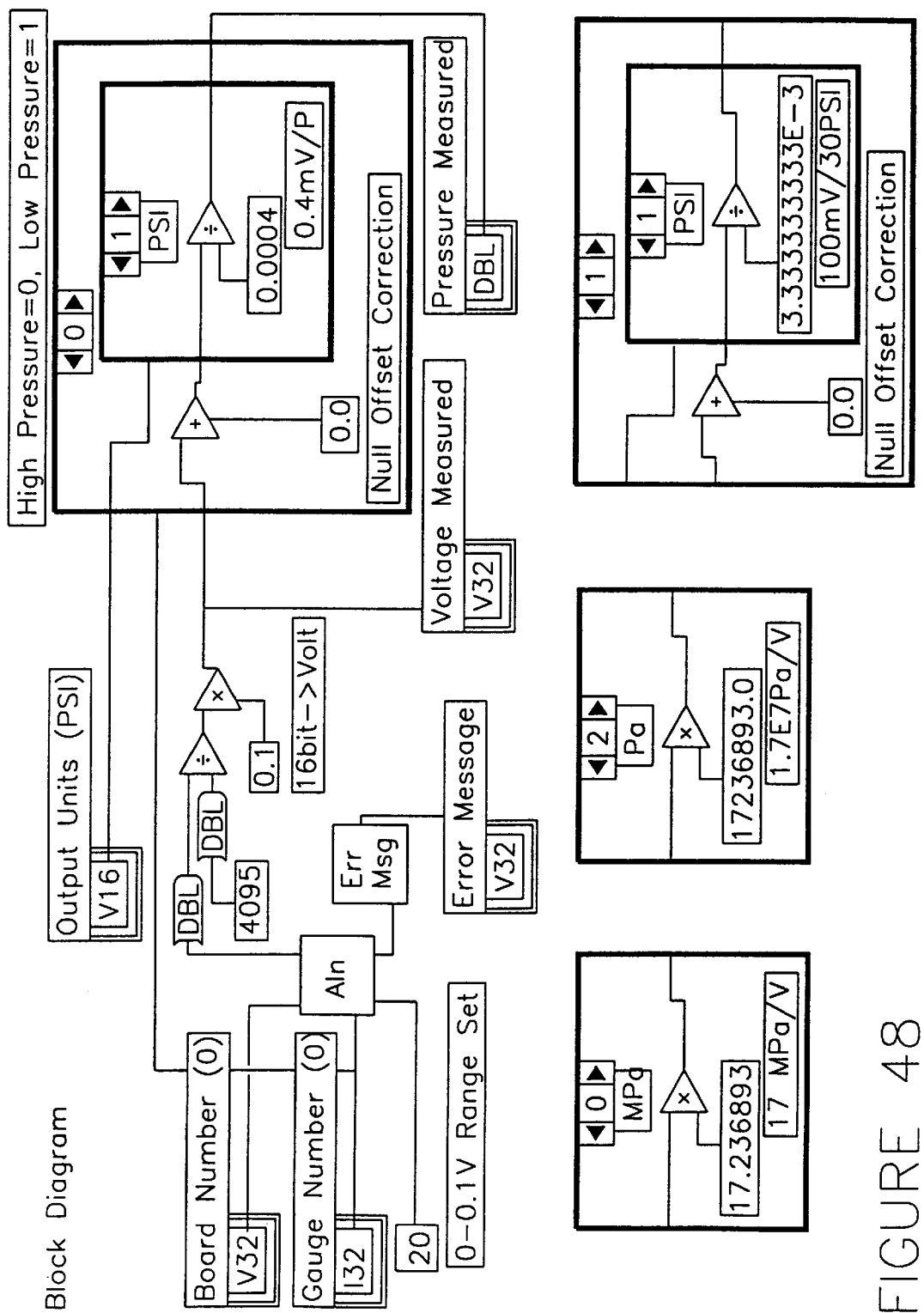
Figure 51:
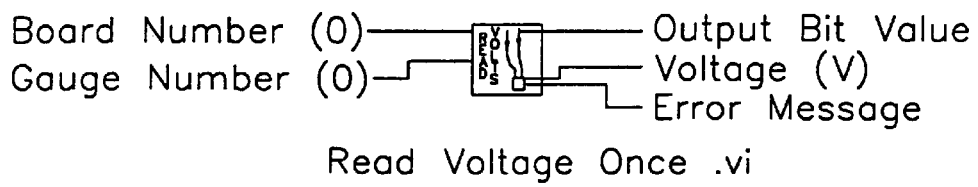
Figure 56:
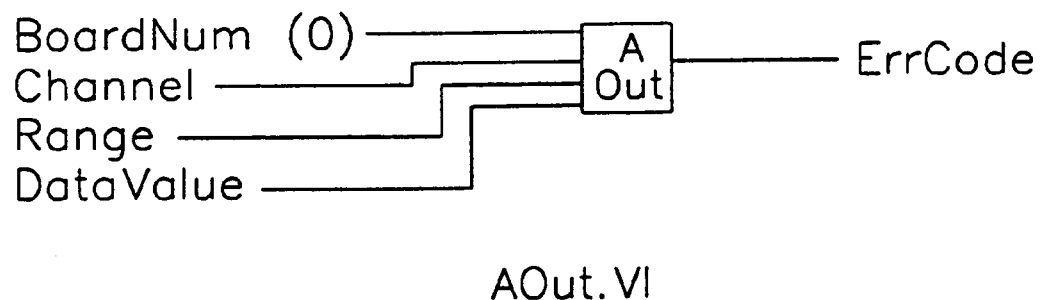
Figure 57:
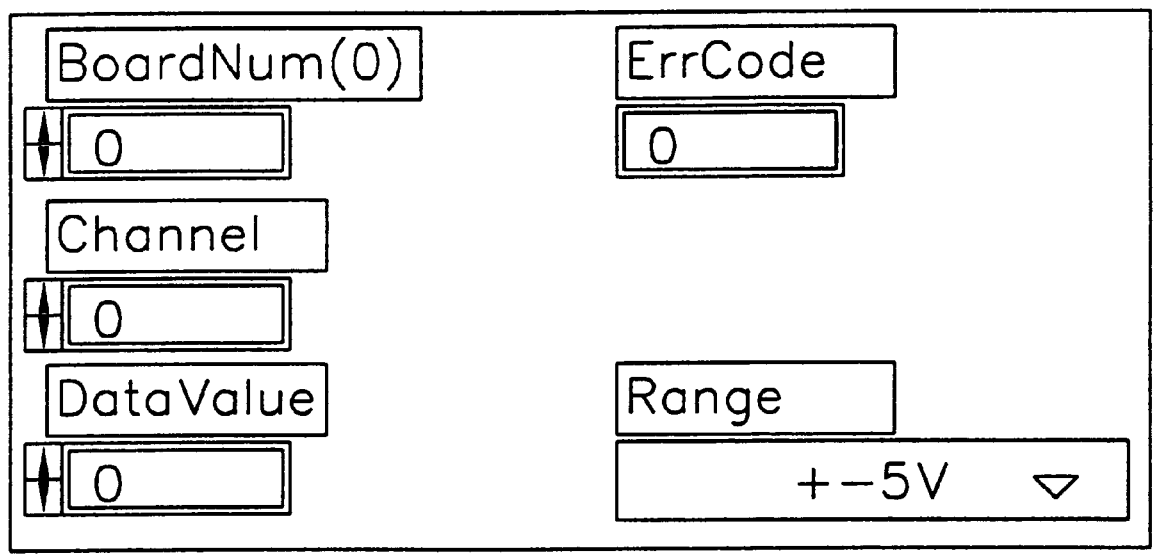
Figure 61:
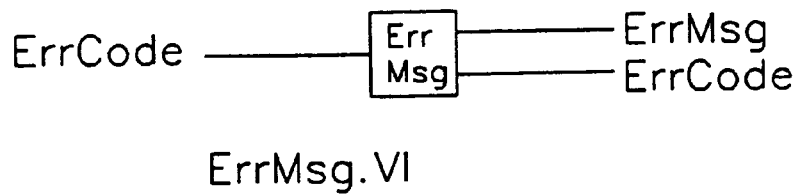
Figure 62:
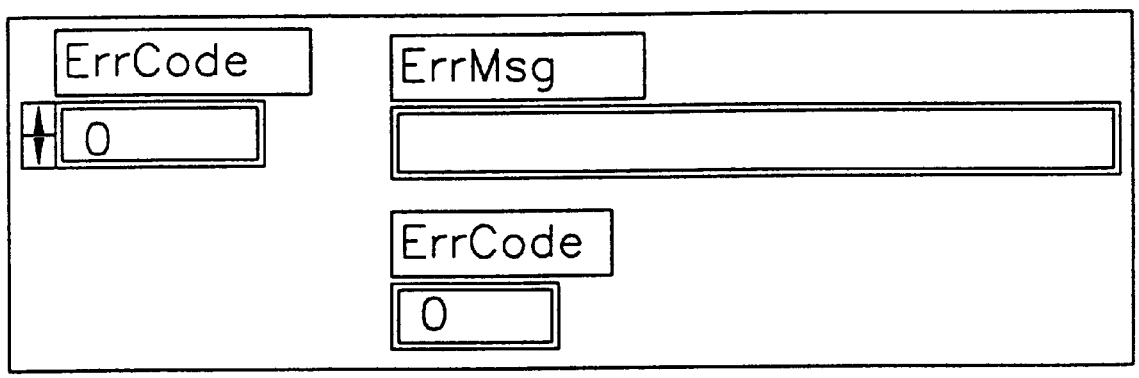
Figure 66:
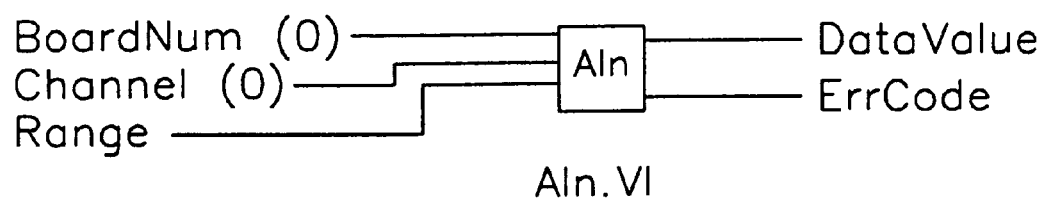
Figure 67:
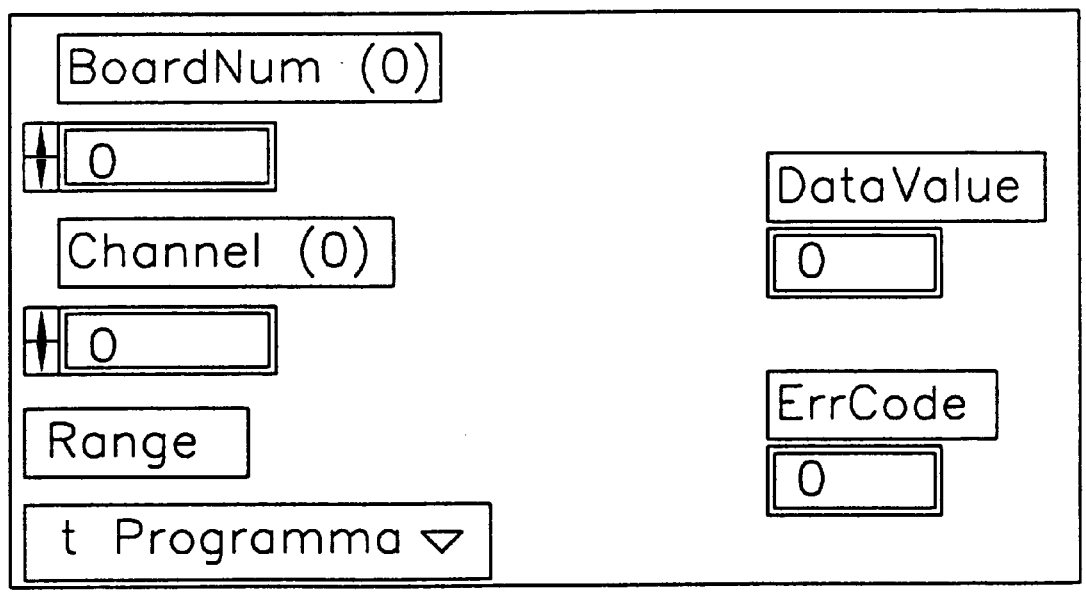

FIGS. 15–70 are schematic illustrations of system requirements for computer code used in bulge testing systems herein, according to an embodiment of this invention. These illustrations may be used by any experienced LabView programmer to develop preferred functionality and user interface for the systems herein. The software, may be written under LabVIEW Version 3.1 (National Instruments Corp.) running on MS Windows 3.1. It typically requires at least a 33 MHz or faster 486DX class machine for consistent reliable operation. It has been run on a 486DX/2 machine running at 66 MHz. Typically, RAM of at least 8 Megabytes is needed, while conservative disk space requirements start at about 5 Megabytes, depending on the duration of tests and the data storage mode selected. The acquisition and control routines typically need a Computer Boards Corp. data acquisition board and the associated Universal Library Software with LabVIEW extensions. The data acquisition and control algorithms are based on LabVIEW from National Instruments Corp. In contrast to the text-based languages such as FORTRAN or C, the graphical programming language called "G" uses block diagrams to generate applications. The appended documentation of FIGS. 15–70 of connector panes, front panels, controls and indicators, block diagrams, position in hierarchy, and sub VIs may be used by skilled "G" programmers, without undue experimentation, to duplicate the functionality and interface of the bulge test data acquisition and control software in preferred embodiments.

DETAILED DESCRIPTION OF CERTAIN EMBODIMENTS OF THIS INVENTION

Referring now more particularly to the accompanying drawings in which like reference numerals indicate like parts throughout the several views.

Set forth below, and in the drawings, are numerous embodiments of our inventions which relate to bulge testing techniques, test products, test techniques, and methods of making and carrying out same. Bulge testing of films (including coatings and layers) such as those composed of metals (e.g. Ni, Cu, Ag, gold, aluminum, etc.), paint, dielectric thin films, organic compounds or polymers (e.g. photoresist), hard coatings, ceramics (e.g. ITO, silicon nitride, silicon carbide, etc.), and/or the like, is a way in which to measure the films mechanical properties, in certain embodiments in situ. The supporting membrane may be made, in certain embodiments, of any suitable material such as those discussed above, but it is preferable that the membrane is of a material that is residual-stress free, easily characterized, and easily made, such as, but not limited to, semiconductor grade single crystal silicon.

As pressure is applied to one side of a suspended thin film 57, disposed on a freestanding portion 68 of a membrane structure 47 in certain embodiments, the deflection of film 57 is measured as a function of the applied pressure in cavity 53. Behavioral characteristics of film 57 are a function of pressure load versus its deflection. The biaxial modulus and the residual stress of the film being tested can be determined from the relationship between the film's deflection and the applied pressure using known mathematical techniques, as discussed above.

In alternative embodiments of this invention, the deflection of film 57 and/or membrane portion 68 may be caused by pressure evacuation of cavity 53, or even with no pressure or evacuation on either side of the film.

The bulge testing systems herein measure relative deflection of a film 57 or membrane portion 68, with a resolution of better than 0.1 microns and a differential pressure range from about 0.01 to 150 psi (with a pressure resolution (or accuracy) of better than about 0.5% over this range). The preferred pressure applied to one side (top or bottom side) of a sample is from about 0–5 psi. This permits measurement of a number of mechanical material properties, including elastic (e.g. residual stress, biaxial modulus), inelastic (yield strength, rupture strength, adhesion) and time-dependent (creep behavior, relaxation, fatigue, stress corrosion) properties. Additionally, automated measurement is provided, precision of mounting membranes on mounting platforms or chucks is discussed, and array bulge testing capability is described.

In alternative embodiments herein, information regarding the rupture of a membrane or film being tested may be gathered. For example, it can be determined at what point (with regard to deflection and/or pressure) a particular film with a given thickness ruptures.

Stress and Modules

Residual stress is a significant characteristic in predicting mechanical failure or performance of films. Residual stress includes instrinic stress, deposition induced stresses, and stress resulting from mismatches between thermal expansion coefficients of the film and a corresponding substrate. High residual stress can cause cracking and adhesion problems in films, and may also cause shape deformation of coated substrates. Other physical film properties are also affected by residual stress.

Knowledge of elastic moduli of thin films is important for several reasons. Elastic moduli are used to determine stresses in thin films. The elastic moduli provide an indication of the physical structure and composition of the film, for example, whether the film is crystalline or amorphous. Knowledge of the elastic moduli is necessary for any characteristic of a thin film, whether electrical, mechanical, or photonic, that depends on the state of stress and/or strain. One way to determine biaxial moduli of thin films is to measure the pressure/deflection characteristic of the thin film 57, either alone or as deposited on a membrane structure 47. Young's modulus can be obtained from the biaxial modulus by knowledge or estimation of Poisson's ratio.

In bulge testing, when we measure the deflection of a membrane portion and thin film thereon as a function of the pressure applied to one side thereof, we are measuring the stiffness characteristic of the film. Because we know the geometry (e.g. thickness) of the film being tested, the elastic modulus (i.e. Young's modulus) can be extracted. Note the following exemplary equation:

$$\text{Biaxial modulus } (BM) = EM \div (1-v)$$

where "v" is Poisson's ratio, "EM" is the elastic modulus, and "BM" is the biaxial modulus.

Testing Apparatus/Method

Figure 5A:
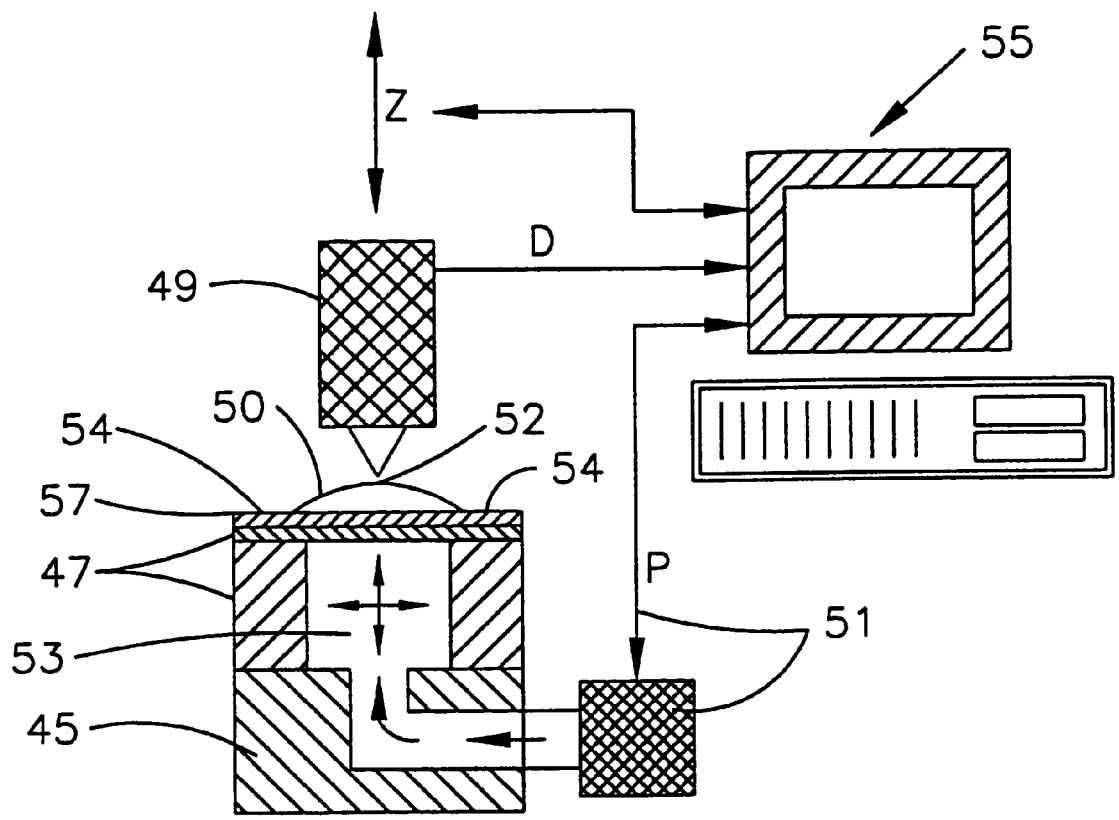
FIG. 5(a) is a schematic illustration of a bulge testing apparatus and system according to certain embodiments of this invention.

FIG. 5(*a*) hereto is a schematic illustration of an overall system used for bulge testing according to certain embodiments of this invention. The system includes mounting/alignment structure 45, membrane structure 47 mounted on supporting structure or chuck 45, thin film 57 to be analyzed disposed on membrane structure 47, transducer 49 for measuring the deflection 50 of the flexible freestanding portion 68 of membrane structure 47 and/or thin film 57 to be tested/analyzed, pressurization system 51 for applying fluid (gaseous or liquid) pressure within cavity 53 and thus to the bottom side of flexible portion 68 of membrane structure 47, and data acquisition, analysis, and control system 55. A computer controlled XYZ stage upon which membrane structure 47 and thin film 57 to be bulge tested are mounted, and computer controlled pressure regulator and pressure sensor 51, are used to place freestanding flexible portion 68 of membrane structure 47 and thin film 57 through predetermined pressure cycles. The pressure sensor is in operative communication with cavity 53 (e.g. within the cavity) to monitor pressure therein.

For accurate testing, membrane structure 47 (including portion 68) is characterized alone via bulge testing so that thickness measurements, dimensions, and stand-alone bulge testing data can be taken whereby any residual stress, prior deflection, and other properties or responses are more precisely known to the user before film 57 is applied thereon. Then, thin film 57 to be tested is applied to membrane structure 47 and bulge tested. Because the physical properties and characteristics of membrane structure 47 are known, the bulge test data can be used to determine residual stress and elastic modulus characteristics of film 57 via known mathematical techniques.

Figure 7:
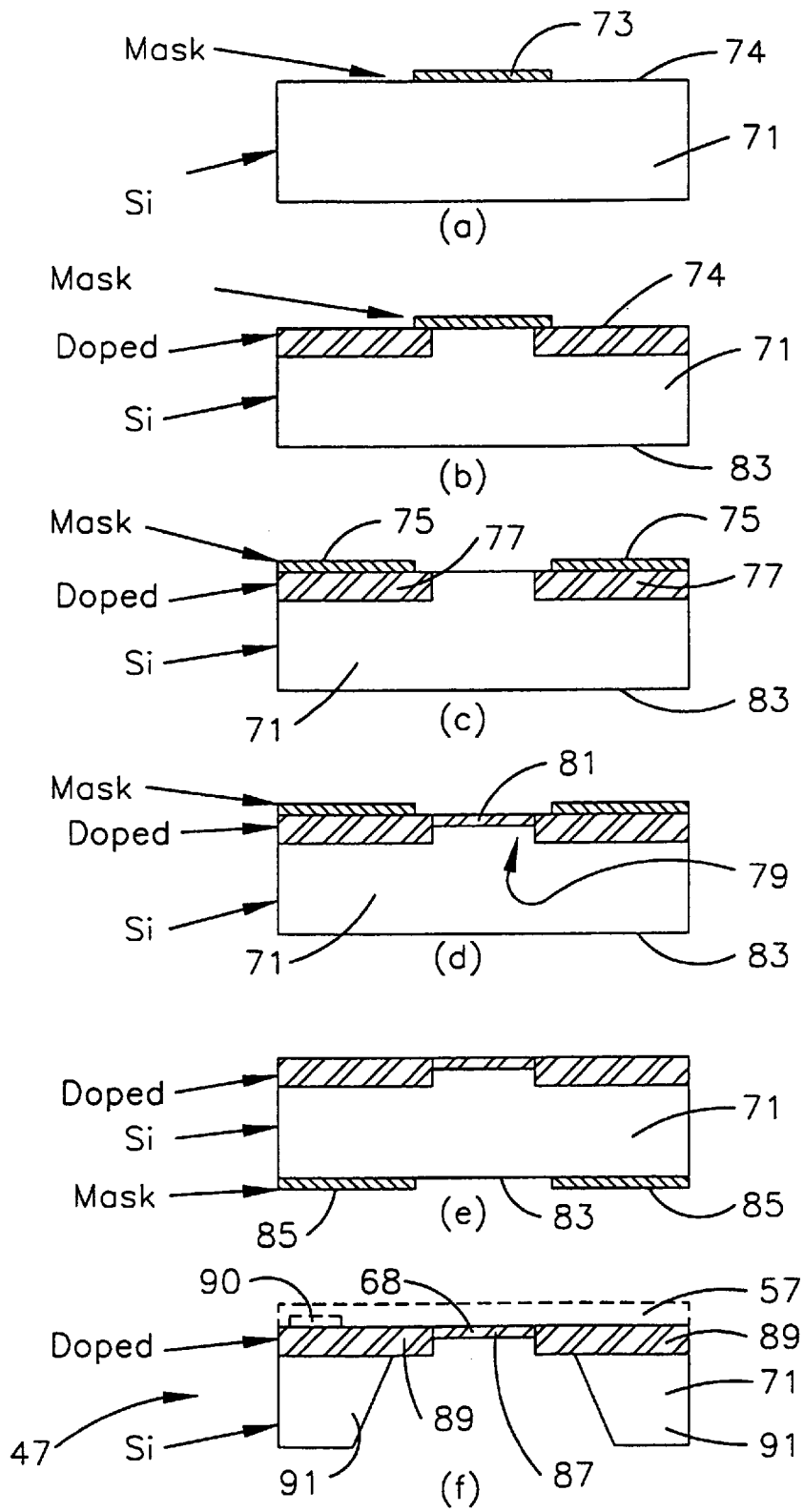

To measure the thickness of either the freestanding membrane film 68, or film 57, a mask or coating 90 (see FIG. 7(*f*)) can be in place on a small portion of the wafer away from the freestanding portion during deposition, and then removed to lift off film 57 thereby creating a step which can be used to measure the thickness of layer 57. The resulting step surface may then be measured to determine the thickness of the film at issue.

Preferably, optical displacement transducer 49 records either the center 52 of deflection of film 57 or alternatively the center of the film over the cavity relative to non-deflected points 54 spaced therefrom, as a function of pressure. The maximum and minimum compliance which may be measured by the FIG. 5 system is determined by the resolution and maximization capabilities of the pressurization system (i.e. regulator, pressure transducer, and control system), and deflection transducer 49. These values are variable, and should be chosen for the particular application to which the FIG. 5 system is to be applied. Additionally, the particular geometry of membrane 47 (and the film 57 to be tested) may be optimized for particular materials and mechanical properties of interest.

Pressurization system 51 preferably applies pressures from about 0 to 5 psi to cavity 53, and transducer 49 measures membrane portion 68 and film 57 deflections of from about 0.01 to 1,500 μm (preferably from about 0.1–100 μm). Membrane compliance from about 0.002 to 75,000 μm/psi (preferably from about 0.02 to 100 μm/psi) may be measured. Test control and data analysis, in certain embodiments, are provided by PC compatible computer system 55 with, for example, a 12 bit analog digital data acquisition board.

According to alternative embodiments of this invention, cavity 53 may be de-pressurized or evacuated thereby causing freestanding membrane portion 68 and/or film 57 to bulge downwardly into the cavity. In such embodiments, the downward deflection is measured and used to determine the stress and modulus properties discussed herein.

In still other embodiments, cavity 53 is neither pressurized nor evacuated, and the pre-stresses inherent in film 57 and/or portion 68 cause it to bulge either outwardly or inwardly. This bulging may be measured by transducer via center point 52 relative to non-deflected points 54, as discussed herein.

Figure 5B:
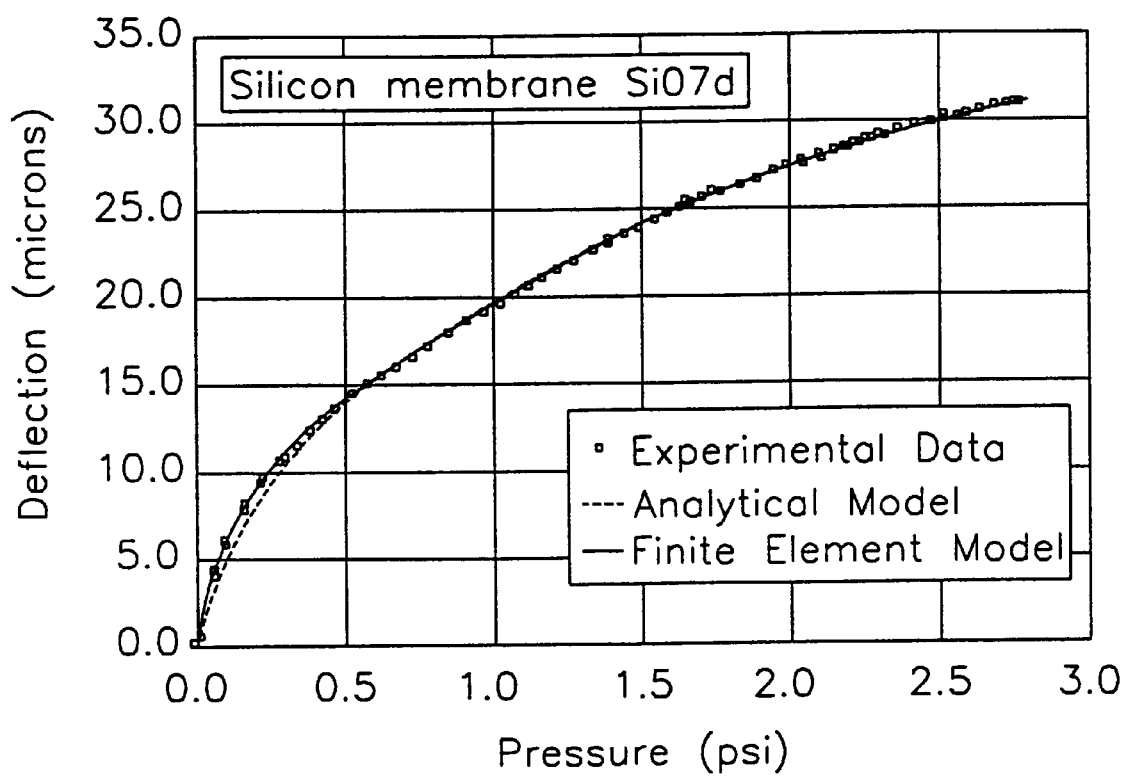
FIG. 5(b) is a graph illustrating the upward center deflection of the freestanding flexible portion (e.g. circular-shaped) of a silicon membrane, as a function of pressure, when tested in the FIG. 5(a) bulge testing system.

FIG. 5(b) is a pressure v. deflection curve for a silicon membrane 47, and illustrates that a well-characterized predictable membrane structure 47 can act as a substrate for the evaluation of a number of different thin film coatings 57. Thin films, layers, and coatings 57 herein are typically from about 100 Å to 500,000 Å thick, preferably from about 100 Å to 50,000 Å thick, and most preferably from about 500 Å to 5,000 Å thick. In certain embodiments, films or layers (e.g. paint) of even greater thickness may be bulge tested. In a commercial setting, this system can measure residual stress of a film 57 within about ±5% accuracy.

Figure 5C:
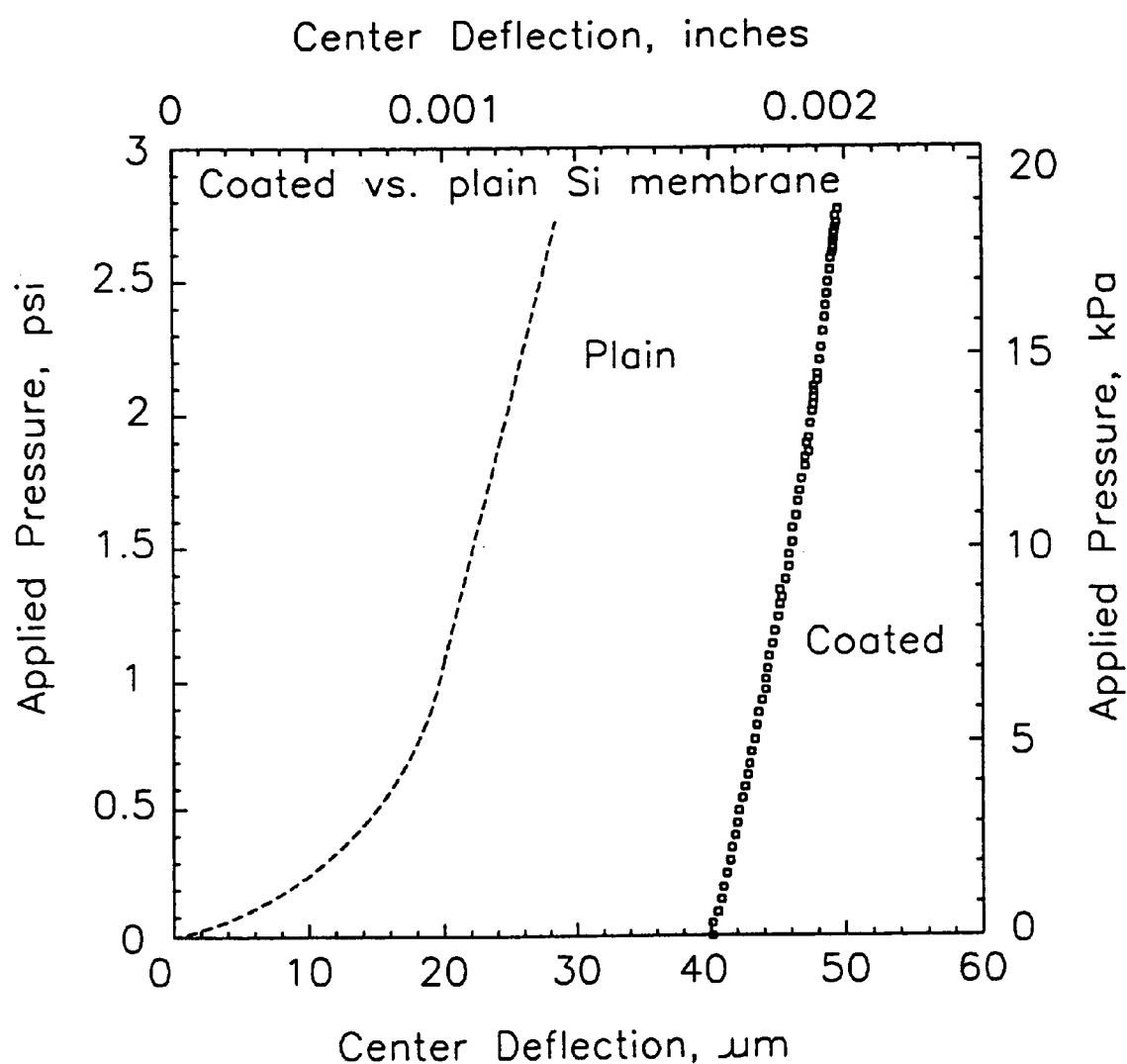
FIG. 5(c) is a graph illustrating the upward center deflection as a function of applied pressure, using the FIG. 5(a) system, wherein both an uncoated silicon freestanding membrane portion (e.g. circular-shaped) deflection is illustrated as well as the curve for the same freestanding membrane portion coated with a thin film to be analyzed.

FIG. 5(c) is a graph illustrating applied pressure (psi) v. center 52 film deflection (μm) for both an uncoated stand-alone flexible membrane portion 68, and such a portion 68 coated with a thin film 57. A large initial deflection in the coated membrane (e.g. at 0 psi–0 psi applied pressure) may be due to the high residual pre-stress introduced by film 57.

The response of the flexible freestanding portion 68 of membrane structure 47 to pressurization in cavity 53 is a function of the geometry and material properties of the membrane, and when applied, the thin film overcoat 57 to be measured.

In order to determine the mechanical properties of film 57 to be measured, the geometry of the membrane 47 must be precisely controlled, and measured or known prior to application of film 57, and the thickness of the thin film 57 to be measured must be accurately determined. A variety of manufacturing techniques are disclosed herein which have been found to create improved and more accurate and consistent membrane structures 47, these enabling the membrane structures to be uniformly characterized relative to one another.

Accurate mounting of membrane structure 47 on structure 45 is also important for reliable characterization and measurement. Membrane structure 47, and the thin film 57 to be measured and placed thereon, are originally held in place and hermetically sealed to the pressure (or evacuation) system. Furthermore, it is important that stresses not be introduced to membrane structure 47 by the technique which is utilized to attach the membrane to structure 45. Motion of membrane structure 47 due to temperature changes, vibration, or poor fixation to structure 45 is desired to be minimized. Additionally, flatness of the bond between membrane structure 47 and structure 45 is important, and the alignment of the membrane relative to structure 45 is done by scanning via transducer 49, or alternatively by fabricating membrane structures having freestanding portions 68 exactly centered to their structure/chip shoulder 91 (see FIG. 7(f)), with the structure/chip then being placed into a jig (not shown) exactly positioning the membrane portion 68 centered relative to transducer 49. In some embodiments, fiduciary marks are applied to the membrane, or film 57, to enable efficient manual or automatic orientation of the membrane portion 68 or film 57 in the system. In certain embodiments, membrane structure 47 is attached to a pressurization mounting chuck which functions as supporting structure 45 and transducer uses the fiduciary marks on portion 68 or film 57 to accurately position the center 52 of film 57 over cavity 53 directly beneath the transducer.

In certain preferred embodiments of this invention, membrane structure 47 is adhered or bonded to pressurization chuck 45 by way of Crystal Bond™ polymer. Crystal Bond™ polymer, a mounting wax, which is available from vendors of polishing supplies, such as Buehler, Ltd., Lake Bluff, Ill., as Part No. 408150. An important characteristic of this polymer bonding material is that it has a glass transition temperature above the temperature at which bulge testing is usually performed. This polymer adhesive is heated above its rather low glass transition temperature (about 80° C.) to allow liquid flow into a thin layer. The mounting wax (e.g. element 200 in FIG. 6) has a wax or solid to liquid transition temperature of at least about 40° C., preferably of at least about 60° C., and most preferably at least about 80° C. Membrane structure 47 is then placed onto this liquid polymer and upon cooling is fixed in place on structure 45. Membrane structure 47 may be removed from structure 45 by heating the mounting chuck to 80° C. or higher (and can be followed by rapid removal of residual Crystal Bond using acetone). Provided that the substrate of membrane 47 is sufficiently rigid, stresses introduced to the membrane by mounting are minimized when Crystal Bond™ is used. It is noted that other polymers having characteristics similar to Crystal Bond may also be used (e.g. having a glass transition temperature greater than temperatures at which bulge testing is typically performed).

Epoxies and cyanoacrylate adhesives may alternatively be used to bond membrane structure 47 to supporting structure 45, but these are undesirable in some circumstances because it is difficult to remove the membrane from structure 45. Without soaking the membrane and chuck in solvents such as acetone, dissolution is slow at best. These epoxies or adhesives cannot be removed by heating because they decompose and leave carbonized residue rather than melting, and dissolution of epoxies or adhesives in solvents such as acetone is very slow, and tends to leave a thin layer of organic reside which could alter the response of the membrane and impair thin film 57 analysis.

Optionally, mechanical clamping techniques may be used to connect silicon based and metallic membrane structures 47 to mounting structure 45. However, it is sometimes difficult to reproducibly clamp and hermetically seal membrane structure 47 to mounting structure 45. It is noted that a rigid, stress free adhesion of membrane structure 47 to structure 45 is important, as is the hermetic seal between 47 and 45. This, surprisingly, is best achieved with Crystal Bond™ or any other suitable mounting wax, although alternatives are, of course, contemplated. For example, when it is undesirable to raise the temperature above 80° C. or when simple adhesives are sufficient, epoxy, cyanoacrylate, or even simple mechanical clamping, may be used instead of Crystal Bond™.

In certain embodiments, in order to ensure the top alignment plane of membrane structure 47 as being perpendicular to the vertical axis of transducer 49, and the centering of transducer 49 relative to membrane structure 47, a computer controlled motion system is used. The precision to which deflection transducer 49 is centered upon membrane structure 47 (and/or film 57) is dictated by the sampling spot size and the curvature of the membrane structure and/or film 57. Current laser triangulation systems have spot sizes on the order of about 35 μm. Positioning of transducer 49 in the center of membrane structure 47 and film 57 may require incremental membrane motions which are achievable by standard and air bearing XY or XYZ stages with piezoelectric, stepper motor and/or brushless DC motor drive systems. During alignment, it is important that the translation stage being substantially free of pitch, roll, and yaw. The fiduciary marks also help substantially in alignment. Procedures for finding and centering a transducer on a membrane are useful for arrays of membrane portions 68 as well, as the instrument can then automatically move from portion 68 to portion 68 to make measurements.

Figure 1:
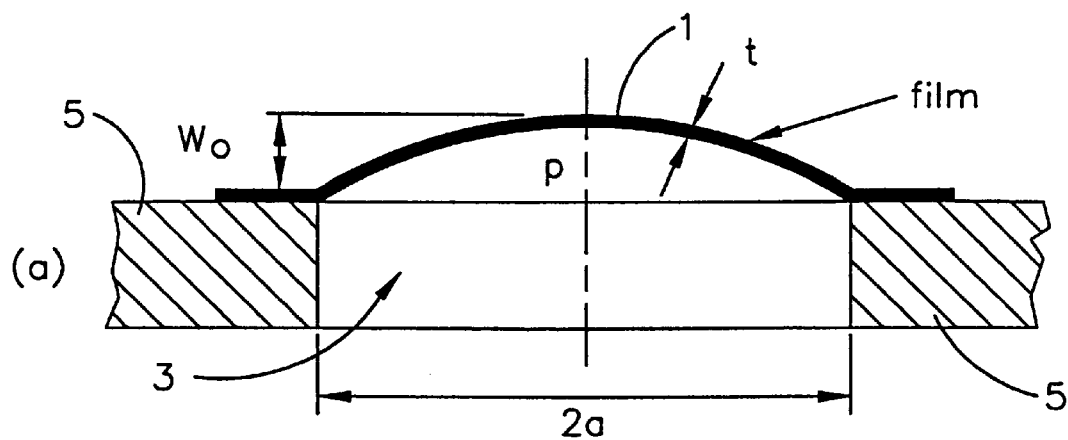
Figure 2:
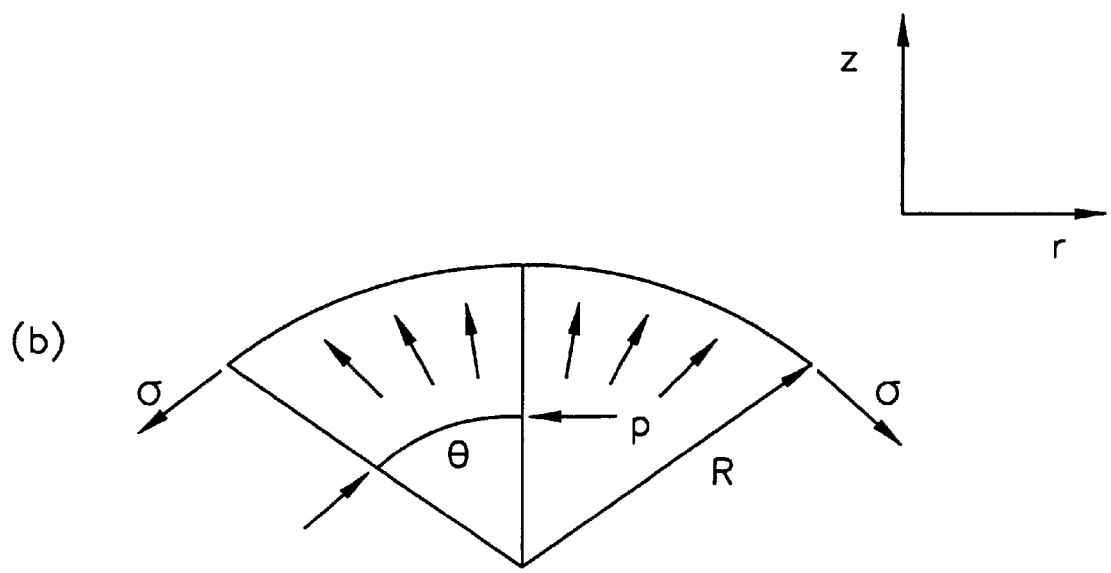
Figure 3:
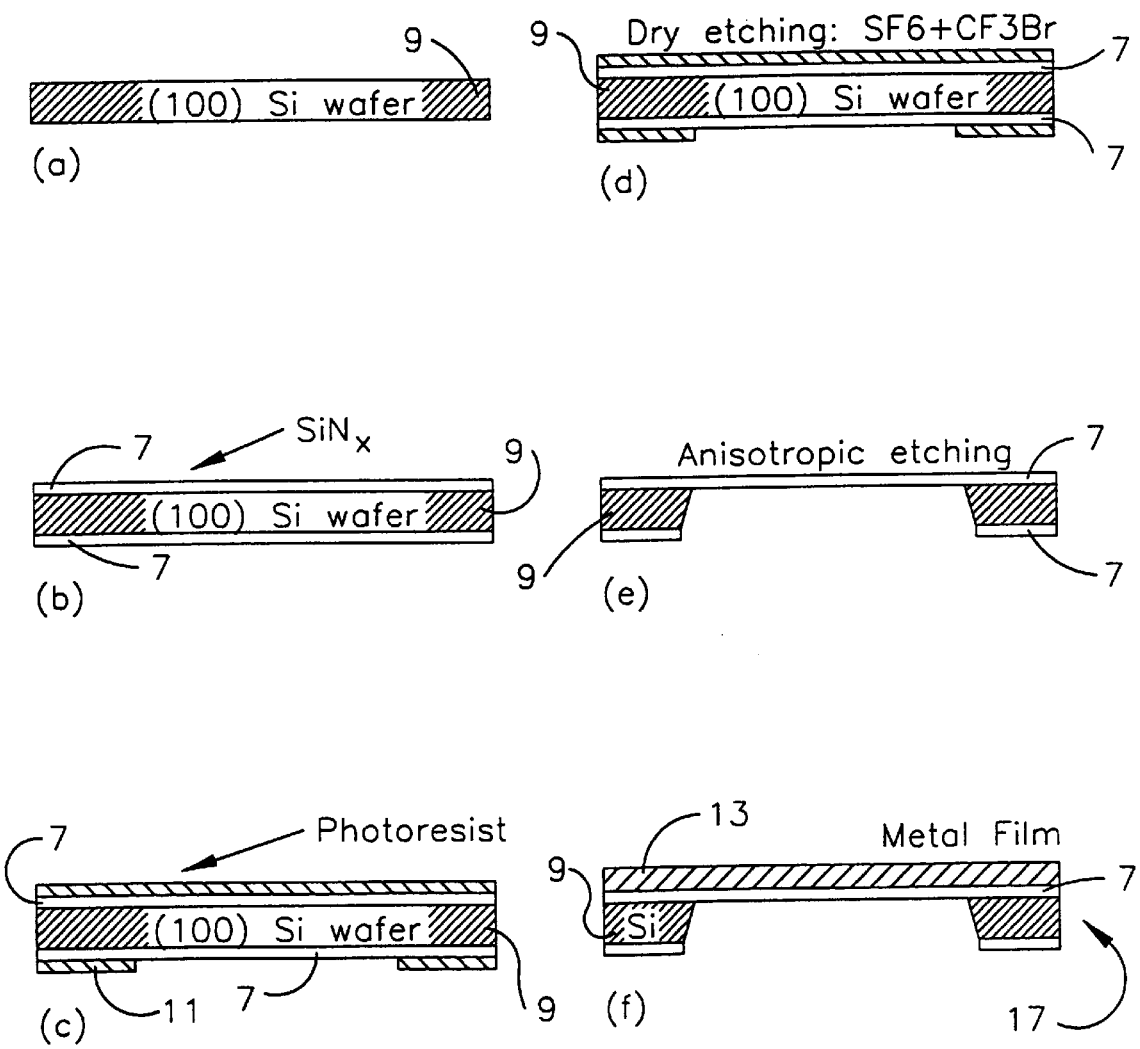
Figure 4:
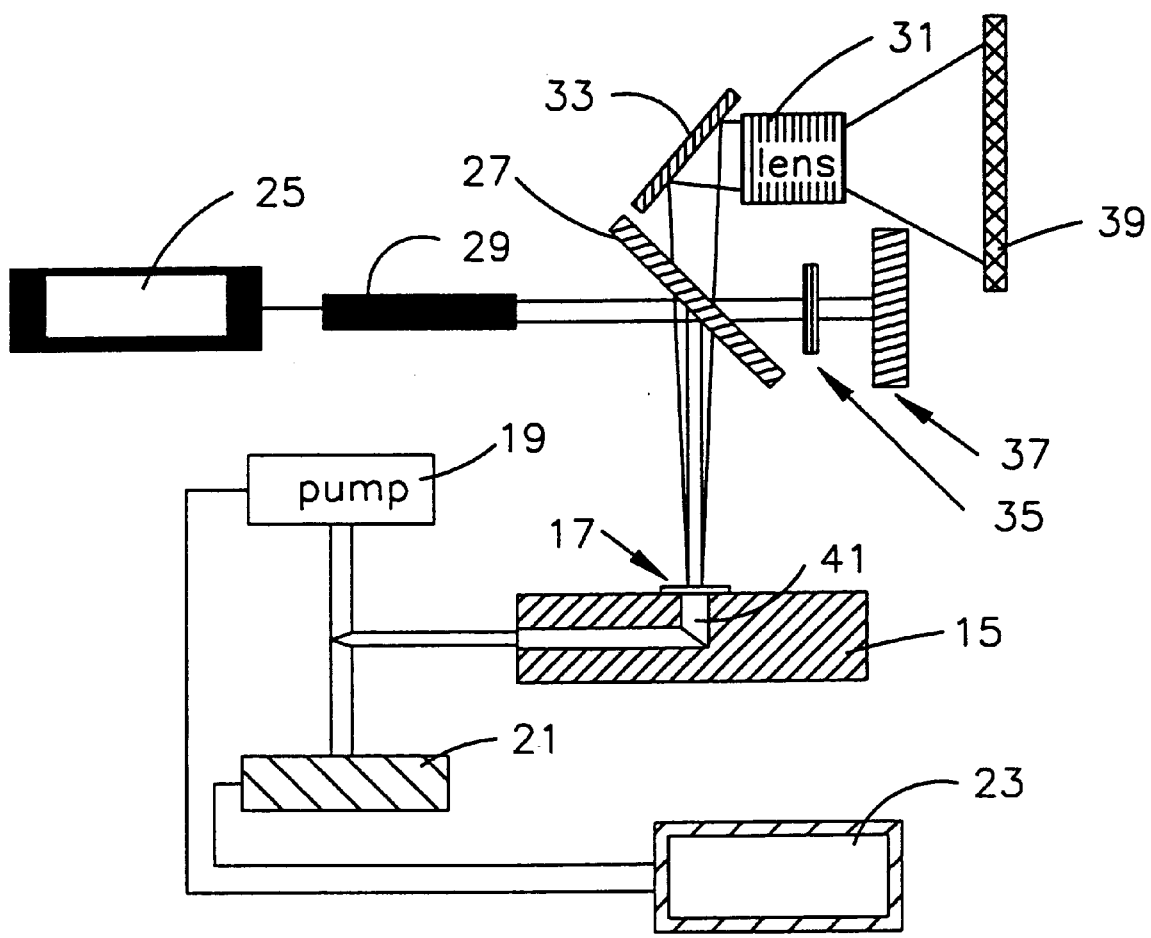

Non-contact deflection measurement of freestanding portion 68 of membrane structure 47 and thin film 57 thereon, over a circular area on the order of tens of microns with submicron resolution, is provided in certain embodiments. Ideally, the system remains relatively insensitive to changes in surface finish due to coating application, and to loss of intensity due to transmission through membrane 47, and/or thin film coating 57 thereon. The radiation used by transducer 49 for measurement typically does not excite any response in membrane structure 47, or the thin film coating 57 thereon, which may alter the response of the membrane. It is still possible to achieve measurements with interaction. Furthermore, deflection measurement device 49 samples a small enough area of portion 68 of membrane structure 47, and thin film coating 57 thereon, so that the local radius of curvature of the surface of portion 68 and film 57 does not introduce significant or substantial error into the measurement. When measuring deflection, in certain embodiments, the deflection of the center 52 of the thin film coating 57, on or independent of membrane portion 68, is measured relative to non-deflected edges 54 of the membrane, non-deflected points 54 being spaced from cavity 53. Simple measurement of the center 52 is not always sufficient. Thus, at a minimum, where resolution dictates, three measurements are utilized—the center point 52 deflection of thin film coating 57, and a pair of non-deflected opposite points 54 on the edge of the membrane structure. Referring to FIG. 1, this type of measuring using the deflection of the center 54 of the film relative to non-deflected edge points 54 can be easily illustrated, with the apex of the bulging film in FIG. 1 being the deflected center 52 of the film and the non-deflected edge portions/points 54 being on the two parts of the bulging film that are not over the cavity and which are not deflected.

Accordingly, another embodiment of the deflection measurement devices according to this invention, measures a section of the deflected membrane profile, or the entire profile, or the entire three-dimensional shape of the membrane. This may be accomplished using profilometry surface analysis systems such as laser triangulation or white light interferometry. The advantage of this embodiment is that it measures the center deflection (at a center point 52) relative to points 54 on the undeflected edges of the substrate. The necessary information includes the center deflection, measured relative to two points 54 on the substrate which define a line that substantially bisects or crosses membrane portion 68. The additional information provides additional accuracy.

Table 1 below set forth three different optical displacement transducers which may be used to measure deflection of freestanding portion 68 and/or film 57.

TABLE 1

Displacement Transducer Models

| Manufacturer | Model | Description |
| --- | --- | --- |
| Lucas Control Systems | Schaevitz TwinStar 15/3 | Laser triangulation sensor |
| Philtec, Inc. | Model D6L | Fiber optic displacement sensor |
| Zygo, Inc. | New View 2000 Non-Contact Surface Structure Analyzer | Scanning white light interferometer |

Different approaches may be used to measure deflection of the freestanding flexible portion 68 of the membrane, and overlying film 57, without mechanical contact therewith. For example, in certain embodiments, electrical methods based upon capacitive and inductive schemes may be used. Also, acoustic-ultrasound may be used to measure deflection, as may contact probe systems. Also, electron tunneling may be used to measure deflection. However, such electrical methods are not practical for use with all membrane and thin film materials of interest. Alternatively, variable induction deflection measurement systems having spot sizes on the order of about 2 mm, may be used, but are too large for many membrane designs. Still further, atomic level measurement technologies such as atomic force microscopy (AFM) may be used to measure local deflections of membrane portion 68 and coating 57, but these are limited to small areas and deflections.

Optical techniques are preferred for measuring deflection of film 57 and the flexible freestanding portion 68 of membrane structure 47, and provide a wide variety of approaches to non-contact displacement measurement. Typically, optical techniques for deflection measurement by transducer 49 are based on monochromatic light sources with the exception of white light interferometry. Interferometric, reflection probe, laser focusing, and laser triangulation systems provide viable optical deflection measurement transducers 49.

Interferometric measurement systems based upon HeNe lasers, while costly, may also be used for precision distance measurement in order to detect the bulging or deflection of portion 68 and/or film 57. However, it is noted that the HeNe laser light may experience transmission through silicon. White light interferometry (or interferometers 49) may be used for surface profiling of freestanding portions 68 and films 57, relative to the surrounding substrate. Reflection probes may also be used to measure deflections of the freestanding portion 68 of membrane structure 47, and/or film 57, although these sometimes suffer from sensitivity to changes in surface roughness, reflectivity, and transmission through silicon. In another preferred embodiment, a laser triangulation transducer 49 is used for characterizing membrane structure 47 and coating 57 surfaces, and center 52 deflection relative to edges 54 thereof.

It has been found that the use of stored lookup tables is surprisingly useful in the determination of film (thin films, coatings, layers, etc.) properties herein. For example, computer-controlled system 55 may have stored therein (e.g. stores in a RAM or ROM) a lookup table which, for each potential thin film material 57 or membrane portion 68 to be tested, includes potential thicknesses and measured deflections at particular pressures or evacuation, and a resulting stress value (e.g. residual stress). For example, such a lookup table may include two axes, an X axis and a Y axis, wherein the Y axis defines different thicknesses of a given material to be bulge tested, and the X axis includes a plurality of potential measured deflections at different pressures that are measured via transducer 49. Thus, when the system measures a particular deflection, the lookup table for that particular material being tested may be accessed, and because the thickness and material of the film being bulge tested is known, it is possible from the lookup table to determine the precise residual stress. For example, if an aluminum thin film 3,000 Å thick is bulge tested, and a deflection of 5,000 Å is measured, then an aluminum film lookup table stored in the computer is accessed and when the thickness of the film is matched up with its measured deflection and pressure applied, the lookup table will indicate a predetermined residual stress (or other stress or property value) of the film. A different lookup table may be provided in the system for each material, or alternatively, one large lookup table inclusive of all potential materials which may be tested can be provided.

Pressurization system 51 applies a known pressure or pressurization profile. The application of gas into cavity or chamber 53, in certain embodiments, is such that membrane structure 47 is not adversely affected by the gas, and temperature fluctuations of significance do not occur so that membrane 47 is relatively stable. In certain embodiments, special reflective or opaque coatings (e.g. gold, aluminum, platinum, etc.) can be placed over or on film 57 to facilitate optical measurement of deflection.

Set forth below in Tables 2 and 3 are different exemplary computer-controlled pressure regulators which may be utilized according to different embodiments of this invention in order to detect the pressure being applied to the lower side of membrane portion 68 via cavity 53.

TABLE 2

E/P and I/P Transducers
(computer-controlled pressure regulators)

| Company | Name | Model | Comments |
| --- | --- | --- | --- |
| Proportion Air | QB1T Servo Control Valve | QB1TFEE005 | 0–5 psi output, 0 to 10 V FS |
| Bellofram | Type 1001 E/P Transducer | 966-210-000 | 0–5 psi output, 0 to 10 V FS |
| Tescom | ER3000 Electronic Pressure Controller | ER3000S-A001 | 0–5 psi output |

TABLE 3

Electropneumatic Transducer Technical Specifications

|  | Proportion Air (QB1TFEE005) | Bellofram (966-210-000) | Tescom (ER3000S-A001) |
| --- | --- | --- | --- |
| Supply Voltage | 15–24 V DC | 9–40 V DC | 19.5 to 28.5 V DC |
| Supply Current | 250 mA max | | |
| Command Signal Voltage | 0–10 V DC | 0–5 V DC | 1–5 V DC |
| Current | 4–20 mA differential | 4–20 mA | 4–20 TnA |

TABLE 3-continued

Electropneumatic Transducer Technical Specifications

|  | Proportion Air (QB1TFEE005) | Bellofram (966-210-000) | Tescom (ER3000S-A001) |
| --- | --- | --- | --- |
| Command Signal Impedance Voltage | 4700 Ω | 6000 Ω | |
| Current | 100 Ω | | |
| Analog Monitor Signal Voltage | 0–10 V DC | none | 1–54 V DC |
| Current | 4–20 mA sinking | | 4–20 mA |
| Pressure Range | 0–5 psi | 0–5 psi | 0–5 psi |
| Cv Capacity | 0.04 | | 0.01 |
| Linearity/ Hysteresis | +–0.15% FS | 0.01% span typical, 0.10% span max | |
| Repeatability | +–0.02% FS | 0.01% span, typical, 0.10% span max | |
| Accuracy | +–0.2% FS | per ISA 51.1 +–0.1% span typical, +–0.25% span max | |
| Operating Temperature | 0–70 C. | –20 to 160° F. | |
| Vibration Effect | | Less than 0.5% of span per 1G, 5–2000 Hz, 3G maximum, 3 axes | |

A differential pressure transducer is typically used to determine the pressure applied to membrane portion 68. Due to low pressures used in the system, daily fluctuations in atmospheric pressure may be an appreciable fraction of the applied pressure and differential measurements must be made. Silicon diaphragm and bonded strain gauge pressure transducers are both viable technologies for this application.

In preferred embodiments, clean, low moisture, compressed gases are used as the pressure medium for applying pressure through regulator 51 into cavity 53. Failure to control the purity of the gas may result in corrosion of the system. Exemplary gases for applying pressure in cavity 53 include nitrogen, dry air, He, and/or argon.

Membranes

It has been found that the membrane structures 47 discussed below, and their methods of manufacture, are improvements over the prior art with respect to efficiency, durability, and/or manufacturability to predetermined tolerances. This allows the instant inventions to be commercially viable. These membrane structures 47 and/or methods of manufacture enable mass production of such membranes to a predetermined finite tolerance value, ± about 5%, preferably within about ±3%, and in some cases about ±1%. In other words, for example, it has been surprisingly found that if a manufacturing process described below is used to make one hundred membrane structures 47, at least about 95% of the resulting membrane structures would have the same thickness ± about 5% (preferably ± about 3%, and most preferably ± about 1%) of freestanding portion 68, and in circular embodiments the same diameter ± about 5% of portion 68 and cavity 53. For example, if a thickness of about 1000 Å is desired, at least about 95% of the resulting membrane structures will have a portion 68 having a thickness within about 5% of 1000 Å (i.e. a thickness of portion 68 of from about 950 to 1050 Å), and preferably a thickness within about 3% of 1000 Å (i.e. a thickness of portion 68 of from about 970 to 1030 Å), and most preferably a thickness of within about 1% of 1000 Å. This is important for commercial implementation of bulge testing.

Preferably, freestanding membrane portions 68 are made of single crystal silicon which is reproducible into a geometric shape in mass numbers (e.g. substantially the same thickness and diameter of portion 68 can be achieved time after time). Although not preferred, silicon nitride and/or silicon oxide may be used to form portion 68 in alternative embodiments.

Optionally membrane portions 68 in any of the structures 47 discussed herein, of varying thickness or in-plane geometries, may be used to evaluate different properties such as Poisson's ratio or to facilitate the measurement of tensile stresses through induced buckling.

Membrane structures 47 and/or freestanding portions 68 may be either circular or square in shape according to different embodiments of this invention. Circular membranes often render measurements insensitive to anisotropy, while square or otherwise rectangular membrane structures permit the detection of anisotropy. Both have advantages in different applications. Accordingly, while circular membrane portions 68 are preferred in certain embodiments, both may be manufactured and used in all embodiments herein.

Generally speaking, the freestanding thin film membrane portions 68 herein are from about 500 Å to 15 μm thick, and preferably from about 500 Å to 10 μm thick.

A first type of membrane structure 47 shown in FIG. 6(c) is manufactured with a pyrex glass substrate 61 and anodic bonding. Referring to FIGS. 6(a)–6(c), pyrex glass substrate 61 is provided as shown in FIG. 6(a). Cylindrical or circular hole(s) 63 are then defined (e.g. drilled or ultrasonically machined) in substrate 61 [see FIG. 6(b)]. Hole(s) 63 in glass substrate 61 may have a diameter of from about 0.5–20 mm, preferably from about 1.0–10.0 mm, and most preferably from about 2.0–5.0 mm. A thin single crystal silicon film 65 about 9 μm thick is then bonded to the top surface of glass substrate 61 by anodic bonding in order to form freestanding membrane portion 68. When anodic bonding is used herein, voltage (e.g. 600 volts DC bias) and temperature on the order of about 300 degrees C. or higher are used across silicon 65 and glass 61 to bond the glass to the silicon. An exemplary silicon layer or film 65 can be purchased from Virginia Semiconductor, who produces very thin single crystal silicon wafers which may be used as film 65.

The resulting FIG. 6(c) membrane structure 47 may then be bonded to mounting structure 45, and thereafter a thin film 57 to be analyzed deposited or otherwise disposed on the membrane's top surface over layer 65 and cavity 53. The only portion of the FIG. 6(c) membrane structure 47 that is susceptible to bulging during bulge testing is the freestanding flexible membrane portion 68 that covers drilled hole(s) 63 (and cavity 53).

In certain embodiments, Virginia semiconductor can provide silicon wafers 65 having about a 2" diameter, about 9 μm thick with flatness 3, planarity 3, and taper of about 2.5. The thickness of layer 65 (and thus freestanding portion 68) is preferably from about 500 Å to 15 μm in certain embodiments herein (most preferably from about 1 μm to 15 μm thick), while the thickness of glass 61 in the FIG. 6 embodiment is preferably from about 0.075 to 0.250 inches, most preferably about 0.125 inches.

In certain other embodiments, a double diffusion technique is used to manufacture membrane structures 47, as illustrated in FIGS. 7(a)–7(f). Firstly, a first area of the top surface of single crystal silicon wafer 71 is covered with circular mask 73 as shown in FIG. 7(a). Other shaped masks may also be used (e.g. oval, square, etc.). Then, using mask 73, the top surface 74 of wafer 71 is exposed to deep diffusion 77 (or implant followed by deep diffusion) with an etch stopping material in the area not covered by the mask, as shown in FIG. 7(b). Mask 73 is then removed. Then, as illustrated in FIG. 7(c), another mask 75 is deposited or provided on a second area which had previously been doped by deep diffusion. Alternatively, the second mask need not be used, and the top surface may simply be exposed to shallow diffusion, or implant followed by anneal giving shallow diffusion depth to a predetermined membrane portion 68 thickness depth as shown in FIG. 7(d). The first and second areas discussed above preferably slightly overlap, but need not. The diffusion depth in the FIG. 7(d) step is less than the diffusion depth in the FIG. 7(b) step. The difference between this predetermined FIG. 7(d) depth and the depth of diffusion in the FIG. 7(b) step, accounts for step 79 between these two depths or areas. The timing employed in the FIG. 7(d) step is important to obtaining a reliable predetermined flexible membrane portion depth which is defined by the thickness of diffusion 81. The diffusion steps discussed above in applying etch stop to the first and second areas may be conducted in either order.

Following the FIG. 7(d) step, the backside 83 of wafer 71 is masked as illustrated in FIG. 7(e) at 85, for an anisotropic etch in basic (caustic) etchants of the class KOH, EDP, TMAH, etc. Thereafter, as illustrated in FIG. 7(f), the backside of wafer 71 is anistropically etched to form the freestanding flexible portion 68, 87, of the membrane structure 47. The etch can be KOH, EDP, TMAH, or other known etching agents that employ an etch stop. The resulting FIG. 7(f) membrane structure 47 may be used in bulge testing embodiments of this invention. Membrane structure 47 includes thin freestanding membrane area 68, 87 upon which the thin film 57 to be bulge tested and analyzed is deposited. Flexible freestanding portion 68, 87 of membrane structure 47 is surrounded by thicker non-flexible membrane portions 89 that were formed as a result of the etch stop provided in the FIG. 7(b) step. Shoulder(s) 91 of silicon wafer 71 remain so as to allow membrane structure 47 to be adhered to the mounting structure to form cavity 53.

According to other embodiments of this invention, membrane structure 47 is formed by way of a SOI method using a silicon-on-insulator wafer, as illustrated in FIGS. 8(a)–8(e). In the method, a wafer 101 prepared with by the SIMOX method, or a SOI method, is provided, e.g. as shown in FIG. 8(a) (including four layers in this particular embodiment). For example, SIMOX wafer 101 may be obtained from Ibis Corporation, or alternatively from Nippon Steel. Wafer 101 includes an embedded oxide layer 107 above a single crystal silicon insulating layer 99. Epitaxial growth of silicon onto the oxide layer is used to increase the thickness of the silicon layer to that which is desired. These SIMOX wafers may have their single crystal silicon layer from about 1.0 to 20.0 μm thick, preferably from about 6.0–10.0 μm thick, depending upon the mechanical properties and thickness of the film being measured. The layers of wafer 101 are oxide layer 111, epitaxial silicon layer 110, oxide layer 107, and silicon insulating substrate 99. Top oxide layer 111 is optional, and is not needed in certain embodiments. Layer 111, whether silicon oxide or some other material, may optionally be deposited/grown onto Si layer 110, 68 to protect it during subsequent processing.

Following the provision of SIMOX wafer 101, mask 103 (e.g. photoresist, patterned silicon oxide, etc.) is applied to the backside of the wafer as illustrated in FIG. 8(b) to expose an area which is to define cavity 53. As in FIG. 7, mask 103 is annular with a circular opening 105 provided at its center so as to expose central surface area on the backside of the wafer. Following masking, in FIG. 8(c), deep reactive ion etching (RIE) is performed from the backside of the wafer, this etching stopping at $SiO_2$ layer 107 which functions as an etch stop. This RIE step in FIG. 8(c) forms circular aperture or cavity 109 in wafer 101, which finally ends up defining cavity 53 when the membrane is affixed to structure 45. Then, as shown in FIG. 8(d), mask 103 is stripped off of the backside of the wafer. The optional top silicon oxide layer 111 is then stripped off of the wafer so as to form flexible freestanding portion 68 of membrane structure 47, with a thin oxide underlayer as illustrated in FIG. 8(e). Oxide layer 107 may be removed in cavity 53 via etching or the like in certain embodiments. The FIG. 8(e) membrane structure 47 may then be adhered to mounting structure 45 by way of an adhesive (e.g. Crystal Bond™) as discussed above. A thin film 57 (illustrated in FIG. 8(e) in dotted lines) is thereafter applied to the top surface of the FIG. 8(e) membrane structure so that it can be bulge tested as discussed above.

Figure 8:
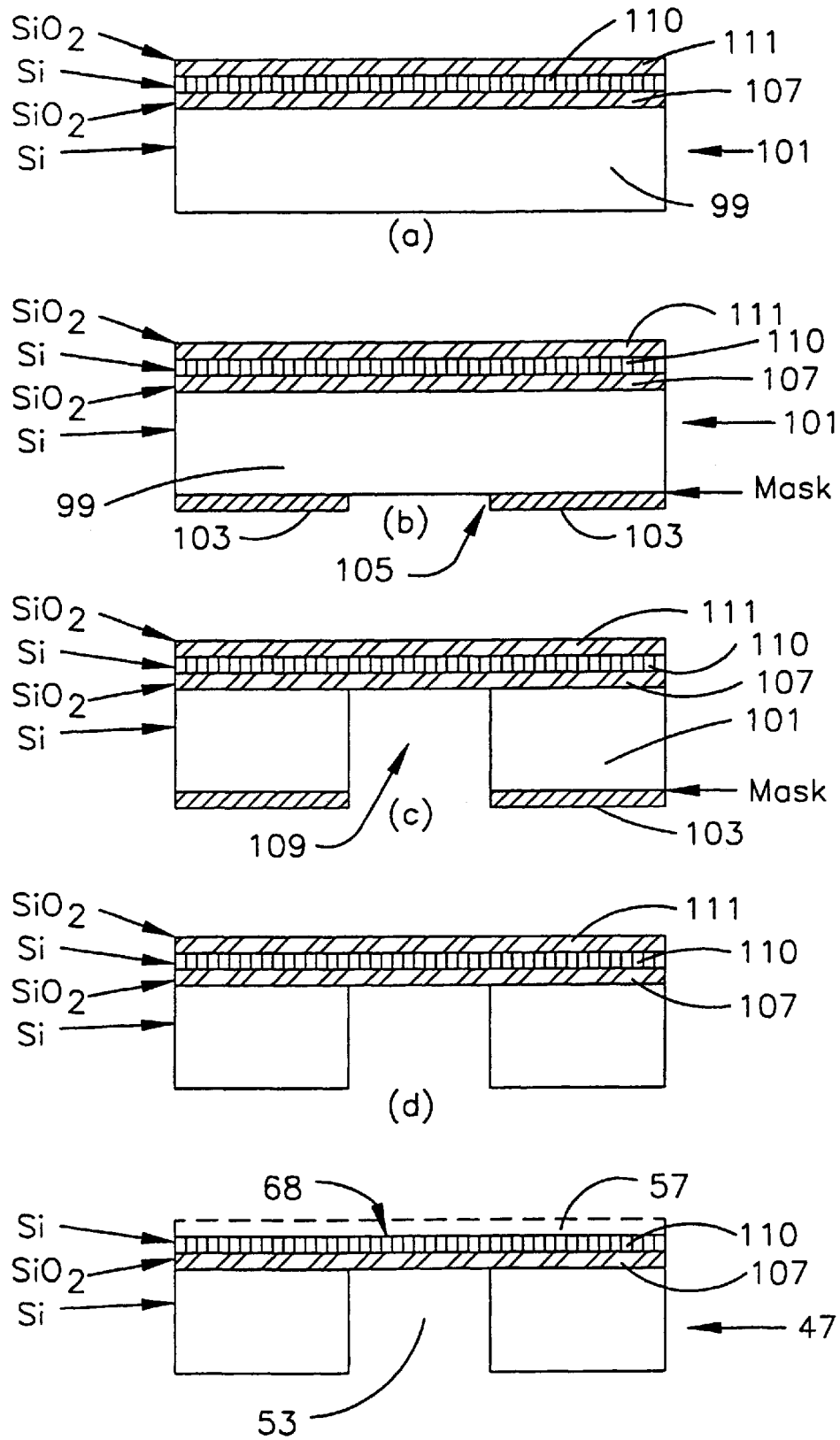

Membrane structures produced using the FIG. 8 embodiment generally produce more flat portions 68 than process using anodic bonding because elevated temperatures of the anodic bond tend to introduce non-uniform stress between the two wafers after bonding and cooling to room temperature. However, this can be minimized by accurately controlling the bond temperatures and tailoring the glass composition to match the thermal expansion coefficient of Si.

Figure 9:
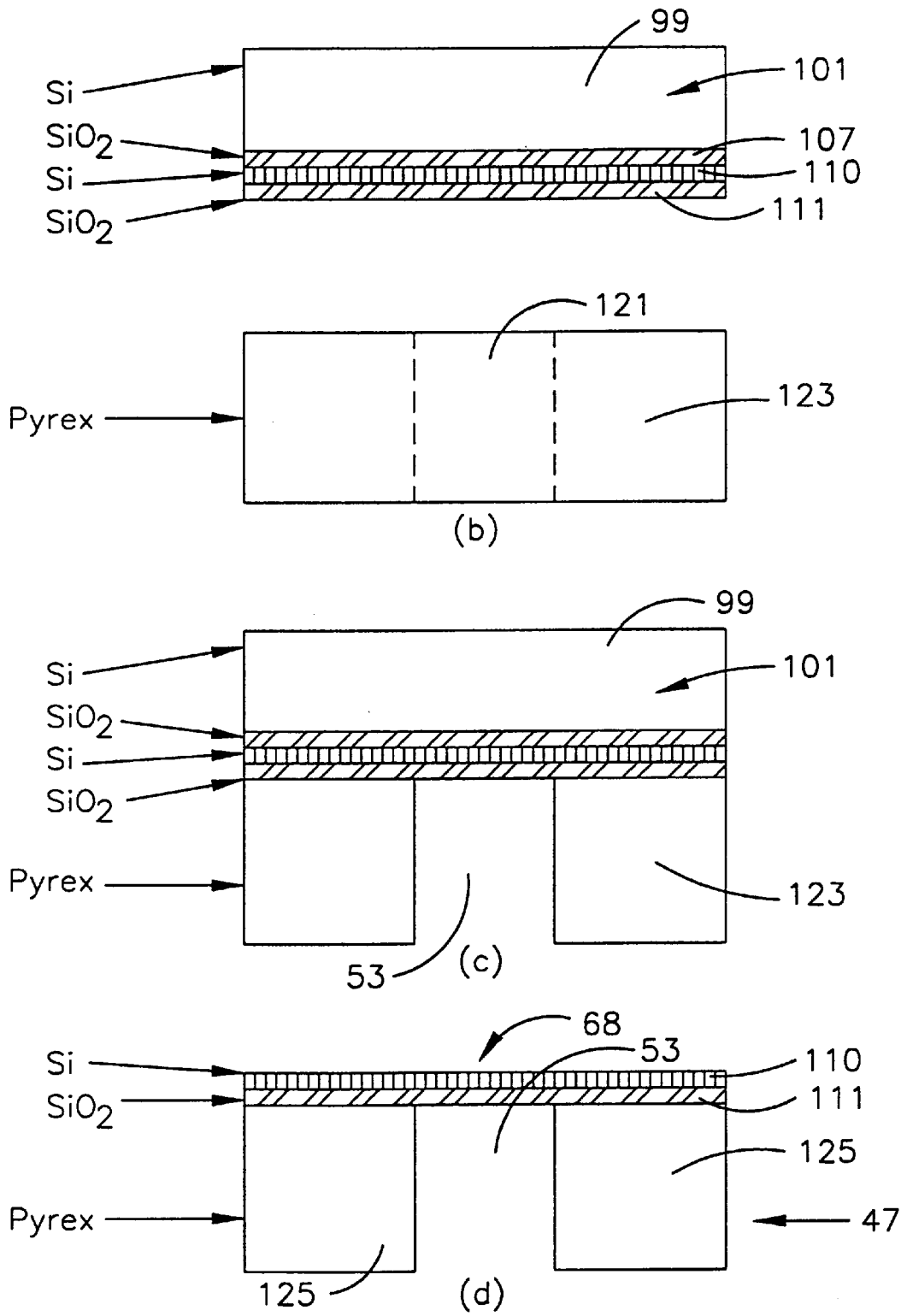
Figure 10:
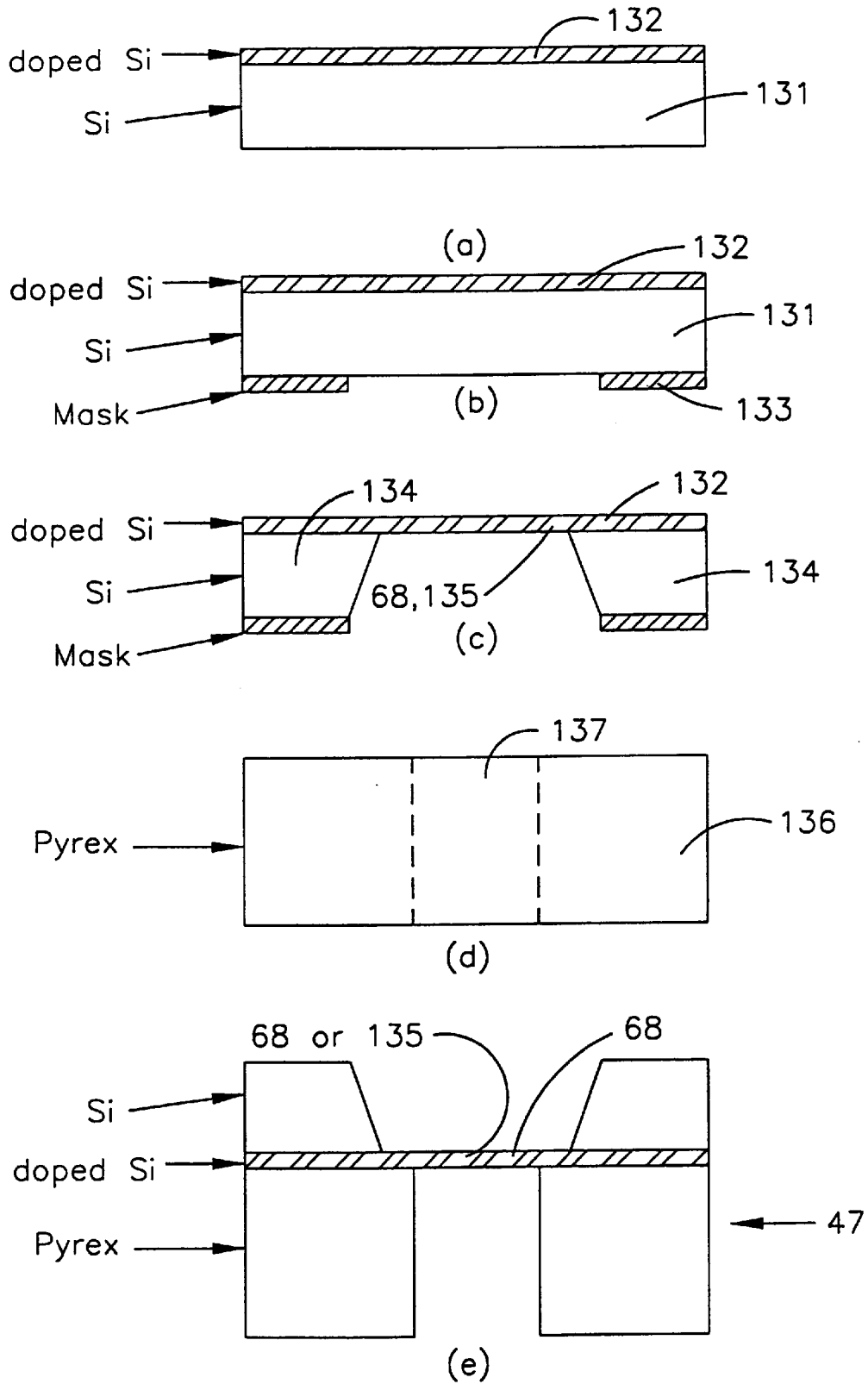

According to another embodiment of this invention illustrated in FIGS. 9(a)–9(d), membrane structure 47 may be made using both anodic bonding and a SIMOX wafer as discussed above. In preferred embodiments, layer 111 is not provided in the FIG. 9 embodiment herein. In FIG. 9(a), SIMOX wafer 101 is flipped upside down relative to its orientation in FIG. 8(a). Then, as shown in FIG. 9(b), a substantially planar pyrex glass (or other glass composition having a thermal expansion coefficient substantially matched to Si to allow anodic bonding) slide, wafer, disk, or substrate 123 (e.g. about 0.63" thick) is drilled with a circular hole(s) 121 (e.g. about 3.47 mm diameter hole(s)). One hole 121 is drilled in pyrex substrate 123, unless a plurality or an array of thin film membrane areas are to be formed on the substrate, or unless the manufacturing technique involves forming a plurality of holes 121 (equivalent to 63) in a large area substrate 123 and thereafter cutting up same into a plurality of different membrane structures.

Thereafter, as shown in FIG. 9(c), the drilled pyrex substrate 123 (equivalent to 61) is bonded to the oxide layer side of SIMOX wafer 101 using anodic bonding or the like. Then, as shown in FIG. 9(d), the main silicon insulating body of the wafer is removed along with the last silicon oxide layer of wafer 101, thereby forming the membrane structure 47 of FIG. 9(d). In preferred embodiments, layer 111 is not provided in the FIG. 9 embodiment, so that freestanding membrane portion 68 includes only silicon layer 110 in FIG. 9(d).

Also, the silicon substrate 99 can also be dissolved away, for example, in 25% TMAH (tetramethyl ammonium hydroxide) a 80° C. down to the buried $SiO_2$ layer which serves as an etch stop. The silicon bonded over hole(s) 121 may be protected from the TMAH with "black wax" or other polymer film(s).

The FIG. 9(d) membrane structure 47 includes a pyrex shoulder area 125 surrounding cavity 53 which is preferably annular. The top surface of membrane structure 47 includes both the upper silicon layer, and optionally even the second $SiO_2$ layer 107 in some embodiments. Membrane structure 47 is then bonded to mounting structure or chuck 45, and a thin film(s) to be bulge tested is placed on the upper surface of the membrane. The only portion of membrane structure 47 designed to "bulge" during testing is the flexible freestanding film/membrane portion 68 covering the drilled hole(s). Because the manufacturing technique described herein to make structure 47 are so accurate, the geometry and response characteristics, and stresses, of structure 47 are known. Thus, film 57 can be applied over portion 68 without having to separately bulge test each structure 47.

Exemplary SIMOX wafers herein available from IBIS Technology Corp., have a silicon layer 110 thickness of about 190 nm, have a wafer Si uniformity of plus/minus about 5 nm, a buried oxide (BOX) thickness of about 380 nm (preferably from about 100–500 nm), a pinhole density of less than about 0.1 per $cm^2$, and metallics (TXRF) of less than about $5 \times 10^{10}$ $cm^2$. Also available are similar SIMOX wafers from IBIS under their trademarks ULSI and ADVANTOX™. The SIMOX layers 110 herein are from about 100 nm to 500 $\mu$m thick, preferably from about 100–250 nm thick, and most preferably from about 170–200 nm thick. SIMOX membrane structures 47 in SIMOX embodiments generally produce a more flat upper surface than do simple silicon wafer embodiments. SIMOX wafers with Si layer 68 increased in thickness by epitaxial growth produce membranes with less variation in membrane thickness for individual membranes produced from one wafer, as compared to membranes produced by wafer bond and etch back SOI.

According to another embodiment of this invention shown in FIGS. 10(a)–10(e), membrane structure 47 is formed by an anodic bonding process using single crystal silicon wafer 131. In this embodiment, the top of silicon wafer 131 is doped with etch stopping material 132 as shown in FIG. 10(a) to a predetermined desired depth. Thereafter, the back side of the wafer is masked 133 (FIG. 10(b)) and a protective layer typically placed on layer 132, and the wafer anisotropically etched as shown in FIG. 10(c) to produce a square flexible freestanding membrane portion 68, 135, and a square cavity in the wafer surrounded by shoulder area 134, the thin flexible freestanding membrane portion 68, 135 having a thickness corresponding to the depth of the doped silicon. Referring to FIG. 10(c), a protective layer (not shown) is typically placed on layer 132 across most of its upper surface during the etch process of layer 131, with this protective layer then being removed prior to the FIG. 10(e) bonding step. Because of the etch stopping area 132, the etching cannot penetrate all the way through the wafer, but stops at layer 132 thereby leaving the flexible membrane portion 68, 135. Then, a pyrex glass substrate 136 (equivalent to 61) is drilled with circular hole(s) 137 (equivalent to 63), and the etched silicon wafer is flipped and bonded to the drilled pyrex substrate 136 via anodic bonding as shown in FIG. 10(e) to form membrane structure 47.

According to other embodiments of this invention, membrane structure 47 may include an aluminum foil thin film anodically bonded to a drilled pyrex glass substrate. For example, a 5 mm thick aluminum film may be anodically bonded to such a pyrex glass substrate having a thickness of approximately 0.125", with drill hole(s) in the pyrex having a diameter of approximately 3.47 mm.

In some embodiments, a large area glass substrate may be provided and drilled with an array of holes, and thereafter diced or cut up into a plurality of squares in order to form different membrane structures 47. To help dice or separate such a structure into different pieces, scribe or separation lines may be provided on the wafers to facilitate the production of individual membranes. These diced up pyrex glass chips or squares may then be placed upon the aluminum foil with an anodic bond being formed at about 300° C. and about 1,200 volts DC bias, with the negative electrode applied to the pyrex.

According to still further embodiments, a membrane structure 47 may be formed of a stainless steel thin foil sheet, coated with a polysilicon layer, and anodically bonded to a pyrex glass substrate where the polysilicon layer forms an anodic bond with the pyrex (or other glass). Also, the membrane structure may be made from other materials amenable to anodic bonding.

It is noted that each of the membrane structures 47 discussed above (see FIGS. 6–10), can serve two different purposes. Firstly, the membrane structure 47 itself may be subjected to bulge testing in the FIG. 5(*a*) system in order to determine the characteristics and/or properties of the freestanding flexible film portion(s) 68 that covers the cavity. Thus, the stress and modulus characteristics of the flexible membrane portion 68 may be determined. The second use for each membrane structure 47 is to serve as a base or supporting structure upon which a thin film 57, which is to be analyzed, is deposited or otherwise disposed. For example, the FIG. 6(*c*) membrane structure 47 may be used as a base for a thin film polymer coating (e.g. photoresist) which is to be analyzed. In such as case, the thin film photoresist polymer coating 57 (preferably from about 500 Å to 5,000 Å thick) would be applied to the top surface of silicon (or other appropriate material) layer 65 of the FIG. 6(*c*) membrane structure so as to cover portion 68. When the overall structure including 47 and 57 is bulge tested in the FIG. 5(*a*) system, both flexible portion 68 of layer 65, and the corresponding portion of the overcoating polymer layer 57 are caused to bulge due to either pressure within cavity 53, or the cavity being evacuated. For example, see the "coated" graph in FIG. 5(*c*). In this way, given the prior knowledge of the characteristics and properties of layer 65 and portion 68, the stress and modulus characteristics of the thin film polymer overcoat 57 can be determined.

Array Membrane Structures

Each of the membrane structures 47 described above and illustrated in FIGS. 6–10 includes a single freestanding flexible membrane portion 68 which is exposed to pressure or evacuation for causing bulging or deflection. As discussed in the Background Section above, this does not enable one to determine the properties of a thin film, at different locations, across the surface area of a large substrate which is coated with the thin film. Accordingly, we have developed arrayed membrane structures 47, discussed below, which enable the testing and analysis of a thin film(s) at different locations across a large surface area of an underlying substrate.

FIG. 11 is a perspective view of an arrayed membrane structure 47 and corresponding mounting structure 202 according to one embodiment of this invention. This structure may, of course, be used within the FIG. 5(*a*) bulge testing system, where the XYZ stage is manipulated by computer-controlled system 55 so that transducer 49 can measure the amount of deflection for each individual stand alone flexible membrane portion 68, and optionally its overcoat thin film 57 in the array.

Still referring to FIG. 11, an array of eleven (although any number may be provided) different stand alone flexible membrane portions 68 are defined on the top surface of structure 47. Any of the membrane structures 47 illustrated in FIGS. 6–10 may be utilized in the FIG. 11 embodiment to form the array of flexible portions 68. For example, using the FIG. 6 type of membrane structure as an example, the arrayed membrane structure 47 in FIG. 11 may include an array of FIG. 6(*c*) type membrane structures, where a pyrex glass substrate 61 including eleven different apertures or holes 63 are drilled therein, and a flexible membrane portion 68 is provided over top of each of these eleven holes 63 due to a thin silicon layer 65 being applied across the entire surface area of substrate 61. Thus, in this example, layer 201 of the FIG. 11 membrane structure 47 would represent an arrayed glass pyrex substrate 61 with the plurality of holes 63 defined therein, while layer 203 would represent the silicon coating 65 applied over the array of holes 63. The silicon coating 65 applied over the array of holes 63 forms the array of flexible membrane portions 68 which can be bulge tested.

As can be seen in FIG. 11, given arrayed membrane structure 47, there is required a special mounting chuck 202 which takes the place of mounting structure 45 illustrated in FIG. 5(*a*). Mounting chuck 202 in the FIG. 11 embodiment includes at least a single pressure inlet aperture 204, as well as an array of holes or apertures 205 which correspond to the array of flexible membrane portions 68 in membrane structure 47. Thus, when membrane structure 47 is adhered to mounting chuck 202 via Crystal Bond™, (or some other rigid bond) pressurized gas is introduced into aperture 204 and flows, via hidden channel passageways defined in chuck 202, into each aperture 205 in the array thereby causing each flexible membrane portion 68 to bulge outwardly. Thus, the array of pressure apertures 205 in mounting chuck 202 allows pressurized fluid (e.g. gas, air, or liquid) to be applied to the underneath side of each flexible membrane portion 68 in the membrane structure thereby allowing bulge testing to be performed. Optionally, each cavity 53 in the array may be evacuated by applying a vacuum to aperture 204, in order to cause the films to bulge inwardly.

Following the determinations of the characteristics of flexible membrane portions 68 in the array via bulge testing, a thin film 57 may be applied or deposited across the entire top surface of the FIG. 11 membrane structure 47 either continuously or in a segmented manner, thereby covering at least some, if not all, of the arrayed membrane portions 68. Structure 47, with its overcoating 57, is then bulge tested in order to determine the stress and modulus characteristics of thin film 57 across a large surface area of the arrayed structure 47 covering a plurality of portions 68. In such a manner, not only is it possible to determine stress and modulus characteristics of thin film 57 at the center of array structure 47, but it is also possible to determine those same characteristics at the sides, edges, and other areas across the structure. This enables a user or operator to determine, for example, stress and modulus characteristics of a thin film that is deposited over a large surface area of a substrate, at different locations thereon. This, of course, is useful for measuring the uniformity of application of processes used to deposit a film(s) on a substrate. Also, a user could position strips or segments of different film 57 materials over different arrayed portions 68 so as to determine the characteristics of each such material over a large surface area.

FIG. 12 illustrates an arrayed membrane structure 47 according to another embodiment of this invention. In this embodiment, membrane structure 47 includes an arrayed top wafer or member 221 having an array of flexible membrane portions 68 defined therein, and bottom sealing wafer or member 222. Top member 221 and bottom member 222 are preferably rigidly coupled together in a hermetically sealed manner, with bottom member 222 being coupled to the mounting chuck in the same type manner.

Sealing wafer 222 has a single (or multiple) fluid inlet aperture(s) defined in a bottom surface thereof which allows pressurized gas, liquid, or air (or instead a vacuum to be applied) to flow into a channel system within structure 47 so as to selectively or simultaneously pressurize (or instead evacuate) the underside of each flexible membrane portion 68 in the array.

As illustrated in FIG. 13, sealing wafer 222 may have a single pressurized inlet port 204 which is connected to (e.g. continuously), or in communication with, each flexible membrane portion 68 via a corresponding cavity 53. Fluid channel system 223, which is provided in the FIG. 13 bottom sealing wafer 222, enables pressurized gas or liquid when inserted via aperture 204 to make its way to each of apertures 225. Each aperture 225 corresponds with, and is in communication with, a cavity 53 of a particular flexible membrane portion 68, so that pressurized gas from an aperture 225 causes the corresponding flexible membrane portion 68 to bulge. This bulging is outwardly toward transducer 49 in pressurizing embodiments, and inwardly toward the cavity in evacuating embodiments.

In the FIG. 14 embodiment of bottom sealing wafer 222, three separate pressurized inlet apertures 204 are provided. This enables apertures 225 and corresponding flexible membrane portions 68 in the array to be selectively pressurized, one row at a time. Also, the system can be designed so that one quadrant of the wafer can be selectively addressed at a time, and the like. Thus, pressurized gas may be applied to only one of the three inlet apertures 204, which results in only one row of flexible membrane portions 68 (and overcoated film(s) 57) being exposed to pressure and bulged. In a similar manner, it is possible to arrange the pressurized channel system, and the number of inlet apertures 204, in bottom wafer 222, so that each flexible membrane portion 68 (and overlying film 57) in the membrane structure array is individually selectively accessible. In such a manner, a user may selectively address each portion 68 in the array, one at a time.

Computer Programming/Software

FIGS. 15–70 herein illustrate system requirements and computer code for use in certain embodiments herein. Set forth below is a description of the operation of same.

Introduction: This documentation describes the operation of the LabVIEW Membrane Pressure Ramping Data Acquisition and Control Code. It also discusses the internal operation of the code. Additionally, associated utility programs are briefly discussed. The first section of this document should be read before attempting operation of the system.

System Requirements: This software was written under LabVIEW Version 3.1 running on MS Windows 3.1. Preferably, a 33 MHz or faster 486DX class machine is used for consistent reliable operation. It has been run on a 486DX/2 machine running at 66 MHz. Require RAM for operation is 8 Megabytes, while conservative disk space requirements start at about 5 Megabytes, depending on the duration and number of tests. The control and acquisition routines require a Computer Boards Corp. data acquisition board and the associated Universal Library Software with LabVIEW extensions. The proper functioning of the board must be confirmed before running tests, as this software has no means to detect improper operation and must accept nearly all input as valid.

Operation: This section describes system operation, the front panel interface, and the meaning and use of each control.

Operational Overview: The overall acquisition and control strategy used in this system is extremely simplistic, but with many built-in safeguards and error correction mechanisms. At runtime, a number of control data structures are initialized, and the hardware interface (Computer Boards Hardware) are enabled and initialized. The user is prompted to enter file names for data storage. If these initializations are successful (or the operator tells the system to ignore errors), the main control loop is entered. In this loop, the system reads the input arrays of time and pressure targets, and divides the time and pressure axes into equally spaced, small, discrete steps, and then walks through these steps and attempts to follow the steps to apply the desired pressure profile. At each step, the actual pressure and deflection are read by the hardware, displayed on the panel. When the final check-point is reached, the pressure is released, and the data and control buffers are transformed to disk. The test hardware is shutdown, disabled and returned to a user controllable configuration.

Front Panel Interface: The front panel consists of a number of standard LabVIEW controls and indicators. The following sections detail the controls on the front panel.

Pressure Range: Sets the appropriate valves and enables the correct regulator for operation in both high (e.g. 0–5 psi) and low (e.g. 0–1 psi) pressure ranges.

Displacement Sensitivity: Sets the sensitivity level of the displacement sensor in micrometers per millivolt.

Curvature Correction: Sets the second order correction value used to correct the displacement value for the curvature of the membrane while under pressure; the value should be entered in micrometers per millivolt per psi.

Time and Pressures: Arrays that allow the user to set the target times and pressure for the desired pressure ramping profile.

The following are the indicators which return values to the user.

Start Time: Displays the start time for this program run.

Elapsed Time: Displays the current elapsed time for this program run.

Datafile Name: Displays the file name the current data run will be stored in.

Measured Pressure: Graphical display of the measurements of the applied pressure profile for comparison to the desired profile.

Measured Deflection v. Pressure: Graphical display of the corrected measured deflection v. measured pressure profile.

Measured Deflection v. Time: Graphical display of the corrected measured deflection v. time.

Internals: This section describes the internal details of the programming, including the operation of the main program, and subsequently, of all the subroutines written for this program. A knowledge of LabVIEW programming is required for a thorough understanding of this section.

Overview: System execution consists of three main phases: initialization, loading and acquisition, and shutdown. The majority of the system's run time is spent in a main loop which encloses the loading and acquisition algorithms.

Initialization: During initialization, the Computer Boards acquisition and control board is enabled and the ports are set appropriately for input and output as necessary. The pressure regulators are set to zero. Empty arrays are initialized for the immediate storage of the data displayed in the three graphs on the front panel ("Initialize Array" function). The user is prompted for a file name without extension through a standard file dialog box ("File Dialog" function). The files are opened ("New File" function), if and only if the chosen names do not exist; if either of the names exist, or the name is not a valid one, a warning is presented to the user ("Prompt for Termination.vi"). A set of header data is written to the Main Data File immediately. Finally, the elapsed time clock is started ("Start Time.vi"). Future timer readings compared to this initial reading by simple subtraction to find the number of elapsed milliseconds. This simple algorithm has one known flaw. When the timer reaches (2^32)−1, it wraps to 0. This will cause non-sensical data to be produced in the event that this wrapping occurs. It was not considered worth the trouble to fix this problem, given the incredible rarity of its occurrence. Any time stamp inconsistencies can be corrected after the fact with relative ease.

Loading and Acquisition: This section encloses the bulk of both the code and execution time for this program. This discussion covers the actions taken by the program during a normal pass through the main loop. The main loop is entered once for each given Time-Pressure pair. At the beginning of the loop, the interval is divided into a large number of steps, and the pressure and time deltas for each step are calculated. An internal "stepper" loop is then begun. At each step, the program takes deflection and pressure measurements, and the corrects them for known systematic errors. The graphs and elapsed time indicators on the front panel are updated. Next the program enters a delay.

Shutdown: This phase produces a state which is safe both for data and specimen before terminating program operation. The pressure is set to zero, releasing the specimen from applied forces. All time series are stored to disk file, and the file is closed ("Close File" function). System operation terminates at this point.

Subroutines: The following subroutines are used in this program. General Arithmetic and Conversion functions are not mentioned.

LabVIEW built-in functions: See the LabVIEW documentation for these subroutines.
  Stop
  File Dialog
  New File
  Path to String
  Get Date/Time String
  Concatenate String
  Write File
  Tick Count (ms)
  Initialize Array
  Build Array
  Bundle
  Format and Append
  Close File Computer Boards Universal Library functions: See the Universal Library and LabVIEW Extensions documentation sets.
  Ain.vi
  Aout.vi
  ErrMsg.vi Custom Subroutines: The following functions were developed specifically for this program. They are all completely documented below.
  Continue.vi
  Set Regulator Once.vi
  Read Pressure.vi
  Read Pressure Once.vi
  Read Deflection Once.vi
  Read Voltage Once.vi Custom Subroutines: Discussion of each VI contains a number of sections. The Arguments list contains the names and types of each of the possible incoming controls. The Returns list contains the names and types of each of the possible outgoing indicators. The Subroutines Used List lists each contained function or SubVI for cross reference purposes. General Arithmetic and Conversion functions are not mentioned. Finally, the Function section describes in some technical detail exactly how the VI produces outputs from its inputs.

Read Voltage Once.vi:
Arguments: Board Number (Unsigned 32 bit integer), Channel Number (Signed 32 bit integer), Range Setting (Signed 32 bit integer)
Returns: Voltage (double), Error Message (String)
Subroutines Used:
  Ain.vi
  ErrMsg.vi
Function: This VI uses the Universal Library Routines from Computer Boards to interface with the data acquisition card. Consult the appropriate documentation for the internal operation of this VI.

Continue.vi
Arguments: Action Prompt (String)
Returns: True Boolean
Subroutines Used: None
Function: Used to force a pause in the program for user prompting. Pops up a dialog-like box.

Set Regulator Once.vi
Arguments: Board Number (Unsigned 32 bit integer), Channel Number (Signed 32 bit integer), Pressure to Set (Double), Pressure Units (Ring Control)
Returns: Error Message (String)
Subroutines Used: Aout.vi, ErrMsg.vi
Function: This VI sets the pressure the regulator is to apply. It determines the pressure range by the channel number (the proper regulator must be connected to the proper output channel).

Read Pressure.vi
Arguments: Averaging Cycles (Signed 32 bit integer), Output Units (Ring Control), Range Selector (Ring Control)
Returns: Pressure Measured (Double)
Subroutines Used: Read Pressure Once.vi
Function: Averages individual pressure readings for the number of cycles specified in the range specified. It then outputs the averaged value in the specified pressure units.

Read Pressure Once.vi
Arguments: Board Number (Unsigned 32 bit integer), Gauge Number (Unsigned 32 bit integer), Output Units (Ring Control)
Returns: Pressure Measured (Double), Voltage Measured (Double), Error Message (String)
Subroutines Used: Ain.vi, ErrMsg.vi Function: This VI reads the voltage value present in the specified board and port, and returns both that voltage (in volts) and the associated pressure (in the specified units).

Read Deflection.vi

Arguments: Averaging Cycles (Signed 32 bit integer)

Returns: Deflection Voltage (Double), Error Message (String)

Subroutines Used: Read Voltage Once.vi

Function: Reads and averages the voltage present on the deflection sensor channel over the number of sampling cycles given in the argument.

Returns: Error Code (Signed 32 bit integer), Valve State (Boolean)

Once given the above disclosure, many other features, modifications, and improvements will become apparent to the skilled artisan. Such other features, modifications, and improvements are, therefore, considered to be a part of this invention, the scope of which is to be determined by the following claims.

What is claimed is:

1. A method of bulge testing a film or coating at a plurality of different locations, the method comprising the steps of:

providing a bulge testing membrane structure including a plurality of freestanding membrane portions located on a single substrate, each of said freestanding membrane portions being disposed adjacent a corresponding pressure cavity so that one entire side of each freestanding membrane portion is exposed to pressurized fluid in the cavity thereby causing the freestanding membrane portion to bulge outwardly away from the cavity;

providing a film or coating on the membrane structure, over top of the plurality of freestanding membrane portions;

pressurizing the pressure cavities so as to cause the plurality of freestanding membrane portions to deflect or bulge along with the corresponding and overlying film or coating provided thereon and without causing said overlying film or coating to peel from said membrane portions;

measuring the deflection of a plurality of the freestanding membrane portions and corresponding overlying film or coating portions caused by said pressurizing, and based upon said measuring determining mechanical properties of the overlying film or coating portions at a plurality of different locations.

2. The method of claim 1, wherein an array of the freestanding membrane portions is provided in the membrane structure, and a corresponding array of pressure cavities is provided in the membrane structure, and wherein the thin film is continuous across the array of membrane portions.

3. The method of claim 2, further comprising the steps of selectively pressurizing the pressure cavities and corresponding freestanding membrane portions so that at a given point in time less than all of the pressure cavities and corresponding freestanding membrane portions are selectively pressurized.

4. The method of claim 1, further comprising the step of adhering the membrane structure to a mounting chuck, the mounting chuck including at least one pressure inlet aperture defined therein which is in fluid communication with the pressure cavities following said adhering.

5. The method of claim 1, wherein said measuring step includes optically measuring the deflection of the film or coating caused by said pressurizing, at locations corresponding to central areas of each of the freestanding membrane portions, and wherein said optical measuring is conducted in a non-contacting manner so that optical measuring equipment does not contact the film or coating.

6. The method of claim 1, wherein said measuring step is carried out by a non-contacting type of transducer, and by one of: atomic force microscopy, an electrical method based upon capacitive and inductive measurement.

7. The method of claim 1, further comprising the step of mapping the variation of stress and modulus properties of the film or coating that are detected via said bulge testing.

8. The method of claim 1, wherein the film or coating includes one of: metal foil, metal film, polymer film, paint film or coating, semiconductor thin film, copper thin film, ceramic film, aluminum thin film, gold thin film, nickel thin film, adsorbed species (monolayer thin film), dielectric thin film, and ITO thin film.

9. The method of claim 1, further comprising the step of determining the thickness of the film or coating and using the thickness of the film or coating in calculating residual stress, creep, and elastic modulus characteristics of the film or coating.

10. A method of bulge testing a thin film at a plurality of locations, the method comprising the steps of:

providing a bulge testing membrane structure including a plurality of freestanding membrane portions located on a single substrate, each of said freestanding membrane portions being disposed adjacent a corresponding cavity having a corresponding fluid outlet, so that a plurality of discrete cavities and corresponding cavity fluid outlets are provided adjacent said freestanding membrane portions;

providing a thin film on the membrane structure, over top of the plurality of freestanding membrane portions;

evacuating a plurality of cavities via said fluid outlets, either simultaneously or separately, so as to cause the plurality of freestanding membrane portions to deflect or bulge inwardly along with the corresponding overlying thin film portions provided thereon and without causing said overlying film or coating to peel from said membrane; and measuring the deflection of a plurality of the freestanding membrane portions and corresponding overlying thin film portions caused by said evacuating, and based upon said measuring determining modulus and stress properties of the overlying the film portions at a plurality of different locations.

11. The method of claim 10, further comprising the step of patterning the overlying thin film into a plurality of discrete thin film portions, each of which overlies one of the cavities.

12. A method of bulge testing a film at a plurality of different locations, the method comprising the steps of:

providing a bulge testing apparatus including a major surface and a cavity defined therein;

providing a film on the major surface over top of the cavity;

evacuating the cavity by applying a vacuum thereto so as to cause the film to deflect inwardly and without causing said film to peel from said major surface; and measuring the deflection of the film caused by said evacuating at a plurality of different locations, and based upon said measuring determining modulus and stress properties of the film.

13. A method of bulge testing a film, the method comprising the steps of:

providing a bulge testing apparatus including a major surface and a cavity defined therein;

providing a film on the major surface over top of the cavity;

locating a center point on the film, the center point overlying approximately the center of the cavity;

locating first and second points spaced from the center point so that the first and second points are located in positions not susceptible to bulging, and wherein a line connecting the first and second points, and the center point, crosses a portion of the film overlying the cavity; and optically measuring bulging or deflection of the film, by measuring deflection of the center point relative to the first and second points which are positioned at undeflected locations.

14. The method of claim 13, wherein the deflection of the film is measured by way of laser triangulation.

15. The method of claim 12, wherein the deflection of the film is measured by way of white light interferometry.

16. The method of claim 13, further comprising the steps of pressurizing the cavity and measuring outward deflection of the film using said center point and said first and second points, and wherein the line drawn through said first and second points, and said center point, substantially bisects the portion of the film overlying the cavity.

17. The method of claim 13, wherein the cavity is neither pressurized nor evacuated, so that bulging or deflection of the film is caused by an overall residual stress.

18. The method of claim 13, further comprising the steps of evacuating the cavity and measuring inward deflection of the film using the center point, and the first and second points.

19. A method of bulge testing a film, the method comprising the steps of:

providing a bulge testing apparatus including a major surface and a cavity defined therein;

providing a film having a compressive residual stress on the major surface over top of said cavity;

allowing said film to bulge, either inwardly or outwardly, as a result of said compressive residual stress present in the film, without pressurizing or evacuating the cavity; and measuring bulging or deflection of the film caused by said stress, so that it is necessary to either pressurize or evacuate the cavity.

20. A method of bulge testing a film, the method comprising the steps of:

providing a bulge testing apparatus including a major surface and a cavity defined therein;

providing a film on the major surface over top of the cavity;

measuring a deflection or bulge of the film proximate the cavity;

storing a predetermined lookup table which enables determination of residual stress in the film based upon the film's material, thickness, and measured deflection; and using the lookup table to determine residual stress of the film indicated by the measured deflection, the determined residual stress being a function of the film's thickness, material, deflection, and of pressure applied in the cavity.

* * * * *